United States Patent [19]

Larsen et al.

[11] Patent Number: 5,272,078
[45] Date of Patent: Dec. 21, 1993

[54] CDNA ENCODING THE TYPE I IODOTHYRONINE 5'DEIODINASE

[75] Inventors: P. Reed Larsen, Brookline; Marla J. Berry, Brighton, both of Mass.

[73] Assignee: Brigham and Women's Hospital, Boston, Mass.

[21] Appl. No.: 828,790

[22] Filed: Jan. 29, 1992

Related U.S. Application Data

[63] Continuation-in-part of Ser. No. 757,024, Sep. 3, 1991, abandoned, which is a continuation-in-part of Ser. No. 647,657, Jan. 29, 1991, abandoned.

[51] Int. Cl.$^5$ ............... G12N 15/53; G12N 15/11; G12N 15/63; C12P 21/00
[52] U.S. Cl. ............... 435/189; 435/69.1; 435/172.1; 435/252.3; 435/320.1; 536/23.2; 536/24.1; 935/9; 935/11; 935/22; 935/44; 935/66; 935/79
[58] Field of Search ............... 435/69.1, 252.3, 320.1, 435/187; 536/27, 23.2, 24.1

[56] References Cited

U.S. PATENT DOCUMENTS

| | | | |
|---|---|---|---|
| 4,727,138 | 2/1988 | Goeddel et al. | 536/27 |
| 4,857,467 | 8/1989 | Sreekrishna et al. | 435/255 |
| 4,910,141 | 3/1990 | Wong et al. | 435/172.3 |
| 4,935,339 | 6/1990 | Zahradnik | 435/5 |
| 4,959,318 | 9/1990 | Foster et al. | 435/69.1 |
| 4,975,369 | 12/1990 | Beavers et al. | 435/69.1 |
| 5,075,227 | 12/1991 | Hagen | 435/172.3 |

OTHER PUBLICATIONS

Zinoni, F., et al., 1990, Proceedings of the National Academy of Sciences, USA, 87:4660–4664.
Schön, A., et al., 1989, Nucleci Acids Research, 17(18):7159–7165.
Leinfelder, W., et al., 1990, Proceedings of the National Academy of Sciences, USA, 87:543–547.
Forchhammer, K., et al., 1990, The Journal of Biological Chemistry, 265(16):9346–9350.
Stadtman, T. C. et al., 1991, BioFactors, 3(4): 21–27.
Baron, C., et al., 1990, Nucleic Acids Research, 18(23): 6761–6766.
Akasaka, M., et al., 1990, Nucleic Acids Research, 18(15): 4619.
Rocker, C., et al., 1991, Gene, 98(2): 193–200.
Fa, L., et al., 1991, Science, 251: 807–810.
Wen, L., et al., 1989, The Journal of Biological Chemistry, 264(15): 9016–9021.
Parkin, N. T. et al., 1988, The EMBO Journal, 7(9):2831–2837.
St. Germain et al., *The Journal of Biological Chemistry* 265(33):20087–20090 (1990).
Lee et al., *Molecular and Cellular Biology* 10(5):1940–1949 (1990).
Mullenbach et al., *Protein Engineering* 2(3):239–246.
Engelberg-Kulka et al., *TIBS* 13:419–421 (1988).
Söll, D., *Nature* 331:662–663 (1988).
Freedman, R. B., *Cell* 57:1069–1072 (1989).
Schoenmakers et al., *Biochemical and Biophysical Research Communications* 162(2):857–868 (1989).

(List continued on next page.)

*Primary Examiner*—Robert A. Wax
*Assistant Examiner*—William W. Moore
*Attorney, Agent, or Firm*—Sterne, Kessler, Goldstein & Fox

[57] ABSTRACT

The present invention is directed to the cloning, sequencing, and uses of a nucleotide sequence encoding the mammalian enzyme Type I iodothyronine 5' deiodinase and mutant sequences thereof. This enzyme catalyzes the conversion of thyroxine to triiodothyronine, producing the active form of thyroid hormone. The invention is further directed to the discovery that an untranslated nucleotide sequence is necessary for the recognition of a TGA (termination) codon in the coding region of 5' deiodinase as encoding selenocysteine, an amino acid essential for the full activity of 5' deiodinase. The mechanism by which this recognition occurs involves a stem-loop structure in the 3' untranslated region of the mRNA. The untranslated sequence can be used to incorporate selenocysteine into non-selenocysteine-containing proteins and polypeptides.

15 Claims, 21 Drawing Sheets

```
1572 ggcaccagca atgctgtcat tcagttatgc agaagctcat ttgtgaaatt ctgtttctct gatttcttcg caagtctctt aatggtcatt tgtgttagat 1672 tacatcaaac tgatggatag ccattggtat tcatctattt taactctgtg tctttacata tttgtttatg atggccacag cctaaagtac acacggctgt 1772 gacttgattc aaaagaaaat gttataagat gcagtaaact aataacagaa ttattaaaat atatcaggct aaaaaaagg aaccgcagtt cagacatttg 1872 gtgtatgtgc ttggctgagg ag
```

OTHER PUBLICATIONS

Boado et al., *Biochemical and Biophysical Research Communications* 155(3):1297–1304 (1988).
Boado et al., *Endocrinology* 123(3):1264–1273 (1988).
Boado et al., *Endocrinology* 124(5):2245–2251 (1989).
Boado et al., *Clinical Research* 36(1):122A (1988).
Boado et al., *Clinical Research* 36(1):180A (1988).
Larsen et al., *Endocrin. Rev.* 2:87–102 (1981).
Berry et al., *Nature*, 349(6803):438–440 (1991).
Berry et al., *Mol. Endocrinol.*, 4(5):743–748 (1990).
Berry et al., *Nature*, 353:273–276 (1991).
Berry et al., *J. Biol. Chem.*, 266(22):14155–14158 (1991).
Berry et al., *Endocrinology*, 129(1):550–552 (1991).
International Search Report, cited in Int. Appln. No. PCT/US92/00740 (PCT filing of present appln.), dated Jun. 10, 1992.

```
  1  GCTGAGATGGGGCTGTCCCAGCTATGGCTGTGGCTGAAGCGGCTTGTGATATTCCTGCAG
          M  G  L  S  Q  W  L  W  L  K  R  L  V  I  F  L  Q
 61  GTAGCCTTGGAGGTGGCTACGGGCAAGGTGCTAATGACACTGTTCCCAGAGAGAGTCAAG
       V  A  L  E  V  A  T  G  K  V  L  M  T  L  F  P  E  R  V  K
121  CAGAACATCCTGGCCATGGGCCAAAAGACCGGAATGACCAGGAATCCCCGATTCGCCCCT
       Q  N  I  L  A  M  G  Q  K  T  G  M  T  R  N  P  R  F  A  P
181  GACAACTGGGTCCCCACCTTCTTCAGCATCCAGTACTTCTGGTTCGTCCTGAAGGTCCGC
       D  N  W  V  P  T  F  F  S  I  Q  Y  F  W  F  V  L  K  V  R
241  TGGCAGAGACTGGAAGACAGGGCTGAGTATGGGGGGCTGGCCCCCAACTGCACCGTGGTC
       W  Q  R  L  E  D  R  A  E  Y  G  G  L  A  P  N  C  T  V  V
301  CGCCTCTCAGGACAGAAGTGCAACGTCTGGGATTTCATTCAAGGCAGCAGACCCCTGGTG
       R  L  S  G  Q  K  C  N  V  W  D  F  I  Q  G  S  R  P  L  V
361  TTGAACTTCGGCAGCTGCACCTGACCTTCATTTCTTCTCAAATTTGACCAGTTCAAGAGA
       L  N  F  G  S  C  T  SC P  S  F  L  L  K  F  D  Q  F  K  R
421  CTCGTAGACGACTTTGCCTCCACAGCTGACTTCCTCATCATTTACATTGAAGAAGCTCAC
       L  V  D  D  F  A  S  T  A  D  F  L  I  I  Y  I  E  E  A  H
481  GCCACAGATGGATGGGCTTTTAAGAACAACGTGGACATCAGGCAGCACCGAAGCCTCCAG
       A  T  D  G  W  A  F  K  N  N  V  D  I  R  Q  H  R  S  L  Q
541  GACCGCCTGCGGGCAGCACATCTGCTGCTGGCCAGGAGCCCCCAGTGTCCTGTGGTGGTG
       D  R  L  R  A  A  H  L  L  L  A  R  S  P  Q  C  P  V  V  V
601  GACACAATGCAGAACCAGAGCAGCCAGCTCTATGCAGCTCTGCCTGAGAGGCTCTATGTG
       D  T  M  Q  N  Q  S  S  Q  L  Y  A  A  L  P  E  R  L  Y  V
661  ATACAGGAAGGCAGGATCTGCTACAAGGGTAAACCTGGCCCTTGGAACTACAATCCTGAG
       I  Q  E  G  R  I  C  Y  K  G  K  P  G  P  W  N  Y  N  P  E
721  GAAGTCCGAGCTGTTCTGGAAAAGCTTTGCATCCCACCTGGACACATGCCTCAGTTCTAG
       E  V  R  A  V  L  E  K  L  C  I  P  P  G  H  M  P  Q  F  *
```

FIG. 1

```
 781  GGGGCCAGCAGGAAGGTCCCCCAAGCTTGGTACTCCTCCCCACCAGTACAGATGTCCTTT
      AGCTTTGACCTTCGTTCCCAGATCAATTACTAGCTCAGATTTTTCTGATCTGAACAAATA
 901  ACTACCCGGGAGGCAATTCAGTTCACAGCACCCAACCAGCACAAATTGTTACAACCAGAG
      ATAAAGCAATACCGAGCTGTTAGCAAAAGTAAGTGTGCAGCTTTGCACCACTCCCACAGG
1021  CGGAGACCAATCCAGTGTGTGCCCCTTCTGGTGGAAGGGTACTCATGCTTGGTTGGCTGA
      CTTCTGAAGTGTAGTGACTCATGATGATGACGTCAAAAGCTCAATCCATTTGCCCAAGTT
1141  TGCCACTCATAGAATCAGTTGTTTAGTACCAAGCGACAGGCAGGCGTATTTCTACTTGTA
      GGAACCAAAGACATTGGAAACACTTTTCTGGCCCTAAGATTGAAATCCGTTAATATTGTT
1261  GGTGATAGGTGTTTCCATGGCAACCTATAATCTAATTCTGCTCCCTCTACCATCTTTGAA
      TAGATTGCAGAGAAATCTGGCTCTCTGGTACTGACACAAAAGCTTTATAACTTTAACTAA
1381  ACCAAATCACAGGCGCCAGCAAAAGCTGCCATTCCCCTGCTGTAACTCTGTTCCACTGGC
      GCCCAGTCTCTTACTGGTCTTTCATGTTAGATGGCTTTGGACTGACGGGTAGCCATGGGT
1501  TCATCTGTCATGTCTGCTTCTTTTTATATTTGTTTATGATGGTCACAGTGTAAAGTTCAC
      ACAGCTGTGACTTGATTTTTAAAAATGTCGGGAAGATGCAGCAAGCTAACGATTAAAATC
1621  CGTCAGGCTATTTTTGAATGGCTCCGGTGTGATCCTTACAATTTCCTTTCTGACTTGTGT
      ATGTGGGCCTGCTCTGCCGTCTTTTCCGATAGCCCACGTGTAATGTAATCAGCTAAGGCA
1741  TCGTTTGCCTGGAGGGACCCCGTCCTGGAGGAAGAAGCTCGTATGTGGCACGCATCCAAC
      ATGTTGTCCTGTGAAGTGTTGTGGAAGGGACGTGGCTGTTCACGTCACAGCAAAGCACCT
1861  TTAGGGGTGATGCGTGAATGGACCTGGGGAGCATTCTCCAGGCATCCAAACAGTTCCTCC
      TTGCTCTGCCTTAGGGCTACACCCAATACTGTAACATTGCATTTATGTATGGATTTAGGT
1981  GAGTCAGGATCTAGCTATAAAGTCGAGAGTGGCTGTGAACTTACAATCTTCAGACTCAGA
      GTAGCTGGGATTCCAGGTCTGTCCCCCTATATAAAAAATGCTTTTGACCTCTTGAAAAAA
2101  AAAAAA
```

FIG.1(cont.)

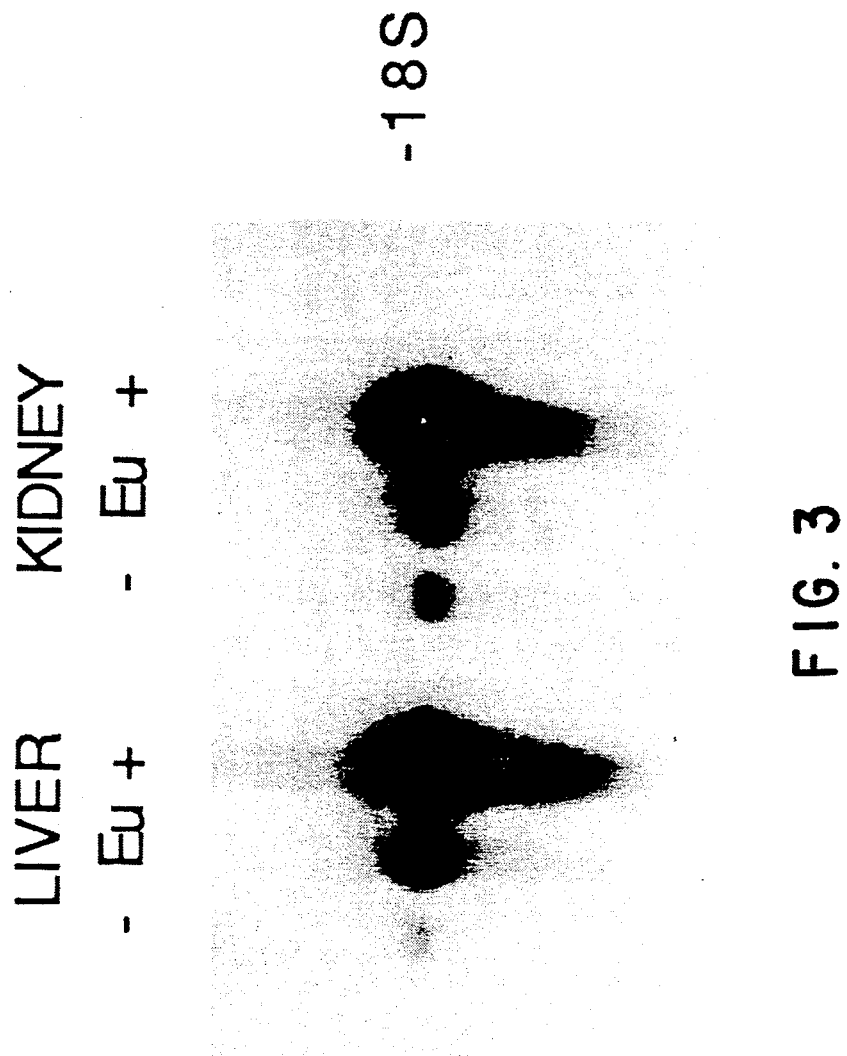

```
  1  GCCGAGATGGGGCTGCCCCAGCCAGGGCTGTGGCTGAAGAGGCTCTGGGTGCTCTTGGAG
        M  G  L  P  Q  P  G  L  W  L  K  R  L  W  V  L  L  E
 61  GTGGCTGTGCATGTGGTCGTGGGTAAAGTGCTTCTGATATTGTTTCCAGACAGAGTCAAG
      V  A  V  H  V  V  V  G  K  V  L  L  I  L  F  P  D  R  V  K
121  CGGAACATCCTGGCCATGGGCGAGAAGACGGGTATGACCAGGAACCCCCATTTCAGCCAC
      R  N  I  L  A  M  G  E  K  T  G  M  T  R  N  P  H  F  S  H
181  GACAACTGGATACCAACCTTTTTCAGCACCCAGTATTTCTGGTTCGTCTTGAAGGTCCGT
      D  N  W  I  P  T  F  F  S  T  Q  Y  F  W  F  V  L  K  V  R
241  TGGCAGCGACTAGAGGACACGACTGAGCTAGGGGGTCTGGCCCCAAACTGCCCGGTGGTC
      W  Q  R  L  E  D  T  T  E  L  G  G  L  A  P  N  C  P  V  V
301  CGCCTCTCAGGACAGAGGTGCAACATTTGGGAGTTTATGCAAGGTAATAGGCCACTGGTG
      R  L  S  G  Q  R  C  N  I  W  E  F  M  Q  G  N  R  P  L  V
361  CTGAATTTTGGAAGTTGTACCTGACCTTCATTTATGTTCAAATTTGACCAGTTCAAGAGG
      L  N  F  G  S  C  T SeC  P  S  F  M  F  K  F  D  Q  F  K  R
421  CTTATTGAAGACTTTAGTTCCATAGCAGATTTTCTTGTCATTTACATTGAAGAAGCACAT
      L  I  E  D  F  S  S  I  A  D  F  L  V  I  Y  I  E  E  A  H
481  GCATCAGATGGCTGGGCTTTTAAGAACAACATGGACATCAGAAATCACCAGAACCTTCAG
      A  S  D  G  W  A  F  K  N  N  M  D  I  R  N  H  Q  N  L  Q
541  GATCGCCTGCAGGCAGCCCATCTACTGCTGGCCAGGAGCCCCCAGTGCCCTGTGGTGGTG
      D  R  L  Q  A  A  H  L  L  L  A  R  S  P  Q  C  P  V  V  V
601  GACACCATGCAGAACCAGAGCAGCCAGCTCTACGCAGCACTGCCTGAGAGGCTCTACATA
      D  T  M  Q  N  Q  S  S  Q  L  Y  A  A  L  P  E  R  L  Y  I
661  ATCCAGGAGGGCAGGATCCTCTACAAGGGTAAATCTGGCCCTTGGAACTACAACCCAGAG
      I  Q  E  G  R  I  L  Y  K  G  K  S  G  P  W  N  Y  N  P  E
721  GAAGTTCGTGCTGTTCTGGAAAAGCTCCACAGTTAATCTGGACAGATACCTCAATTCTAG
      E  V  R  A  V  L  E  K  L  H  S  *
```

FIG. 4B

```
 781 GTGACCAACGGGAGGGCTTCTCAAGGCTTAGCTCTCCCTGAGACCCAGCTGGCTTTTACC
 841 CTTGACCTGTGTCCCTAGCTGAATCACTAGCTCAGATTTTTCTGATCTAAGCAAACAACT
 901 CCCAGCTGAGGAATGCAGGCCACAGCACCCAATCAAGACAAATTGTTATTATCAGAAAAT
 961 GAAGCAACACTTGAGCTGTTCAGGCCAGTTCCCTGTTGAAGAAACAGTTCCCTGTTGAAG
1021 AAAGTAGAGCCTGACACTGCTCCCACTTTGGAGATCACATTCCCTGCACACGGTCTTTGA
1081 GAGAGCAGTTGCACTCTACAGGCACACTTCTGAGGTACGGTATCTCTCTCCAGCCACTCT
1141 GATACCAAGTAATTCAAGCTGGCATTCCTTCTATTAGGGAAATTCATTTTACCCAATTTG
1201 CATTTATGGAATTGATCATTTAAGACACTAAATTAGTTTTTAGAACCAATTATGGGAAGA
1261 ATTCCAGTTGTTAGGAAGAGATGAGGAGTTGGAAGAGGAGGGATTAGAAACAGGAGGAGG
1321 CAGTCATCCTCTCCTTGCCAAAAGATTTAAACCTGTCCACATTGGTGGTGATGATGGGTG
1381 AGTTTCCATGGTAACACATCCCTAATTTTACCAGGGAAGAGGAGAGTACTCACTTTACCA
1441 TCTTTGAATATATTTCATAGAAATCTAGCTCTCTGTACCCTGAAATCTTCCACTAGCCTC
1501 ACTTTTCAACAGAGTCATCTAGAAGGGAGGGTTGGCTTCCCAAAAGCATAACCTTGACCA
1561 AACCAAACAATAGGCACCAGCAATGCTGTCATTCAGTTATGCAGAAGCTCATTTGTGAAA
1621 TTCTGTTTCTCTGATTTCTTCGCAAGTCTCTTAATGGTCATTTGTGTTAGATTACATCAA
1681 ACTGATGGATAGCCATTGGTATTCATCTATTTTAACTCTGTGTCTTTACATATTTGTTTA
1741 TGATGGCCACAGCCTAAAGTACACACGGCTGTGACTTGATTCAAAAGAAAATGTTATAAG
1801 ATGCAGTAAACTAATAACAGAATTATTAAAATATATCAGGCTAAAAAAAAGGAACCGCAG
1861 GTTCAGACATTTGGTGTATGTGCTTGGCTGAGGAGCCAATGGGGCGAAGCTACCATCTGT
1921 GGGATTATGACTGAACGCCTCTAAGTCAGAATCCCGCCCAGGCGGAACGATACGGCAGCG
1981 CCGCGGAGCCTCGGTTGGCCTCGGATAGCCGGTCCCCGCCTGTCCCCGCCGGCGGGCCG
2041 CCCCCCCTCCACGCGCCCCGCGCGCGGGAGGGCGCGTGCCCCGCCGCGCGCCGGGAC
2101 CGGGGTCCGGTGCGGAGTGCCCTTCGTCCTGGGAAACGGGGCGCGGCCGGAAAGGCGGCC
2161 GCCCCCTCGCCCGTCACGCACCGCACGTTCGTGGGGAACCTGGCGCTAAACCATTCCTTT
2221 AG
```

FIG.4B(cont.)

```
      ***                        #
HUMAN GCCGAGAGATGGGGCTGCCCCAGCCAGGGCTGTGGCTGAAGAGGCTCTGGTGCTGTGCATGTGGTGGGTAAAGTGCTTCTGATAT  100
RAT         T    T   TT        C  TGT AAT CC  A CT GG  CTAC  C G     AA   CC

TGTTTCCAGAGACAGAGTCAAGCGGAAACATCCTGGCCATGGGCGAAGAGCGGGTATGACCAGGAACCCCATTTCAGCCACGACAACTTGGATACCAACCTT  200
         C   G    A                 CA  CA           T      GA  GC CT         GC CC

TTTCAGCACCCAGTATTTCTGGTTCGTCTTGAAGGTCCGTTGGCAGCCAGAGGACGACTGAGCTAGAGGGGGTCTCGGCCCCAAACTGCCCGGTGGTC  300
      C   T     C        C             CC     A    GA    GG  TAT  G    C    A C
                                                                     ***
      CGCCCTCTCAGGACAGAGGTGCAACATTTGGGAGTTTATGCAAGGTAATAGGCCACTGGTGCTGAATTTTGGAAGTTGTACCTTCATTTATGTTCA  400
          A     GC   TCT  CGC AC T CCCCC                                             CTC

AATTTGACCAGTTCAAGAGGCTTATTGAAGACTTTAGTTCCATAGACAGATTTCTGTCATTTACATTGAAGAAGCACATCAGATGGCTGGGCTTT  500
         A CGAC   GCC   C  CTCC CA              T  CA                   A

TAAGAACAACATGGACATCAGAAATCACCAGAACCTTCAGGATGCCTGCAGCCCATGCTACTGCTGGCCAGGAGCCCCAGTGCCTGTGGTGGTG  600
         G   GC G   GAGC  C   G        A       G             T

GACACCATGCAGAACCAGAGACAGCCAGTCTACGCGACAGCTGCCTGAGAGGCTCTACATAATCCAGGAGGGCAGGATCCTCTACAAGGGTAAATCTGGCC  700
         A                T    T                          TGG A  A         TG                        C

CTTGGAAACTACAACCCAGAGGAAGTTCGTGCTGTTCTGGAAAAGCTCCACAGTTAA
         T     C A                                          TTG TCCC CCTGGACACATGCCTCAGTTCTAG  780
```

FIG.5

UGA CODON MUTANTS

| cDNA | mRNA | TRANSLATION | RELATIVE DEIODINASE ACTIVITY OOCYTES |
|---|---|---|---|
| TGA | UGA | OPAL OR SECYS | 100% |
| TAA | UAA | OCHRE | 0 |
| TTA | UUA | LEUCINE | 0 |
| TGT | UGU | CYSTEINE | 10% |

FIG.8

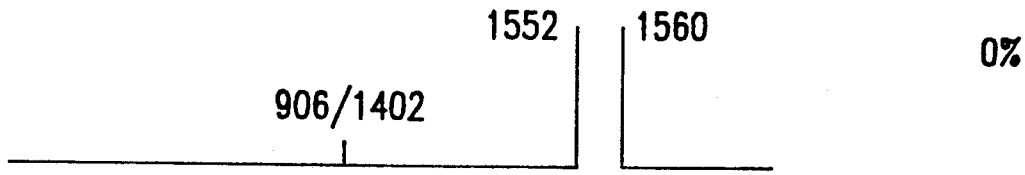
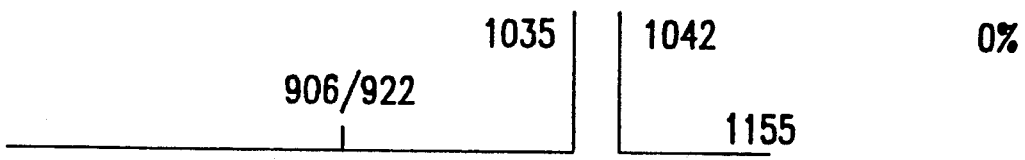
FIG. 15

```
RAT 5'DI    (1523)  TTTATATTTG TTTATGATGG .TCACAGTGT AAAGTTCACA CAGCTGTG.A CTTGATTTTT ..AAAAATGT CGGGAAGA
HUMAN 5'DI  (1726)  TACATATTTG TTTATGATGG .CCACAGCCT AAAGTACACA CGGCTGTG.A CTTGATTCAA AAGAAAATGT TATAAGA.
5'DI CONSENSUS      T..ATATTTG TTTATGATGG ..CACAG..T AAAGT.CACA C.GCTGTG.A CTTGATT... ...AAAATGT ....A....

RAT GPX     (1004)  GGGAGGTTTT TCCATGACGG TGTTCCTCT  AAATTTACAT GGAGAAAC.A CCTGATTTCC AGAAAAATCC CCTCAGAT
MOUSE GPX   (1168)  GGGCGGTTCT TCCATGATGG TGTTCCTCT  AAATTTGCAC GGAGAAAC.A CCTGATTTCC AGGAAAATCC CCTCAGAT
HUMAN GPX   (942)   GGGGTTTTCA TCTATGAGGG TGTTCCTCT  AAACCTACGA GGAGGAACA  CCTGATCTTA CAGAAAATAC CACCTCGA
BOVINE GPX  (695)   AGGGATTTTG CCCATGAAGG TGTCCCTCT  AAACCTACGT GGAGGAAT.G CCTGATGTCC AGGAAAATCC CCTGAGGT
GPX CONSENSUS       .GG...TT.. .C.ATGA.GG TGTT.CCTCT AAA..T.C.. GG....A... CCTGAT.T.. ...AAAAT.C C.......

5'DI CONSENSUS      T..ATATTTG TTTATGATGG ..CACAG..T AAAGT.CACA C.GCTGTG.A CTTGATT... ...AAAATGT ....A....
GPX CONSENSUS       .GG...TT.. .C.ATGA.GG TGTT.CCTCT TTT..T.C.. GG....A... CCTGAT.T.. ...AAAAT.C C.......
SECIS CONSENSUS     ......TT.. ...ATGA.GG ..........T AAA....... .......... C.TGAT.... ....AAAAT. ........
```

FIG.16

1572 ggcaccagca atgctgtcat tcagttatgc agaagctcat ttgtgaaatt ctgtttctct gatttcttcg caagtctctt aatggtcatt tgtgttagat 1672 tacatcaaac tgatggatag ccattggtat tcatctattt taactctgtg tctttacata tttgtttatg atggccacag cctaaagtac acacggctgt 1772 gacttgattc aaaagaaaat gttataagat gcagtaaact aataacagaa ttattaaaat atatcaggct aaaaaaaagg aaccgcagtt cagacatttg 1872 gtgtatgtgc ttggctgagg ag

FIG.17

922 GAAGCCCTGC TGTCCAAGCA GCCTAGCAAC CCCTAAGGCA TTCCTGGTAT

CTGGGCTTGG TGATGGCTGG CTGCCCTCCG GGGGGAGGTT TTTCCATGAC

1022 GGTGTTTCCT CTAAATTTAC ATGGAGAAAC ACCTGATTTC CAGAAAAATC

CCCTCAGATG GGCGCTGGTC TCGTCCATTC CCGATGCCTT TACGCCTAAA

1122 GAAAGGCGGT TCACCACTA AGAATAAAGT GCTG

FIG.18

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 2106 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:1:

```
GCTGAGATGG GGCTGTCCCA GCTATGGCTG TGGCTGAAGC GGCTTGTGAT ATTCCTGCAG      60
GTAGCCTTGG AGGTGGCTAC GGGCAAGGTG CTAATGACAC TGTTCCCAGA GAGAGTCAAG     120
CAGAACATCC TGGCCATGGG CCAAAAGACC GGAATGACCA GGAATCCCCG ATTCGCCCCT     180
GACAACTGGG TCCCCACCTT CTTCAGCATC CAGTACTTCT GGTTCGTCCT GAAGGTCCGC     240
TGGCAGAGAC TGGAAGACAG GGCTGAGTAT GGGGGGCTGG CCCCCAACTG CACCGTGGTC     300
CGCCTCTCAG GACAGAAGTG CAACGTCTGG GATTTCATTC AAGGCAGCAG ACCCCTGGTG     360
TTGAACTTCG GCAGCTGCAC CTGACCTTCA TTTCTTCTCA AATTTGACCA GTTCAAGAGA     420
CTCGTAGACG ACTTTGCCTC CACAGCTGAC TTCCTCATCA TTTACATTGA AGAAGCTCAC     480
GCCACAGATG GATGGGCTTT TAAGAACAAC GTGGACATCA GGCAGCACCG AAGCCTCCAG     540
GACCGCCTGC GGGCAGCACA TCTGCTGCTG GCCAGGAGCC CCAGTGTCC TGTGGTGGTG      600
GACACAATGC AGAACCAGAG CAGCCAGCTC TATGCAGCTC TGCCTGAGAG GCTCTATGTG     660
ATACAGGAAG GCAGGATCTG CTACAAGGGT AAACCTGGCC CTTGGAACTA CAATCCTGAG     720
GAAGTCCGAG CTGTTCTGGA AAAGCTTTGC ATCCCACCTG GACACATGCC TCAGTTCTAG     780
GGGGCCAGCA GGAAGGTCCC CCAAGCTTGG TACTCCTCCC CACCAGTACA GATGTCCTTT     840
AGCTTTGACC TTCGTTCCCA GATCAATTAC TAGCTCAGAT TTTTCTGATC TGAACAAATA     900
ACTACCCGGG AGGCAATTCA GTTCACAGCA CCCAACCAGC ACAAATTGTT ACAACCAGAG     960
ATAAAGCAAT ACCGAGCTGT TAGCAAAAGT AAGTGTGCAG CTTTGCACCA CTCCCACAGG    1020
CGGAGACCAA TCCAGTGTGT GCCCCTTCTG GTGGAAGGGT ACTCATGCTT GGTTGGCTGA    1080
CTTCTGAAGT GTAGTGACTC ATGATGATGA CGTCAAAAGC TCAATCCATT TGCCCAAGTT    1140
TGCCACTCAT AGAATCAGTT GTTTAGTACC AAGCGACAGG CAGGCGTATT TCTACTTGTA    1200
GGAACCAAAG ACATTGGAAA CACTTTTCTG GCCCTAAGAT TGAAATCCGT TAATATTGTT    1260
```

```
GGTGATAGGT GTTTCCATGG CAACCTATAA TCTAATTCTG CTCCCTCTAC CATCTTTGAA    1320

TAGATTGCAG AGAAATCTGG CTCTCTGGTA CTGACACAAA AGCTTTATAA CTTTAACTAA    1380

ACCAAATCAC AGGCGCCAGC AAAAGCTGCC ATTCCCCTGC TGTAACTCTG TTCCACTGGC    1440

GCCCAGTCTC TTACTGGTCT TTCATGTTAG ATGGCTTTGG ACTGACGGGT AGCCATGGGT    1500

TCATCTGTCA TGTCTGCTTC TTTTTATATT TGTTTATGAT GGTCACAGTG TAAAGTTCAC    1560

ACAGCTGTGA CTTGATTTTT AAAATGTCG GGAAGATGCA GCAAGCTAAC GATTAAAATC     1620

CGTCAGGCTA TTTTTGAATG CTCCGGTGT GATCCTTACA ATTTCCTTTC TGACTTGTGT     1680

ATGTGGGCCT GCTCTGCCGT CTTTTCCGAT AGCCCACGTG TAATGTAATC AGCTAAGGCA    1740

TCGTTTGCCT GGAGGGACCC CGTCCTGGAG GAAGAAGCTC GTATGTGGCA CGCATCCAAC    1800

ATGTTGTCCT GTGAAGTGTT GTGGAAGGGA CGTGGCTGTT CACGTCACAG CAAAGCACCT    1860

TTAGGGGTGA TGCGTGAATG GACCTGGGGA GCATTCTCCA GGCATCCAAA CAGTTCCTCC    1920

TTGCTCTGCC TTAGGGCTAC ACCCAATACT GTAACATTGC ATTTATGTAT GGATTTAGGT    1980

GAGTCAGGAT CTAGCTATAA AGTCGAGAGT GGCTGTGAAC TTACAATCTT CAGACTCAGA    2040

GTAGCTGGGA TTCCAGGTCT GTCCCCCTAT ATAAAAATG CTTTTGACCT CTTGAAAAAA     2100

AAAAAA                                                                2106
```

(3) INFORMATION FOR SEQ ID NO:2:

(i) SEQUENCE CHARACTERISTICS:
        (A) LENGTH: 257 amino acids
        (B) TYPE: amino acid
        (C) TOPOLOGY: linear (ii) MOLECULE TYPE: peptide (ix) FEATURE:
        (D) OTHER INFORMATION: Xaa at 126 is selenocysteine (xi) SEQUENCE DESCRIPTION: SEQ ID NO:2:

```
Met Gly Leu Ser Gln Leu Trp Leu Trp Leu Lys Arg Leu Val Ile Phe
 1               5                  10                  15

Leu Gln Val Ala Leu Glu Val Ala Thr Gly Lys Val Leu Met Thr Leu
20                  25                  30

Phe Pro Glu Arg Val Lys Gln Asn Ile Leu Ala Met Gly Gln Lys Thr
35                  40                  45

Gly Met Thr Arg Asn Pro Arg Phe Ala Pro Asp Asn Trp Val Pro Thr
50                  55                  60

Phe Phe Ser Ile Gln Tyr Phe Trp Phe Val Leu Lys Val Arg Trp Gln
65                  70                  75                  80

Arg Leu Glu Asp Arg Ala Glu Tyr Gly Gly Leu Ala Pro Asn Cys Thr
85                  90                  95

Val Val Arg Leu Ser Gly Gln Lys Cys Asn Val Trp Asp Phe Ile Gln
100                 105                 110

Gly Ser Arg Pro Leu Val Leu Asn Phe Gly Ser Cys Thr Xaa Pro Ser
115                 120                 125

Phe Leu Leu Lys Phe Asp Gln Phe Lys Arg Leu Val Asp Asp Phe Ala
130                 135                 140

Ser Thr Ala Asp Phe Leu Ile Ile Tyr Ile Glu Glu Ala His Ala Thr
145                 150                 155                 160

Gly Trp Ala Phe Lys Asn Asn Val Asp Ile Arg Gln His Arg Ser
165                 170                 175

Leu Gln Asp Arg Leu Arg Ala Ala His Leu Leu Leu Ala Arg Ser Pro
180                 185                 190

Gln Cys Pro Val Val Val Asp Thr Met Gln Asn Gln Ser Ser Gln Leu
```

|  |  | 195 |  |  |  | 200 |  |  |  | 205 |  |  |
|---|---|---|---|---|---|---|---|---|---|---|---|---|

Tyr Ala Ala Leu Pro Glu Arg Leu Tyr Val Ile Gln Glu Gly Arg Ile
210                 215                 220

Cys Tyr Lys Gly Lys Pro Gly Pro Trp Asn Tyr Asn Pro Glu Glu Val
225                 230                 235                 240

Arg Ala Val Leu Glu Lys Leu Cys Ile Pro Pro Gly His Met Pro Gln
245                 250                 255

Phe
257

( 4 ) INFORMATION FOR SEQ ID NO:3:

( i ) SEQUENCE CHARACTERISTICS:
( A ) LENGTH: 322 base pairs
( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO:3:

| GGCACCAGCA | ATGCTGTCAT | TCAGTTATGC | AGAAGCTCAT | TTGTGAAATT | CTGTTTCTCT | 60 |
|---|---|---|---|---|---|---|
| GATTTCTTCG | CAAGTCTCTT | AATGGTCATT | TGTGTTAGAT | TACATCAAAC | TGATGGATAG | 120 |
| CCATTGGTAT | TCATCTATTT | TAACTCTGTG | TCTTTACATA | TTTGTTTATG | ATGGCCACAG | 180 |
| CCTAAAGTAC | ACACGGCTGT | GACTTGATTC | AAAAGAAAAT | GTTATAAGAT | GCAGTAAACT | 240 |
| AATAACAGAA | TTATTAAAAT | ATATCAGGCT | AAAAAAAAGG | AACCGCAGTT | CAGACATTTG | 300 |
| GTGTATGTGC | TTGGCTGAGG | AG |  |  |  | 322 |

( 5 ) INFORMATION FOR SEQ ID NO:4:

( i ) SEQUENCE CHARACTERISTICS:
( A ) LENGTH: 234 base pairs
( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO:4:

| GAAGCCCTGC | TGTCCAAGCA | GCCTAGCAAC | CCCTAAGGCA | TTCCTGGTAT | CTGGGCTTGG | 60 |
|---|---|---|---|---|---|---|
| TGATGGCTGG | CTGCCCTCCG | GGGGGAGGTT | TTTCCATGAC | GGTGTTTCCT | CTAAATTTAC | 120 |
| ATGGAGAAAC | ACCTGATTTC | CAGAAAAATC | CCCTCAGATG | GGCGCTGGTC | TCGTCCATTC | 180 |
| CCGATGCCTT | TACGCCTAAA | GAAAGGCGGT | TTCACCACTA | AGAATAAAGT | GCTG | 234 |

( 2 ) INFORMATION FOR SEQ ID NO:5:

( i ) SEQUENCE CHARACTERISTICS:
( A ) LENGTH: 2222 base pairs
( B ) TYPE: nucleic acid
( C ) STRANDEDNESS: both
( D ) TOPOLOGY: linear ( i i ) MOLECULE TYPE: DNA ( i x ) FEATURE:
( A ) NAME/KEY: CDS
( B ) LOCATION: 7..756
( D ) OTHER INFORMATION: /note="Xaa=selenocysteine"

( x i ) SEQUENCE DESCRIPTION: SEQ ID NO:5:

GCCGAG ATG GGG CTG CCC CAG CCA GGG CTG TGG CTG AAG AGG CTC TGG    48
       Met Gly Leu Pro Gln Pro Gly Leu Trp Leu Lys Arg Leu Trp
       1               5                   10

| | | | | | | | | | | | | | | | | |
|---|---|---|---|---|---|---|---|---|---|---|---|---|---|---|---|---|
| GTG | CTC | TTG | GAG | GTG | GCT | GTG | CAT | GTG | GTC | GTG | GGT | AAA | GTG | CTT | CTG | 96 |
| Val | Leu | Leu | Glu | Val | Ala | Val | His | Val | Val | Val | Gly | Lys | Val | Leu | Leu | |
| 15 | | | | 20 | | | | | 25 | | | | | | 30 | |
| ATA | TTG | TTT | CCA | GAC | AGA | GTC | AAG | CGG | AAC | ATC | CTG | GCC | ATG | GGC | GAG | 144 |
| Ile | Leu | Phe | Pro | Asp | Arg | Val | Lys | Arg | Asn | Ile | Leu | Ala | Met | Gly | Glu | |
| | | | | 35 | | | | | 40 | | | | | 45 | | |
| AAG | ACG | GGT | ATG | ACC | AGG | AAC | CCC | CAT | TTC | AGC | CAC | GAC | AAC | TGG | ATA | 192 |
| Lys | Thr | Gly | Met | Thr | Arg | Asn | Pro | His | Phe | Ser | His | Asp | Asn | Trp | Ile | |
| | | | 50 | | | | | 55 | | | | | 60 | | | |
| CCA | ACC | TTT | TTC | AGC | ACC | CAG | TAT | TTC | TGG | TTC | GTC | TTG | AAG | GTC | CGT | 240 |
| Pro | Thr | Phe | Phe | Ser | Thr | Gln | Tyr | Phe | Trp | Phe | Val | Leu | Lys | Val | Arg | |
| | | 65 | | | | | 70 | | | | | 75 | | | | |
| TGG | CAG | CGA | CTA | GAG | GAC | ACG | ACT | GAG | CTA | GGG | GGT | CTG | GCC | CCA | AAC | 288 |
| Trp | Gln | Arg | Leu | Glu | Asp | Thr | Thr | Glu | Leu | Gly | Gly | Leu | Ala | Pro | Asn | |
| | 80 | | | | | 85 | | | | | 90 | | | | | |
| TGC | CCG | GTG | GTC | CGC | CTC | TCA | GGA | CAG | AGG | TGC | AAC | ATT | TGG | GAG | TTT | 336 |
| Cys | Pro | Val | Val | Arg | Leu | Ser | Gly | Gln | Arg | Cys | Asn | Ile | Trp | Glu | Phe | |
| 95 | | | | | 100 | | | | | 105 | | | | | 110 | |
| ATG | CAA | GGT | AAT | AGG | CCA | CTG | GTG | CTG | AAT | TTT | GGA | AGT | TGT | ACC | TGA | 384 |
| Met | Gln | Gly | Asn | Arg | Pro | Leu | Val | Leu | Asn | Phe | Gly | Ser | Cys | Thr | Xaa | |
| | | | | 115 | | | | | 120 | | | | | 125 | | |
| CCT | TCA | TTT | ATG | TTC | AAA | TTT | GAC | CAG | TTC | AAG | AGG | CTT | ATT | GAA | GAC | 432 |
| Pro | Ser | Phe | Met | Phe | Lys | Phe | Asp | Gln | Phe | Lys | Arg | Leu | Ile | Glu | Asp | |
| | | | 130 | | | | | 135 | | | | | 140 | | | |
| TTT | AGT | TCC | ATA | GCA | GAT | TTT | CTT | GTC | ATT | TAC | ATT | GAA | GAA | GCA | CAT | 480 |
| Phe | Ser | Ser | Ile | Ala | Asp | Phe | Leu | Val | Ile | Tyr | Ile | Glu | Glu | Ala | His | |
| | | 145 | | | | | 150 | | | | | 155 | | | | |
| GCA | TCA | GAT | GGC | TGG | GCT | TTT | AAG | AAC | AAC | ATG | GAC | ATC | AGA | AAT | CAC | 528 |
| Ala | Ser | Asp | Gly | Trp | Ala | Phe | Lys | Asn | Asn | Met | Asp | Ile | Arg | Asn | His | |
| | 160 | | | | | 165 | | | | | 170 | | | | | |
| CAG | AAC | CTT | CAG | GAT | CGC | CTG | CAG | GCA | GCC | CAT | CTA | CTG | CTG | GCC | AGG | 576 |
| Gln | Asn | Leu | Gln | Asp | Arg | Leu | Gln | Ala | Ala | His | Leu | Leu | Leu | Ala | Arg | |
| 175 | | | | 180 | | | | | 185 | | | | | 190 | | |
| AGC | CCC | CAG | TGC | CCT | GTG | GTG | GTG | GAC | ACC | ATG | CAG | AAC | CAG | AGC | AGC | 624 |
| Ser | Pro | Gln | Cys | Pro | Val | Val | Val | Asp | Thr | Met | Gln | Asn | Gln | Ser | Ser | |
| | | | | 195 | | | | 200 | | | | | 205 | | | |
| CAG | CTC | TAC | GCA | GCA | CTG | CCT | GAG | AGG | CTC | TAC | ATA | ATC | CAG | GAG | GGC | 672 |
| Gln | Leu | Tyr | Ala | Ala | Leu | Pro | Glu | Arg | Leu | Tyr | Ile | Ile | Gln | Glu | Gly | |
| | | | 210 | | | | 215 | | | | | | 220 | | | |
| AGG | ATC | CTC | TAC | AAG | GGT | AAA | TCT | GGC | CCT | TGG | AAC | TAC | AAC | CCA | GAG | 720 |
| Arg | Ile | Leu | Tyr | Lys | Gly | Lys | Ser | Gly | Pro | Trp | Asn | Tyr | Asn | Pro | Glu | |
| | | 225 | | | | | 230 | | | | | 235 | | | | |
| GAA | GTT | CGT | GCT | GTT | CTG | GAA | AAG | CTC | CAC | AGT | TAATCTGGAC | | AGATACCTCA | | | 773 |
| Glu | Val | Arg | Ala | Val | Leu | Glu | Lys | Leu | His | Ser | | | | | | |
| | 240 | | | | | 245 | | | | 250 | | | | | | |

ATTCTAGGTG ACCAACGGGA GGGCTTCTCA AGGCTTAGCT CTCCCTGAGA CCCAGCTGGC 833

TTTTACCCTT GACCTGTGTC CCTAGCTGAA TCACTAGCTC AGATTTTTCT GATCTAAGCA 893

AACAACTCCC AGCTGAGGAA TGCAGGCCAC AGCACCCAAT CAAGACAAAT TGTTATTATC 953

AGAAAATGAA GCAACACTTG AGCTGTTCAG GCCAGTTCCC TGTTGAAGAA ACAGTTCCCT 1013

GTTGAAGAAA GTAGAGCCTG ACACTGCTCC CACTTTGGAG ATCACATTCC CTGCACACGG 1073

TCTTTGAGAG AGCAGTTGCA CTCTACAGGC ACACTTCTGA GGTACGGTAT CTCTCTCCAG 1133

CCACTCTGAT ACCAAGTAAT TCAAGCTGGC ATTCCTTCTA TTAGGGAAAT TCATTTTACC 1193

CAATTTGCAT TTATGGAATT GATCATTTAA GACACTAAAT TAGTTTTTAG AACCAATTAT 1253

GGGAAGAATT CCAGTTGTTA GGAAGAGATG AGGAGTTGGA AGAGGAGGGA TTAGAAACAG 1313

GAGGAGGCAG TCATCCTCTC CTTGCCAAAA GATTTAAACC TGTCCACATT GGTGGTGATG 1373

ATGGGTGAGT TTCCATGGTA ACACATCCCT AATTTTACCA GGGAAGAGGA GAGTACTCAC 1433

```
TTTACCATCT TTGAATATAT TTCATAGAAA TCTAGCTCTC TGTACCCTGA AATCTTCCAC      1493

TAGCCTCACT TTTCAACAGA GTCATCTAGA AGGGAGGGTT GGCTTCCCAA AAGCATAACC      1553

TTGACCAAAC CAAACAATAG GCACCAGCAA TGCTGTCATT CAGTTATGCA GAAGCTCATT      1613

TGTGAAATTC TGTTTCTCTG ATTTCTTCGC AAGTCTCTTA ATGGTCATTT GTGTTAGATT      1673

ACATCAAACT GATGGATAGC CATTGGTATT CATCTATTTT AACTCTGTGT CTTTACATAT      1733

TTGTTTATGA TGGCCACAGC CTAAAGTACA CACGGCTGTG ACTTGATTCA AAAGAAAATG      1793

TTATAAGATG CAGTAAACTA ATAACAGAAT TATTAAAATA TATCAGGCTA AAAAAAGGA      1853

ACCGCAGGTT CAGACATTTG GTGTATGTGC TTGGCTGAGG AGCCAATGGG GCGAAGCTAC      1913

CATCTGTGGG ATTATGACTG AACGCCTCTA AGTCAGAATC CCGCCCAGGC GGAACGATAC      1973

GGCAGCGCCG CGGAGCCTCG GTTGGCCTCG GATAGCCGGT CCCCCGCCTG TCCCCGCCGG      2033

CGGGCCGCCC CCCCCTCCAC GCGCCCCGCG CGCGCGGGAG GGCGCGTGCC CCGCCGCGCG      2093

CCGGGACCGG GGTCCGGTGC GGAGTGCCCT TCGTCCTGGG AAACGGGGCG CGGCCGGAAA      2153

GGCGGCCGCC CCCTCGCCCG TCACGCACCG CACGTTCGTG GGGAACCTGG CGCTAAACCA      2213

TTCCTTTAG                                                              2222
```

( 2 ) INFORMATION FOR SEQ ID NO:6:

( i ) SEQUENCE CHARACTERISTICS:
        ( A ) LENGTH: 249 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Gly Leu Pro Gln Pro Gly Leu Trp Leu Lys Arg Leu Trp Val Leu
 1               5                  10                  15

Leu Glu Val Ala Val His Val Val Gly Lys Val Leu Leu Ile Leu
            20              25                  30

Phe Pro Asp Arg Val Lys Arg Asn Ile Leu Ala Met Gly Glu Lys Thr
        35                  40                  45

Gly Met Thr Arg Asn Pro His Phe Ser His Asp Asn Trp Ile Pro Thr
    50                  55                  60

Phe Phe Ser Thr Gln Tyr Phe Trp Phe Val Leu Lys Val Arg Trp Gln
65                  70                  75                  80

Arg Leu Glu Asp Thr Thr Glu Leu Gly Gly Leu Ala Pro Asn Cys Pro
                85                  90                  95

Val Val Arg Leu Ser Gly Gln Arg Cys Asn Ile Trp Glu Phe Met Gln
            100                 105                 110

Gly Asn Arg Pro Leu Val Leu Asn Phe Gly Ser Cys Thr Xaa Pro Ser
        115                 120                 125

Phe Met Phe Lys Phe Asp Gln Phe Lys Arg Leu Ile Glu Asp Phe Ser
    130                 135                 140

Ser Ile Ala Asp Phe Leu Val Ile Tyr Ile Glu Glu Ala His Ala Ser
145                 150                 155                 160

Asp Gly Trp Ala Phe Lys Asn Asn Met Asp Ile Arg Asn His Gln Asn
                165                 170                 175

Leu Gln Asp Arg Leu Gln Ala Ala His Leu Leu Leu Ala Arg Ser Pro
            180                 185                 190

Gln Cys Pro Val Val Val Asp Thr Met Gln Asn Gln Ser Ser Gln Leu
        195                 200                 205

Tyr Ala Ala Leu Pro Glu Arg Leu Tyr Ile Ile Gln Glu Gly Arg Ile
    210                 215                 220
```

```
Leu  Tyr  Lys  Gly  Lys  Ser  Gly  Pro  Trp  Asn  Tyr  Asn  Pro  Glu  Glu  Val
225                      230                      235                      240

Arg  Ala  Val  Leu  Glu  Lys  Leu  His  Ser
                    245
```

CDNA ENCODING THE TYPE I IODOTHYRONINE 5'DEIODINASE

CROSS-REFERENCE TO RELATED APPLICATIONS

This application is a continuation-in-part of U.S. patent application Ser. No. 07/757,024 filed Sep. 3, 1991, now abandoned which is a continuation-in-part of U.S. patent application Ser. No. 07/647,657, filed Jan. 29, 1991, now abandoned.

FIELD OF THE INVENTION

The present invention relates to the cloning, characterization and uses of both human and rat Type I iodothyronine 5' deiodinase, a selenocysteine-containing enzyme involved in the conversion of thyroxine to 3,3',5-triiodothyronine. The invention further relates to one or more mutant forms of the enzyme and the use of genes coding for such mutant forms as reporter genes.

BACKGROUND OF THE INVENTION

Virtually all of the metabolic and developmental effects of thyroid hormone are mediated by 3,3',5-triiodothyronine ($T_3$), which is produced from thyroxine ($T_4$) by 5' deiodination. Iodothyronine 5'-deiodination is catalyzed by two general classes of enzymes (Leonard, et al., In: Hennermann, G. (ed.), *Thyroid Hormone Metabolism*, Marcel Dekker, New York, pp. 289–229 (1986)) distinguished by their tissue distribution, physiological roles, $K_m$ for substrate, and sensitivity to propylthiouracil (PTU).

Type I deiodinase, present predominantly in liver and kidney, provides most of the plasma $T_3$ in the rat. This class of enzyme exhibits a $K_m$ for $T_4$ of ~2 μM and is sensitive to inhibition by PTU. Type II deiodinase, found in pituitary, cerebral cortex, and brown adipose, functions primarily to provide an intracellular source of $T_3$ for these tissues. This enzyme exhibits a $K_m$ for $T_4$ of ~2 nm and is PTU resistant. Many attempts at elucidating the molecular structure of these enzymes are in progress, but these efforts have to date been unsuccessful. Furthermore, the purification of these deiodinases has not been reported. (Berry, et al., *Mol. Endocrin.* 4:743–748 (1990).)

Regulation of both type I and type II deiodinase activities by thyroid hormone has been examined using tissue homogenates and microsomes (Kaplan, et al., *Endocrinology* 105:548–554 (1979); Kaplan, M. M., *Endocrinology* 105:548–554 (1979); Smallridge, et al., *Endocrinology* 111:2066–2069 (1982)). Activity levels of type I deiodinase in rat liver are low in the hypothyroid state and elevated in hyperthyroidism. Conversely, type II deiodinase activity levels are regulated in the opposite direction,, being low in tissues from hyperthyroid animals and elevated in hypothyroidism (Larsen, et al., *Endocr. Rev.* 2:87–102 (1981)). Since no specific reagents for quantitation of the enzymes have been developed, it has not been possible to confirm that these activity changes are due to alterations in the enzyme content or, if so, whether they are transcriptional or post-transcriptional.

It has also been suggested that Type I deiodinase, which requires reduced thiols for maximal enzyme activity, is closely related to rat protein disulfide isomerase (PDI) (Boada, et al., *Biochem. Biophys. Res. Comm.* 155:1297–1304 (1988)). However, this hypothesis has been discredited by at least two other groups, who assert that the clone isolated by Boado et al. actually codes for PDI. (Freeman, R. B., *Cell* 57:1069–1072 (1989); Schoenmakers, et al., *Biochem. Biophys. Res. Commun.* 162:857–868 (1989)).

Thus, despite its importance in thyroid hormone activation, Type I iodothyronine 5' deiodinase has not been well-characterized. The need for a DNA sequence encoding Type I iodothyronine 5' deiodinase is clearly recognized in the art.

SUMMARY OF THE INVENTION

The present invention meets the needs for a DNA sequence encoding Type I iodothyronine 5' deiodinase and for a method of achieving synthesis of 5' deiodinase, now discovered to be a selenocysteine-containing enzyme.

According to the present invention, a DNA sequence encoding Type I iodothyronine 5' deiodinase is disclosed. The product of this DNA sequence, and antibodies reacting with the product, are useful in relation to diagnosis and treatment of disease states related to thyroid function.

The invention also relates to the discovery that 5' deiodinase contains selenocysteine, an amino acid encoded by the termination codon TGA and previously identified in only one mammalian enzyme. According to the invention, a 3' untranslated segment of 5' deiodinase cDNA is essential for successful expression of the active selenocysteine-containing enzyme.

The invention further relates to the characterization of the 3' untranslated region of 5' deiodinase, and selenocysteine-insertion sequences. Such sequences are useful for incorporation of selenocysteine into peptides or proteins to study the effects of the presence of selenocysteine on the properties of such proteins.

The invention further relates to mutant gene sequences of iodothyronine 5' deiodinase. Such sequences, including for example the gene encoding the cysteine-126 mutant, as well as wild-type sequences are useful, for example, as "reporter" genes for monitoring transfection efficiencies or in the study of heterologous promoter function in transient expression assays.

The invention yet further relates to genetic constructs useful for the expression of selenocysteine-containing proteins, and methods of producing selenocysteine-containing proteins. Such methods, including the introduction of selenocysteine at a desired site into a polypeptide or protein when the native protein does not contain selenocysteine allow production of peptides or proteins with altered biochemical properties. These alterations provide insight into biochemical mechanisms, or result in proteins with properties that are advantageous over the native protein. Previous studies have shown that either chemical conversion of cysteine to selenocysteine in an intact protein (Wu and Hilvert, *J. Am. Chem. Soc.* 111:4513–4514 (1989)) or substitution of cysteine for selenocysteine by means of an automated peptide synthesizer (Oikawa et al., *Proc. Natl. Acad. Sci. USA* 88:3057–3059 (1991)) resulted in production of proteins with altered properties. For example, this substitution in subtilisin results in conversion of this protease into an acyl-transferase (Wu and Hilbert, *J. Am. Chem. Soc.* 111:4513–4514 (1989)).

The invention further relates to methods of measuring the responsiveness of a cell to thyroid hormone and characterizing thyroid-cell containing tissue, and kits useful for detecting 5' deiodinase. Such methods and kits are useful for determining whether a malignant thyroid tumor has spread to other tissue and for the diagnosis of thyroid cancer.

BRIEF DESCRIPTION OF THE FIGURES

FIG. 1 illustrates the DNA sequence and predicted amino acid sequence of rat liver Type I iodothyronine 5' deiodinase.

Lanes 1-6: total RNA from kidney, liver, spleen, heart, lung and small intestine.

Lane 7: poly(A)+ RNA from thyroid of methimazole-treated rats.

Lane 8: poly(A)+ RNA from rat kidney.

Lanes 9 and 10: poly(A)+ RNA from pituitary and brown adipose tissue.

FIG. 3 illustrates the effect of thyroid states on Type I iodothyronine 5' deiodinase mRNA levels. Liver and kidney poly(A)+ RNA from hypothyroid (−), euthyroid (Eu) and hyperthyroid (+) rats were probed with G21 cRNA.

Figure 4A:
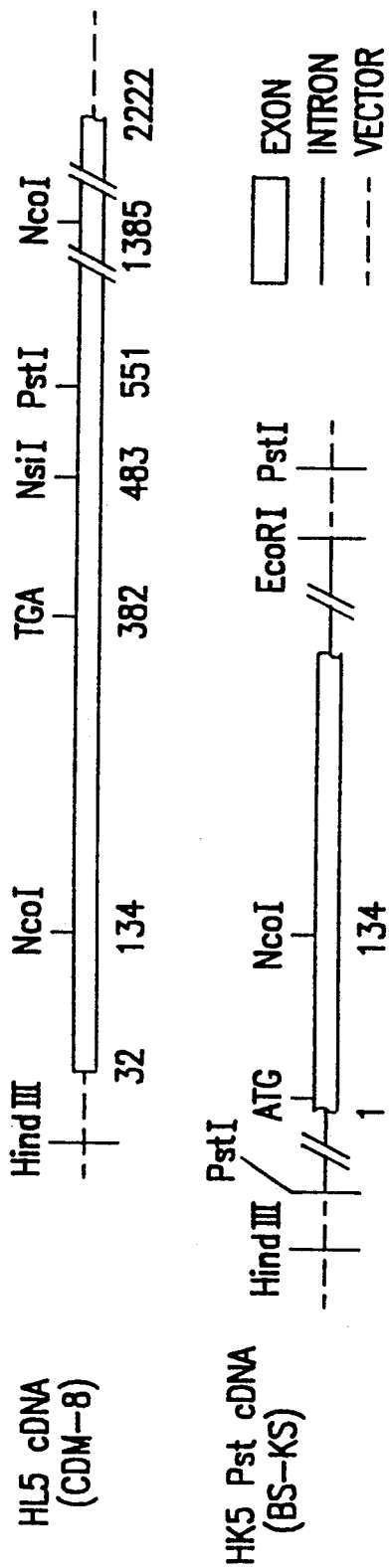

FIG. 4A illustrates partial restriction maps of the human liver and kidney clones. Relevant restriction sites are shown at the corresponding nucleotide position of the cDNA and the vector. The TGA codon is also indicated. The curved line indicates that the exact border of the exonic sequence is not known.

FIG. 4B depicts the DNA and predicted amino acid sequence of the human Type I 5'-deiodinase. Nucleotides are numbered as described in the text. The amino acid selenocysteine is noted as SeC.

FIG. 5 illustrates the DNA sequence comparison between the human and rat Type I 5'deiodinase coding regions. Only the nucleotides of the rat cDNA that differ from those of the human are shown. Both the ATG initiation codon and the TGA codon encoding selenocysteine are marked with asterices. Nucleotide 32, the 5' end of the human liver clone is marked with a #. The rat coding sequence is 24 nucleotides longer than that of the human protein.

Figure 6:
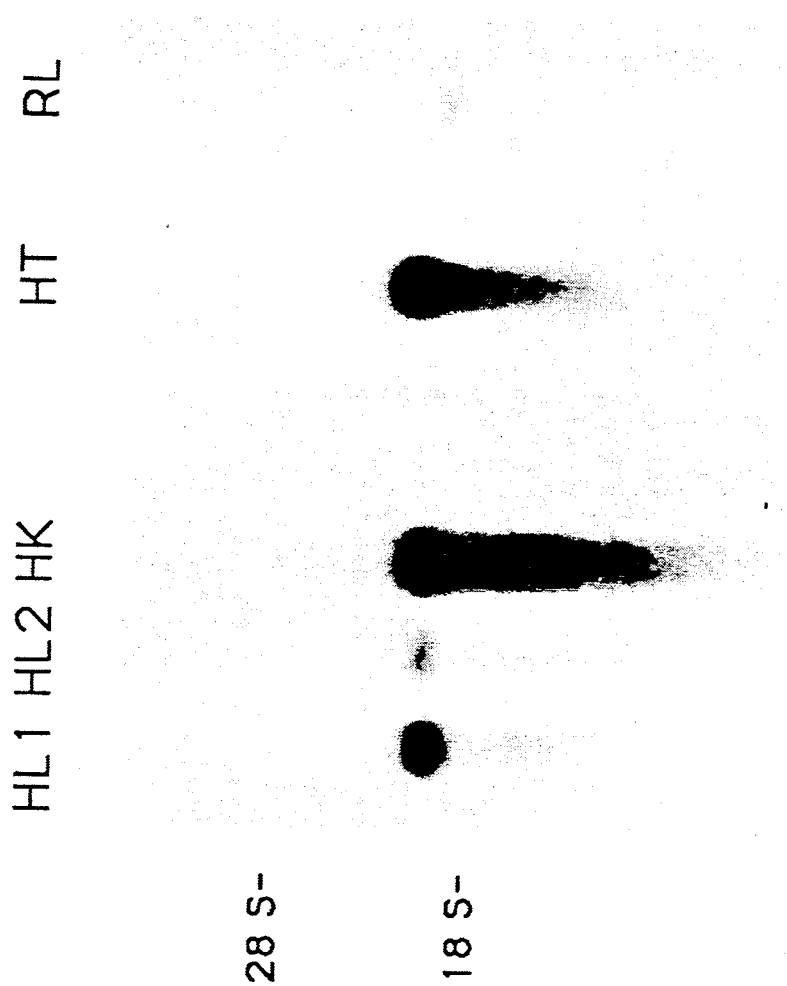

FIG. 6 is a Northern Blot analysis of Type I 5'-deiodinase mRNA. Poly(A)+RNA was isolated from human liver (HL1, HL2), kidney (HK), and thyroid (HT), and from hyperthyroid rat liver (RL) as described in Example IX. Each lane contains 2 ug of the indicated sample.

Figure 7:
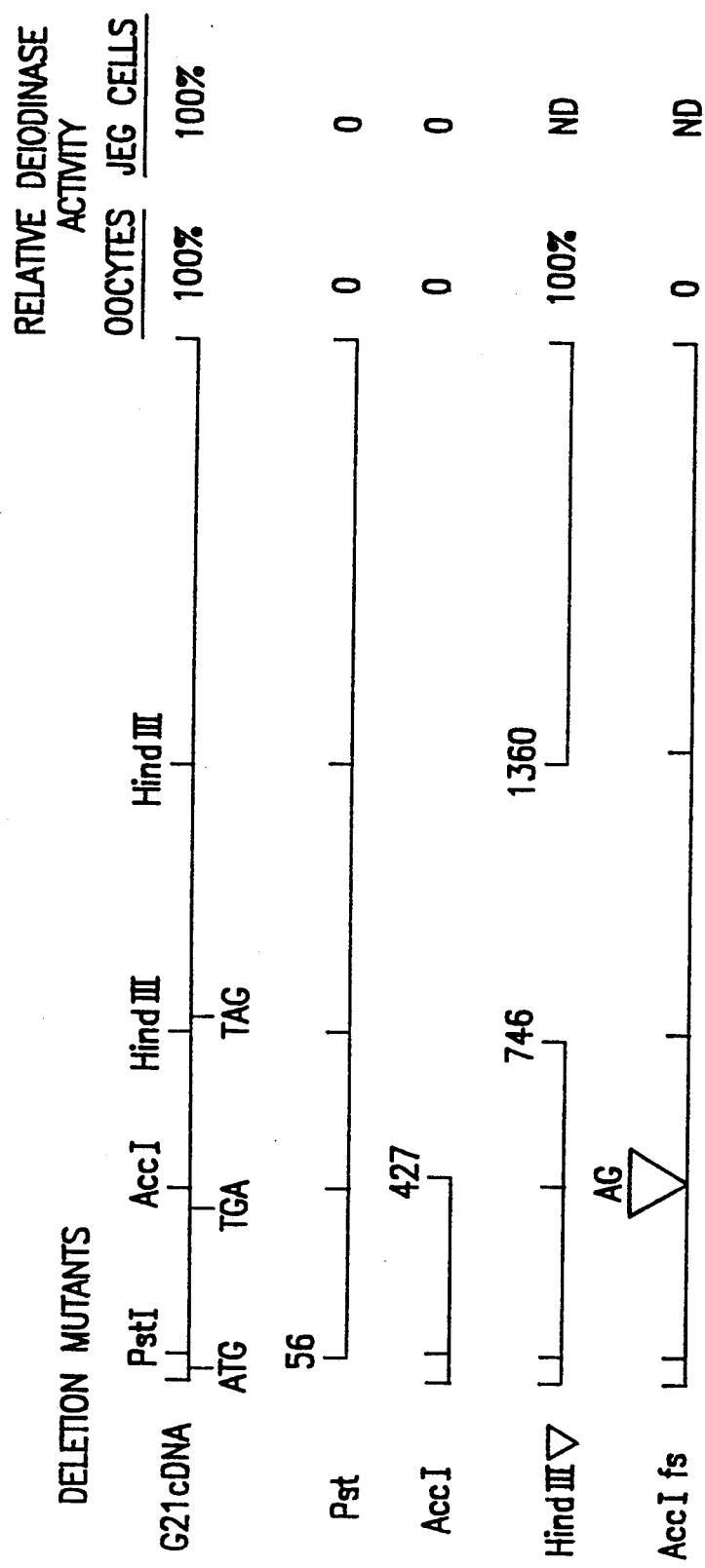

FIG. 7 illustrates the expression of Type I iodothyronine 5' deiodinase from G21 wild-type and deletion constructs, in oocytes and JEG cells.

FIG. 8 illustrates the expression of Type I iodothyronine 5' deiodinase from G21 wild-type and mutant constructs, in oocytes.

Figure 9:
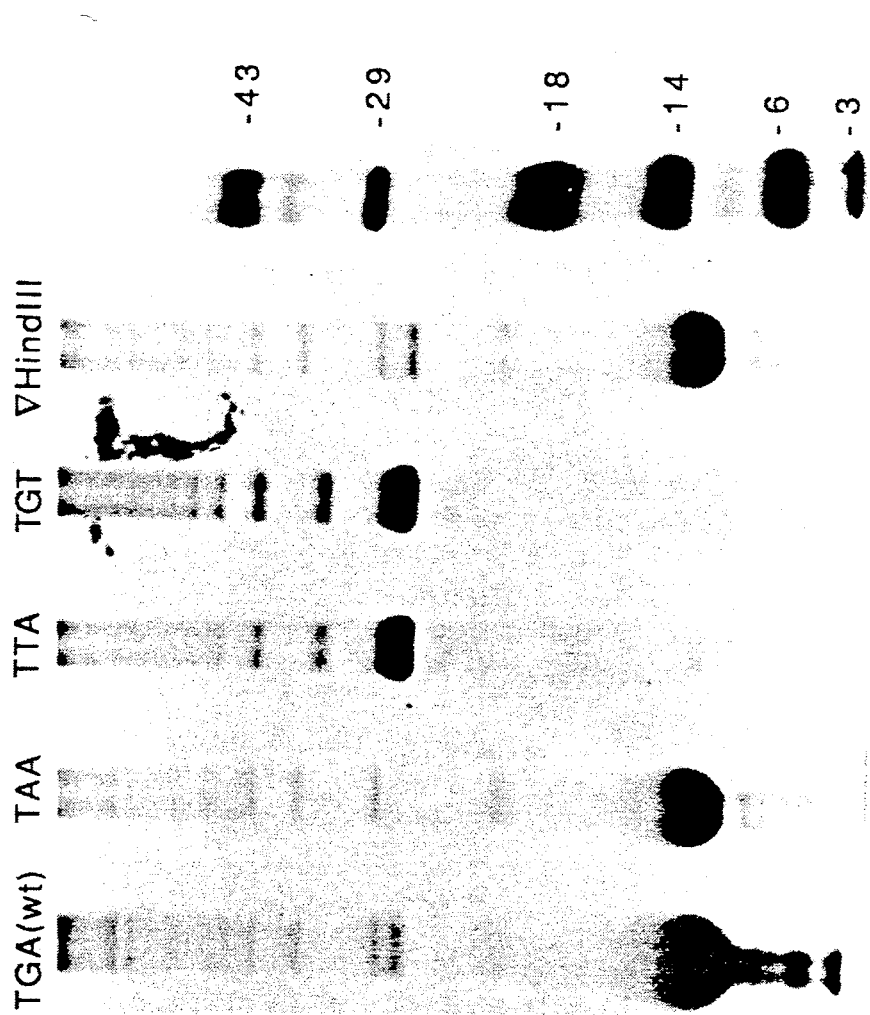

FIG. 9 is an illustration of a polyacrylamide gel analysis of in vitro translation products of clone G21, substitution mutants and the HindIII internal deletion. In vitro transcribed RNA was translated in rabbit reticulocyte lysate using $^{35}S$ methionine.

Figure 10:
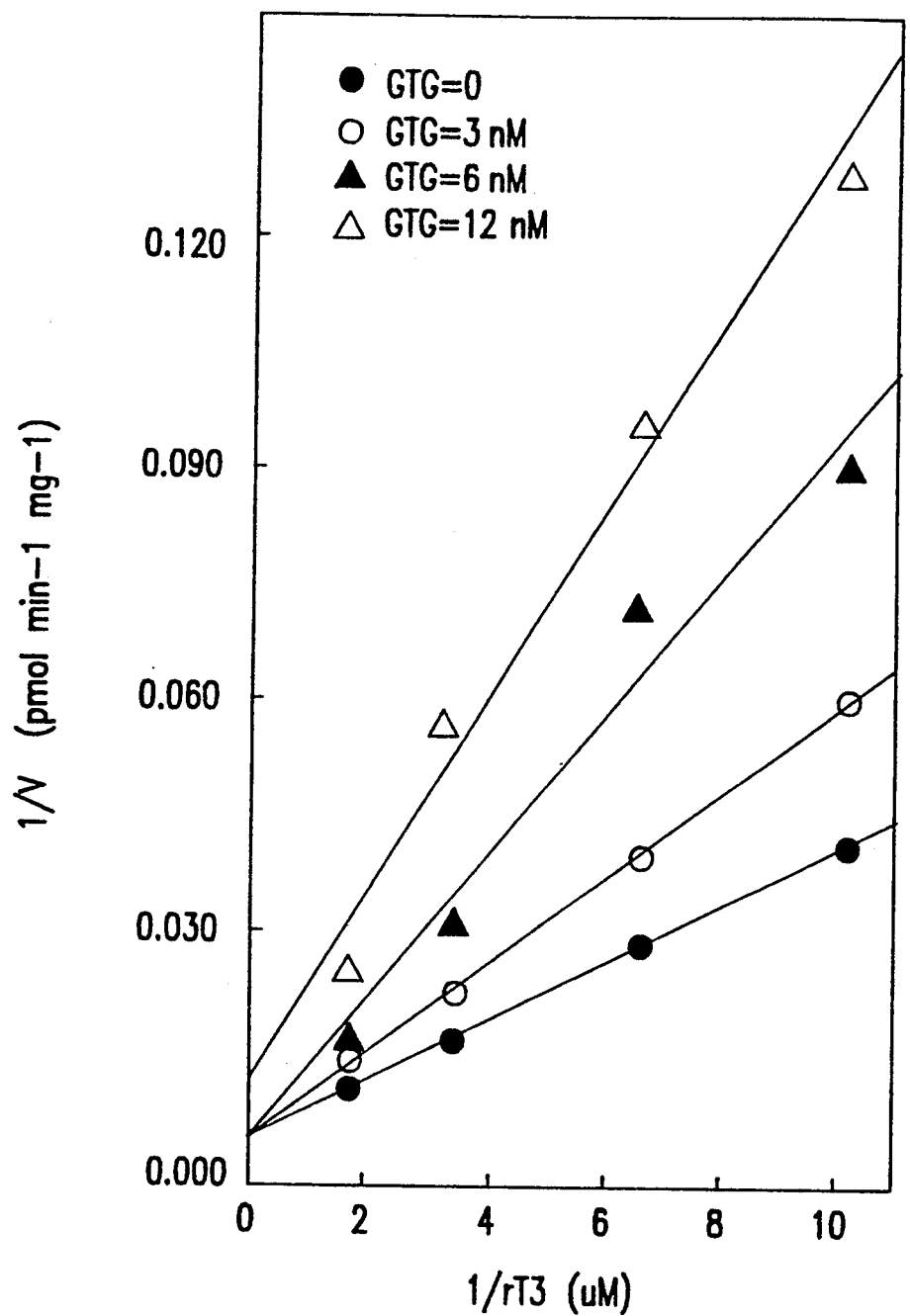

FIG. 10 illustrates the kinetics of inhibition of $rT_3$ deiodination by gold thioglucose (GTG). Double-reciprocal plots of deiodination rate vs. $rT_3$ concentration at varying GTG concentrations are shown. Reaction conditions were as described in example IX.

Figure 11:
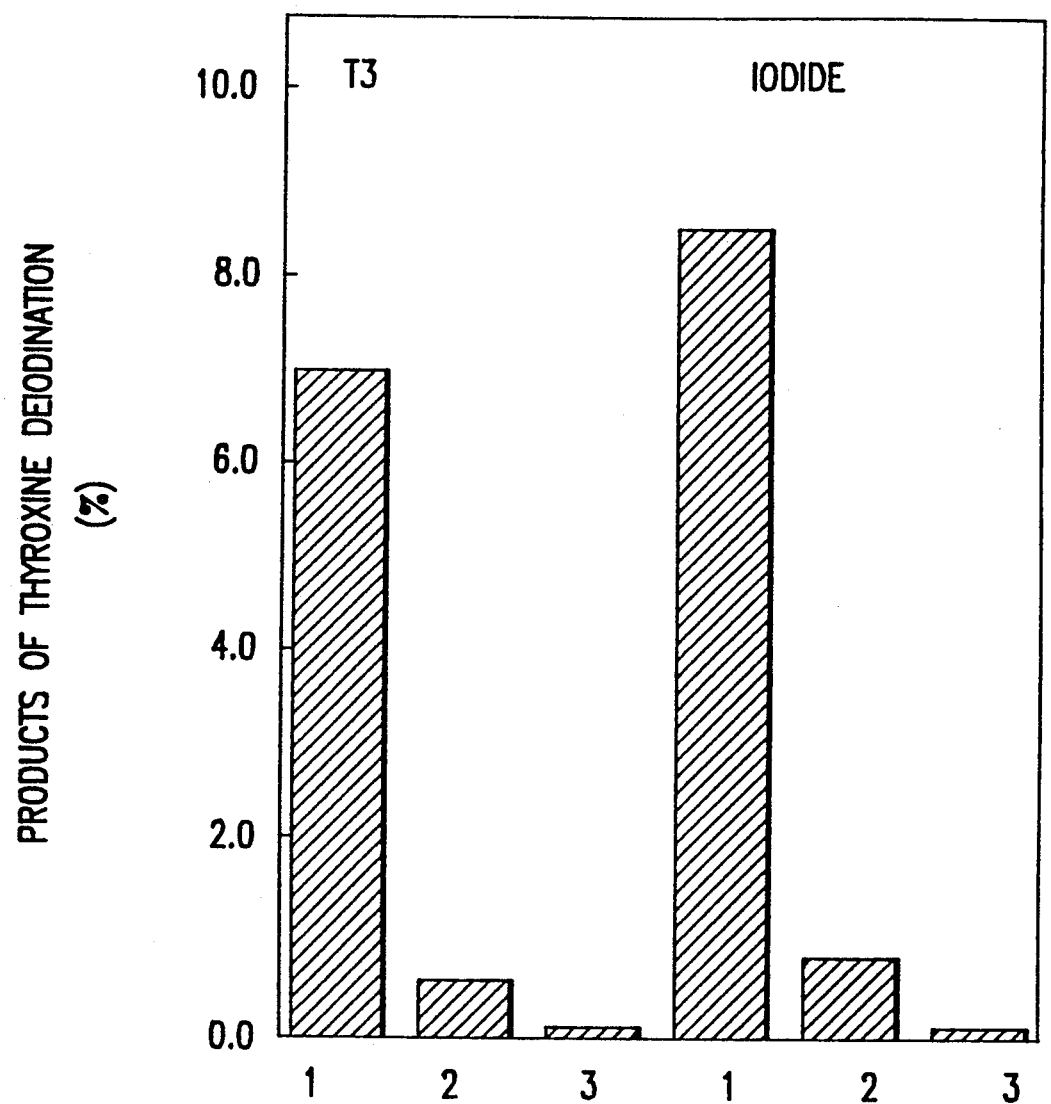

FIG. 11 illustrates the inhibition of $T_4$ to $T_3$ deiodination. The products of $T_4$ deiodination, $T_3$ and I, are shown as percent of total $T_4$ present under the various conditions. Reactions were performed as described in Example IX.

Figure 12:
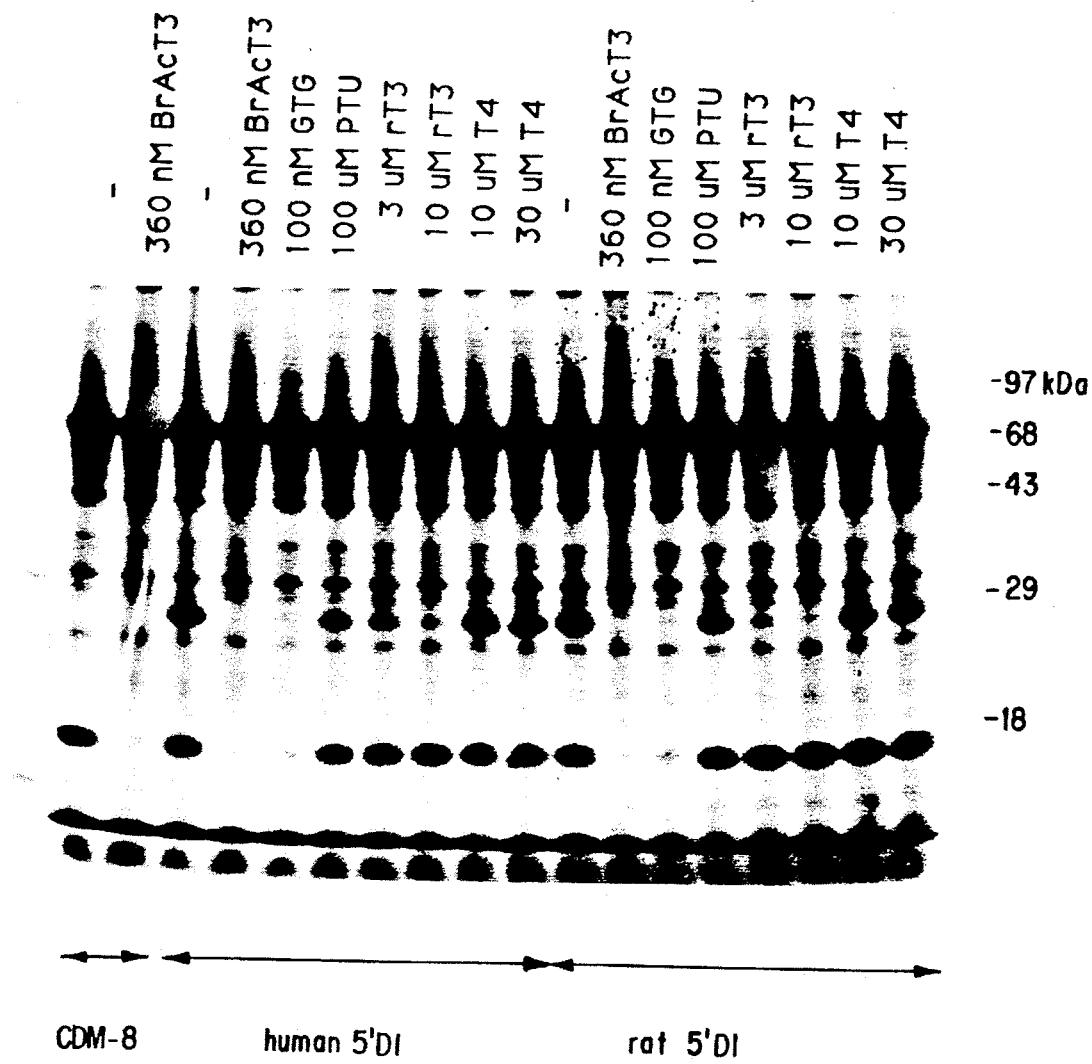

FIG. 12 illustrates bromoacetyl affinity labeling of human and rat transiently expressed 5'-deiodinases. Transfection with CDM-8 vector alone or vector containing the human and rat 5' DI cDNA is indicated under the corresponding lane. Concentrations of the various added competitors are shown.

Figure 13A:
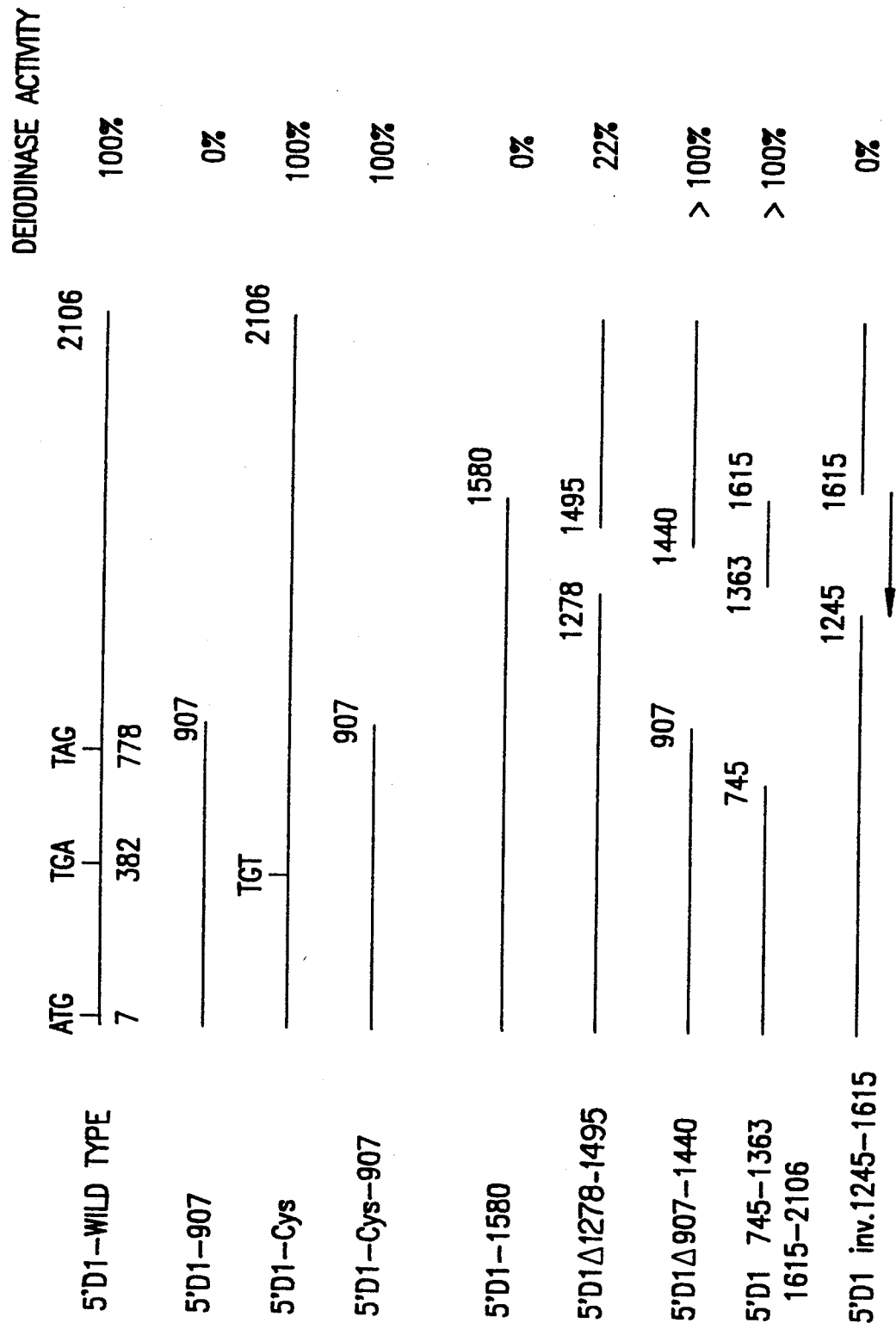

FIG. 13A is an illustration of deletion and inversion mutations of rat 5' deiodinase cDNA 3' untranslated region. Wild-type and mutant rat 5' deiodinase constructs were assayed for production of 5' deiodinase activity following transient transfection in JEG-3 or COS-7 cells. Deiodinase activity at the level of the wild-type rat 5' deiodinase construct is defined as 100%, and was equivalent to 5' deiodination of 2 pmol reverse $T_3$/min/mg protein for TGA-containing constructions and 1 pmol reverse $T_3$/min/mg protein for TGT-containing constructs, in JEG cell extracts.

Figure 13B:
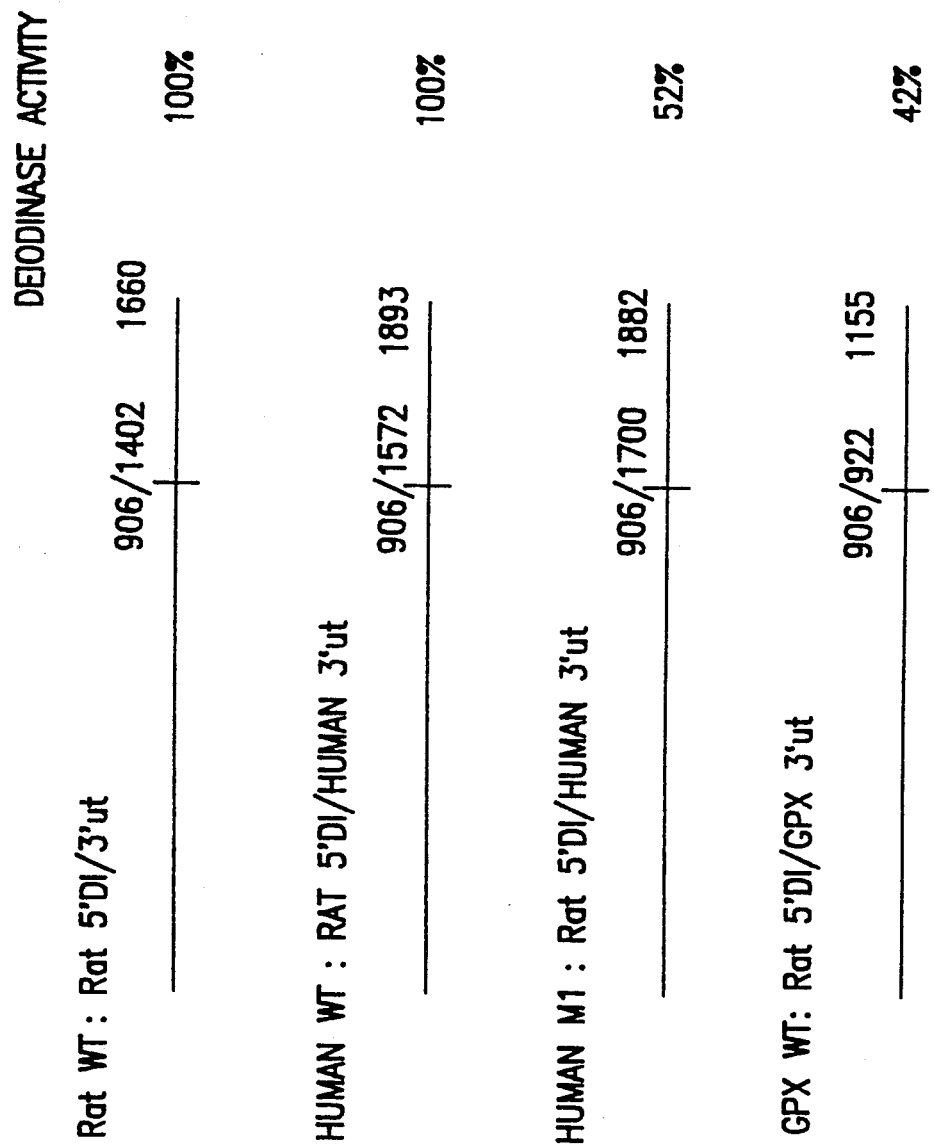

FIG. 13B is an illustration of rat 5' deiodinase constructs containing 3' untranslated sequences from rat or human 5' deiodinase or rat GPX cDNAs. Constructs containing either rat or human 5' deiodinase or rat GPX 3'ut sequences adjacent to rat 5' deiodinase coding sequences were assayed for production of 5' deiodinase activity as above.

Figure 14:
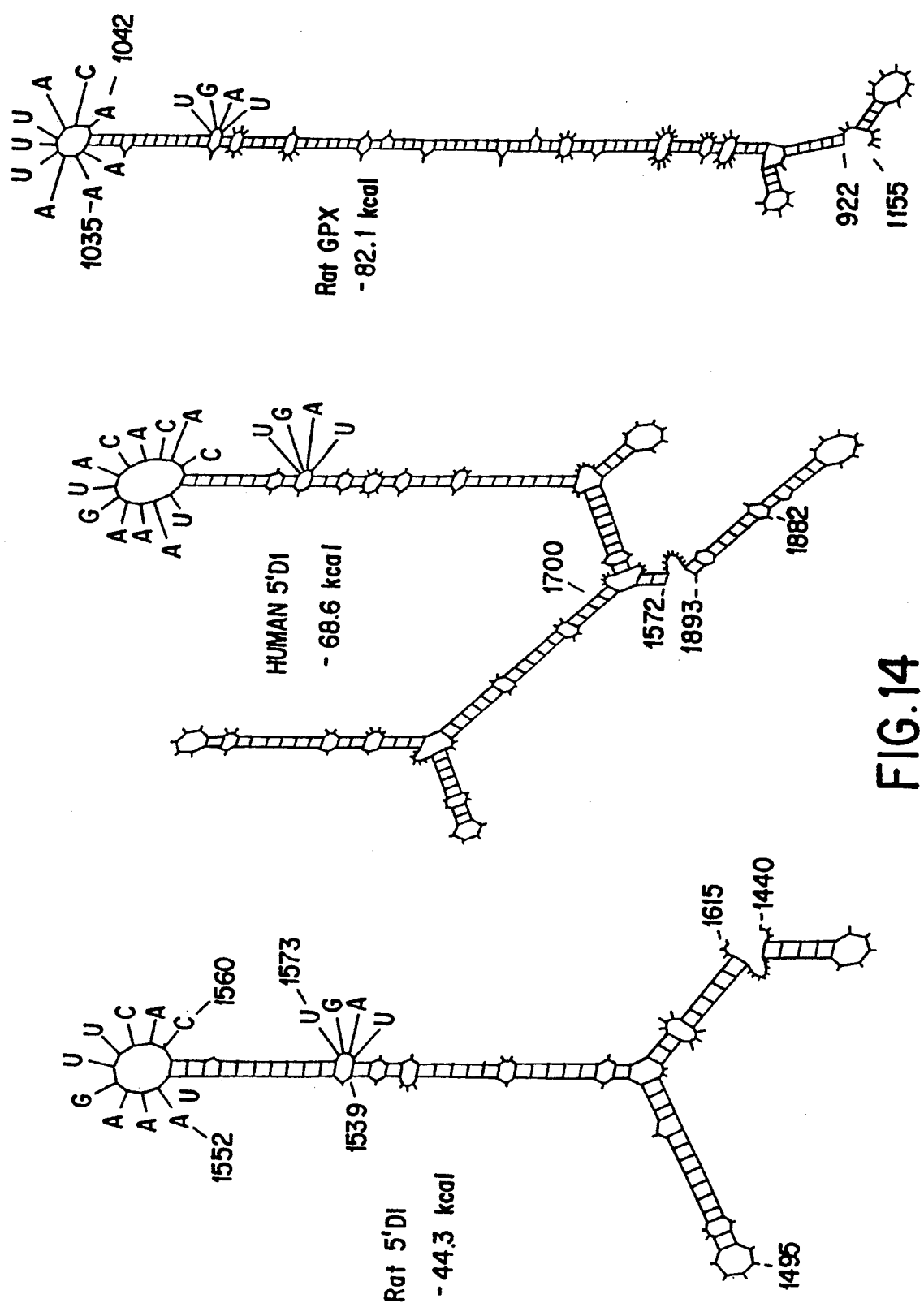

FIG. 14 is an illustration of predicted secondary structures in the 3' untranslated regions of selenocysteine-encoding RNAs. Sequences from the 3' untranslated regions of the rat 5' deiodinase, human 5' deiodinase and rat GPX (Ho et al., *J. Nucl. Acids Res.* 16:5207 (1988)) are shown. The positions of deletions which resulted in partial or complete loss of function are indicated. Structure analysis was performed using the FOLD program of the Univ. of Wisconsin Genetics Computer Group (UWGCG) software (Devereux et al., *Nucl. Acids Res.* 122:387-395 (1984)).

FIG. 15 is an illustration of deletion mutations in the stem-loop regions of rat 5' deiodinase and GPX mRNAs. PCR deletions were generated as described in PRC protocols (Higuchi, R. "Recombinant PCR, in *PCR Protocols,* Innis M. A., Gelfand D. H. Sninsky J. J., White T. J., eds. Academic Press, 177-183 (1990), and cloned into the vector fragment described in Example VIIA. Deiodinase assays were performed as described in Example VIIA.

FIG. 16 is an illustration of sequence similarities in the stem-loop regions of the rat and human 5' deiodinase, and mammalian GPX cDNAs. Analysis was performed using the LINEUP program of the UWGCG software (Devereux et al., *Nucl. Acids Res.* 12:387-395 (1984)). Nucleotide numbers are shown in parentheses.

FIG. 17, Seq. ID No. 3, illustrates the DNA sequence of the human selenocysteine insertion sequence, 5' deiodinase cDNA from nucleotide 1572 to 1893 (corresponding to nucleotides 1-322 of Seq. ID No. 3).

FIG. 18, Seq. ID No. 4, illustrates the DNA sequence of rat GPX cDNA from nucleotide 922 to 1155 (corresponding to nucleotides 1-234 of Seq. ID No. 4).

DETAILED DESCRIPTION OF THE INVENTION

Background

Although thyroxine ($T_4$) is the principal secretory product of the vertebrate thyroid, all of the essential metabolic and developmental effects of this hormone are mediated by 3,3',5-triiodothyronine ($T_3$) produced from the hormone by 5' deiodination. The Type I iodothyronine 5'-deiodinase, a thiol-requiring, propylthiouracil (PTU)-sensitive oxidoreductase, is present in greatest concentration in liver and kidney and provides most of the circulating $T_3$ (Larsen et al., *Endocr. Rev.*, 2:87-102 (1981)). Type I iodothyronine 5' deiodinase has eluded many attempts in purification.

A 2.1 kb cDNA for this deiodinase has now been isolated from a rat liver cDNA library by expression cloning in the Xenopus oocyte. The kinetic properties of the protein expressed in transient assay systems, the tissue distribution of the mRNA, and its changes with thyroid status confirm its identity.

The cDNA for rat deiodinase was then used to probe human cDNA libraries for the analogous human gene. Human cRNA hybridizes to a 2.4 kb mRNA in human liver, kidney and thyroid. The gene for human Type I iodothyrinone-5'-deiodinase was constructed from human liver and kidney cDNAs. This gene was expressed in COS-7 cells and its kinetic properties were studied.

An important discovery related to this invention is the finding that the mRNA for 5' deiodinase contains a UGA codon for selenocysteine, an amino acid which is required for maximum enzyme activity. This discovery provides the explanation for the recent observation that conversion of $T_4$ to $T_3$ is impaired in experimental selenium deficiency (Beckett et al., *Biochem. J.*, 248:443-447 (1987); Arthur et al., *Research in Veterinary Science*, 45:122-123 (1988); Beckett et al., *Biochem. J.*, 259:887-892 (1989); Arthur et al., *Inorganic Biochem.*, 39:101-108 (1990); Arthur et al., *Clin. Chem. Enzymol. Comm.* 3:209-214 (1990)) and identifies the mechanism for the essential role of this trace element in thyroid hormone action.

Incorporation of selenocysteine occurs cotranslationally at UGA codons, normally read as stop codons, in several bacterial proteins (Zinoni et al., *Proc. Natl. Acad. Sci. USA* 83:4650-4654 (1986); Garcia et al., *J. Bacteriol.* 174:2093-2098 (1991)) and in the mammalian proteins, glutathione peroxidase (GPX) (Chambers et al., *EMBO J.* 5:1221-1227 (1986); Mullenbach et al., *Protein Eng.* 2:239-246 (1988); Takahashi et al., *J. Biochem.* 108:145-148 (1990)), selenoprotein P (Hill et al., *J. Biol. Chem.* 266:10050-10053 (1991)), and Type I iodothyronine 5' deiodinase (Berry et al., *Nature* 349:438-440 (1991). Previous analyses in bacteria have suggested that a stem-loop structure involving the UGA codon and adjacent sequences is necessary and sufficient for selenocysteine incorporation into formate dehydrogenase (FDH) and glycine reductase (Garcia et al., *J. Bacteriol.* 174:2093-2098 (1991); Zinoni et al., *Proc. Natl. Acad. Sci. USA* 87:4660-4664 (1990); Bock et al., *Molecular Microbiol.* 5:515-520 (1991)).

According to the present invention, a unidirectional, size-fractionated rat liver cDNA library for expression screening in *Xenopus oocytes* was constructed. Plasmid DNA was transcribed in vitro, the resulting RNA injected into oocytes, and oocyte homogenates assayed for deiodination of 3,3',5'-triiodothyronine ("reverse" $T_3$; $rT_3$). This strategy resulted in isolation of a single positive clone, G21. The DNA sequence and predicted amino acid sequence of rat liver Type I 5' deiodinase clone G21 are shown in FIG. 1.

To verify that this clone encoded the Type I 5' deiodinase, it was expressed in JEG-3 human choriocarcinoma cells following DNA transfection. The 2.1 kb insert was excised from Bluescript, inserted into the mammalian expression vector CDM-8 (Aruffo et al., *Proc. Natl. Acad. Sci. U.S.A.* 84:8573-8577 (1987)), and the resulting construct transfected into JEG-3 cells by the $Ca_3(PO_4)_2$ method (Brent et al., *Molec. Endo* 3:1996-2004). Two days following transfection, cell homogenates or microsonmal fractions were assayed for Type I 5' deiodinase activity using $rT_3$ as substrate (Berry et al., *Molec. Endo.* 4:743-748 (1990)).

The Km for $rT_3$ was 130 nM in the presence of 5 mM dithiothreitol (DTT). There was no diodinase activity in cells transfected with CDM-8 vector alone. PTU was a competitive inhibitor of DTT, with greater than 50% inhibition by 0.5 $\mu$M PTU. $T_4$ was a competitive inhibitor of $rT_3$ deiodination, and was converted to $T_3$ by microsomal protein from transfected, but not control, cells.

Figure 2:
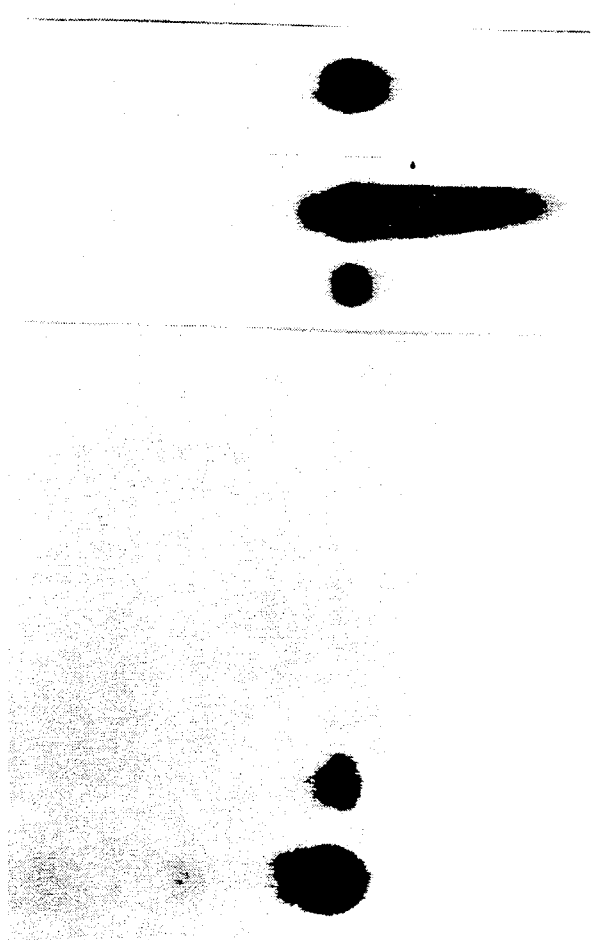
FIG. 2 illustrates a Northern blot analysis of Type I iodothyronine 5' deiodinase mRNA in rat tissues.

G21 cRNA hybridized to a single band of ~2 kb in mRNA from thyroid, kidney, liver, and pituitary, but not in mRNA from spleen, heart, lung, small intestine, or brown fat (FIG. 2). This tissue distribution is in agreement with previous studies using enzyme assays in tissue homogenates (Leonard et al., *Biochemistry of Deiodination. In: Thyroid Hormone Metabolism* (Hennemann, G., ed.) 189-229 (1986)).

Alterations in the quantity of deiodinase mRNA in rat liver parallel changes in Type I deiodinase activity and the thyroid status of the animal, being reduced in hypothroid animals and increased in hyperthyroid animals (Berry et al., *Molec. Endo.* 4:743-748 (1990)). Northern blots confirm that the G21 cRNA hybridizing 2 kb band also changes in parallel with thyroid status (FIG. 3).

Also according to the present invention, a portion of the rat CDNA encoding Type I 5'-deiodinase (nucleotides 1 to 745 of FIG. 1) was used to screen human liver and kidney cDNA libraries for human Type I 5'-deiodinase. Initial screening of human liver library in the CDM-8 vector yielded a 2188 base pair clone with a 5' boundary corresponding to nucleotide 32 of the rat sequence (FIG. 1). A 417 base pair Nco I to Pst I fragment of this liver cDNA (nucleotides 134 to 551) was then used to screen a human kidney cDNA library in λ-gt 10 vector. This method successfully isolated the remainder of the human gene. A single cDNA of 2222 nucleotides was then constructed from the liver and kidney cDNAs that encoded the entire gene based on the partial restriction map of FIG. 4A. The sequence of human 5'-deiodinase is shown in FIG. 4B.

FIG. 5 is a DNA sequence comparison between the human and rat Type I 5'-deiodinase coding regions. The coding regions are 82% homologous. The putative amino acid sequences are 88% identical.

To establish that the cDNA encodes a functional 5'-deiodinase, it was transiently expressed in COS-7 cells, which contain no endogenous iodinase. The transiently expressed enzyme was identified by its capacity to deiodinate $rT_3$ in a saturable fashion.

FIG. 6 shows that human cRNA hybridizes to a 2.4 kb mRNA in human liver, kidney and thyroid. This mRNA is approximately 200 nucleotides longer than the rat liver 5'-deiodinase, which is shown for comparison on the same blot.

Identification of 5' Deiodinase as a Selenocystein-containing Enzyme

The DNA sequence of clone G21 predicts a protein of ~14 kD, initiating at nucleotide 7 and terminating at nucleotide 382 (TGA, a known termination codon). Deletions from the 5' or 3' ends, an internal deletion, and frameshift insertion were constructed to identify regions essential for deiodinase activity. The locations of these mutations and their effects on activity in both oocytes and transfected JEG cells are shown in FIG. 7.

The absence of activity with the Pst I 5' deletion confirmed that sequences 5' to nucleotide 56 are required for production of active enzyme, indicating that the ATG at position 7 is indeed the initiation codon.

The absence of deiodinase activity using the Acc I 3' deletion indicates a requirement for sequences beyond nucleotide 427, and thus beyond the putative stop codon (TGA).

The absence of activity with the Acc I frameshift construct indicates that sequences beyond nucleotide 427 must be in frame, and therefore are likely to be coding. The Hind III internal deletion construct was fully active, indicating that the sequences between nucleotides 746 and 1360 are not required for deiodinase activity.

To confirm the surprising result that sequences beyond the putative stop codon (UGA) were required for expression of active deiodinase, the protein products of the Type I deiodinase clone were analyzed by in vitro transcription as described above followed by in vitro translation in wheat germ and rabbit reticulocyte lysates in the presence of $^{35}S$ methionine.

In the wheat germ system a major labelled protein of approximately 14 kD was produced, corresponding to termination at the UGA condon at nucleotide 382. However, in the reticulocyte lysate, $^{35}S$ methionine labelled both a ~14 kD protein and, to a lesser extent, a ~27 kD protein. These results could be explained if the UGA codon at nucleotide 382 encodes the rare amino acid, selenocysteine, and the full length protein terminates at the UAG codon at nucleotide 778.

Translation of UGA as selenocysteine has been reported for the mammalian glutathione peroxidase gene (Chambers et al., *EMBO* 5:1221-1227 (1986); Mullenbach et al.,*Protein Engineering* 2:239-247 (1988)) and several bacterial genes (Zinoni et al., *Proc. Natl. Acad. Sci. USA* 83:4650-4654 (1986); Menon et al., *J. Bacteriol* 169:5401-5407 (1987); Ishida et al., *Nucleic Acids Res.* 15:10051 (1987)). The absence of a 27 kD protein in wheat germ lysate could be explained by the previous report that selenocysteine tRNA$_{UGA}$ is absent in the plant kingdom (Lee et al., *Molec. Cell. Biol.* 10:1940-1949 (1990)).

To verify that the UGA codon at position 382 encodes selnocysteine, the corresponding TGA was converted to either the stop codon, TAA, the leucine codon, TTA, or the cysteine codon, TGT, by oligonucleotide directed mutagenesis. In vitro synthesized mRNAs from these constructs were assayed for expression of Type I 5' deiodinase in oocytes (FIG. 8) and translated with $^{35}S$ methionine in vitro in reticulocyte lysates (FIG. 9).

Conversion of the TGA codon to either a stop codon or a leucine codon resulted in complete loss of deiodinase activity, while conversion to a cysteine codon resulted in activity of approximately 10% of the wild type G21 level. Clone G21 mRNA produced proteins of ~14 kD and ~27 kD, in close agreement with the 29 kD size predicted by the open reading frame. This construct encodes a protein six amino acids shorter than wild type, deleting the last ten amino acids and substituting four amino acids.

The results implicate the trace element selenium as the nucleophilic atom in the active site of the Type I iodothyronine 5' deiodinase. This is analogous to the selenocysteine in the active site of mammalian glutathione peroxidase (Forstrom et al., *Biochemistry* 17:2639-2644 (1978)), the only previously identified eukaryotic selenocysteine-containing enzyme.

Table 1 demonstrates another similarity to glutathione peroxidase, sensitivity to inhibition by gold, which is believed to complex with the selenolate group in the active site of this enzyme (Chaudiere et al., *J. Inorganic Biochem.* 20:313-325 (1984)).The activity of the transiently expressed wild type deiodinase protein is inhibited ~50% by 10 nM gold thioglucose (GTG). Substitution of cysteine for selenocysteine resulted in an enzyme with ~20% of the intrinsic activity of the wild type protein, in agreement with the oocyte studies. This mutant protein was much less sensitive to inhibition by GTG than the native enzyme.

A UGA codon is also present at position 382 of the human 5'-deiodinase sequence—the same site as in the rat sequence. As is the case with the rat 5'-deiodinase, deiodination is inhibited by gold thioglucose with an apparent Ki of 4.7 nM (FIG. 10). The enzyme also catalyzes $T_4$ to $T_3$ conversion by a PTU-sensitive mechanism with the production of equimolar quantities of $T_3$ and I, albeit at a much slower rate (FIG. 11).

Bromoacetyl (BrAcT$_3$) labeling of the human and rat transiently expressed deiodinase was performed to establish that the in vitro expressed protein was of the size predicted by the deduced amino acid sequence presuming that the UGA encodes selnocysteine. In cells transfected with the CDM-8 vector alone (FIG. 12, lanes 1 and 2), several discrete labeled bands are present (64, 46, 34, and 16 kDa). Labeling of the 16 kDa band is completely, and that of the 64 and 46 kDa bands partially, blocked by excess unlabeled BrAcT$_3$. Transfection with the vector containing the human (lanes 3-10) or rat (lanes 11-18) cDNA produced a protein of ~28 kDa which labeled with BrAcT$_3$ (FIG. 12). A protein this size is consistent with what would be expected if the UGA stop codon encodes selenocysteine.

Both the Type I deiodinase and glutathione peroxidase exhibit ping-pong kinetics using reduced thiols as cosubstrate and are sensitive to inhibition by carboxymethylation (Leonard et al., *Biochemistry of Deiodination. In: Thyroid Hormone Metabolism* (Hennemann, G., ed.) 189-229 (1986); Forstrom et al., *Biochemistry* 17:2639-2644 (1978); Visser et al., *Molec. and Cell. Endo.* 33:321-327 (1983); Visser et al., *Molec. and Cell. Endo.* 33:321-327 (1983)).

No significant homology was found between Type I iodothyronine 5' iodothyronine 5' deiodinase and glutathione peroxidase. Furthermore, 5' deiodinase was not significantly homologous to any other protein sequence in GenBank or EMBL. (Devereux et al., *Nucleic Acids. Res.* 12:387-395 (1984)). This includes protein disulfide isomerase, another thiol-requiring protein which has been speculated to be related to the Type I deiodinase (Boada et al., *Biochem. Biophys. Res. Commun.* 155:1297-1304 (1988).

The lack of relationship between type I deiodinase and protein disulfide iosmerase was further demonstrated by the following experiments. First, no Type I deiodinase activity was detected in oocytes injected with PDI mRNA. Secondly, PDI cRNA hybridized to a 2.8 kb mRNa present in total poly(A)+ RNA from liver and to the 2.2-3.2 kb fraction. The PDI cRNA was not detectable in the 3.2-4.6 kb fraction or the 1.7-2.2 kb fraction. In contrast, the Type I deiodinase mRNA falls within the 1.9-2.4 kb region of the rat liver poly- (A)+RNA. (Berry, M. J. et al., *Mol. Endocrin.* 4:;743-748 (1990)).

Requirement of a 3' Untranslated Sequence for Recognition of TGA as a Selenocystein Codon According to this invention, the mechanism which allows the eukaryotic cell to incorporate the amino acid selenocysteine into a protein, as opposed to terminating translation at the UGA codon, has been elucidated for the first time. The requirement for successful translation of the active deiodinase protein in Xenoplus oocytes and in transfected JEG cells have also been analyzed. For successful translation of this protein, sequences between about nucleotide 1360 and 1615 in the 3'-untranslated region of the cDNA must be present, with sequences between 1440 and 1615 being essential.

These roughly 200-255 nucleotides can be inserted immediately 3' of the coding sequences and retain the ability to induce the translation of completely active enzyme. However, if these nucleotides are removed or if the sequence is inverted, there is no expression of the active enzyme.

Characterization of the 3' Untranslated Sequence

UGA is recognized as a selenocysteine codon rather than a stop codon due to the presence of a segment of about 200-255 nucleotides, with 200 nucleotides being essential, of a 3' untranslated sequence. This segment is located greater than a kilobase downstream from the UGA codon.

The present inventors have surprisingly discovered that the mechanism by which this recognition occurs involves a stem-loop structure in the 3' untranslated region of the mRNA.

5' deiodinase was used to investigate selenoprotein synthesis in eukaryotes. The present inventors have discovered that successful incorporation of selenocysteine into this enzyme requires a specific 3' untranslated segment of about 200 nucleotides, which is found in both rat and human 5' deiodinase mRNAs. These sequences are not required for expression of a cysteine-mutant deiodinase. While little primary sequence similarity exists between the 3' untranslated regions of these mRNAs and those encoding GPX, the 3' untranslated sequences of rat GPX can substitute for the 5' deiodinase sequences in directing selenocysteine-insertion. Computer analyses predict similar stem-loop structures in the 3' untranslated regions of the 5' deiodinase and GPX mRNAs. Limited mutations in these structures reduce or eliminate their capacity to permit 5' deiodinase translation. These results identify a "selenocysteine-insertion sequence (SECIS)" motif in the 3' untranslated region of these mRNAs that is essential for successful translation of 5' deiodinase, GPX, and possible other eukaryotic selenocysteine-containing proteins.

The human deiodinase gene contains a similar SECIS motif at nucleotides 1573 to 1894 of FIG. 4. Comparison of the 321 nucleotide sequence with the corresponding rat sequence shows a 66% homology.

Mutant Sequences of Iodothyronine 5' deiodinase.

Mutant sequences of 5' deiodinase, including for example the cysteine-126 mutant and wild-type sequences of 5' deiodinase, are useful as "reporter" genes for monitoring transfection efficiencies or in the study of heterologous promoter function in transient expression assays. Cysteine-126 is useful as an internal control for transfection efficiency in DNA transfer studies.

The present cysteine-126 mutant is described in *Nature* 349:438-440 (Jan. 31, 1991). This paper is hereby incorporated by reference.

Presently, there is a great need for internal controls for use in the study of expression by transfection techniques. This need is due to the fact that DNA uptake by cells can vary from plate to plate. Thus, the amount of given signal can vary either because of intended or artificial variations. The present internal control, including for example, mutant sequences such as cysteine-126, can be used to correct for such variations. The expression of cysteine mutant (G-5) is proportional to DNA input into the transfection system (see Example VIII, Table II). The assay for the cysteine-126 mutant is easy to do, is exquisitely sensitive, is low cost, and utilizes radioactive iodine. The rate of removal of $^{125}I$ from the 3' or 5' position of reverse 3,3',5'-triiodothyronine is measured as a measure of the activity of the enzyme coded for by the mutant cysteine-126 sequence.

Internal control suitable for use in the present invention include, for example, cysteine-126 and functional equivalents thereof. A functional equivalent of cysteine-126 is also a mutant of iodoothyronine 5' deiodinase wherein the mutant is readily expressed by a number of different cell lines, is easy to measure accurately with a minimum of manipulation of cell extracts or medium.

Again, reporter genes can be used to assess the function of various heterologous promoters or to determine the transfection efficiency of plasmids introduced into cells by various DNA transfer techniques.

To use the cys-126 mutant enzyme (G-5) to determine the activity of other promoters one incorporates the G5 deiodinase construct 3' to the start site of transcription of a given promoter. Such studies are described in *Gene* 1672:107-111 (Apr. 22, 1986) and *Molecular and Cellular Biology* 6(9):3173-3179 (Sep. 1986); both of which are hereby incorporated by reference. *Gene* describes the construction of a chloramphenicol acetyl transferase vector (CAT) and *Mol. and Cell. Bio.* describes a human growth hormone gene, for performing such studies.

Use of Reporter Genes

A plasmid can be constructed, using known techniques, in which the cDNA coding for the reporter enzyme is cloned into a plasmid in which either incorporates a constitutive promoter (for example, TK) or a poly cloning sequence 5' to the reporter enzyme sequence. In the case of a constitutive promoter, the plasmid is used as an internal control. In the case of a poly cloning site either immediately upstream of the reporter knee or upstream of an amputated heterologous promoter such as TK, such a plasmid is used to study the influence of various DNA sequences of interest on the expression of the reporter gene.

An advantage of using deiodinase as a reporter gene is that the assay for deiodinase uses a readily available, low-cost substrate which can be labeled with $^{125}I$ to extremely high specific activity. Thus, only a small amount of cell sonicate is necessary to obtain a signal, for example, about 1-2 $\mu l$ of cell sonicate. Use of the cysteine-126 mutant, that is, substitution of cysteine for selenocysteine in 5' deiodinase, removes the requirement that a cell have the appropriate selenocysteine-insertion machinery. Thus, there is a board repertoire of cells which can be subjected to this technique.

Selection of cell lines suitable for expressing transfected mutant is performed by $Ca_3(PO_4)_2$ mediated transfection of the cysteine-mutant DNA according to standard procedures and incubation of the cells overnight, followed by DMSO treatment the next day (Larsen et al., *J. Biol. Chem.* 261:14373-14376 (1986); Brent et al., *J. Biol. Chem.* 264:178-182 (1989); Berry et al., *J. Biol. Chem.* 266:14155-14158 (1991). Two days after transfection, cells are harvested by scraping, and sonicated. Expression of the cysteine mutant is assayed by quantitation of 5' deiodinase catalyzed by the cell sonicates, as described previously (Berry et al., *J. Biol. Chem.* 266:14155-14158 (1991)). Using this procedure, one can screen large numbers of cell lines at the same time. Transfection of 20 different cell lines can easily be performed one day 1 (2 hours), followed by DMSO-treatment on day 2 (2hours), and assay on day 3 (4 hours). The cells to be tested are transfected with either the cys mutant (G-5) or wild-type (G-21) construct directed by the CMV promoter together with TKGH (or TKCAT) plasmid (see Table II). The latter, TK-directed, reporter genes allows ascertainment that successful transfection of DNA has occurred. Cells which expressed deiodinase activity after transfection with either G-5 or G-21 are those which possess the appropriate selenocysteine insertion machinery. Cells which express deiodinase after transfection with G-5, but not with G-21, are those which can synthesize deiodinase but which are unable to incorporate selenocysteine into the wild-type protein. Cells which do not express deiodinase from either construct and yet have been successfully transfected (i.e., showing suitable expression of CAT of hGH) are cells in which the cell is not capable of synthesizing the deiodinase protein at all.

Cell lines that express transfected cysteine mutant include, for example, COS-7 cells and the JEG choriocarinoma cell lines. These cell lines will express transfected cysteine mutant, under the influence of the cytomegalovirus (CMV) promoter in the plasmid CDM8. Other suitable cell lines can be readily determined by routine experimentation by one of ordinary skill in the art.

A study comparing the kinetics of the wild-type enzyme containing selenocysteine and the cysteine mutant is described in the *Journal of Biological Chemistry* 226:14155-14158 (1991), and is hereby incorporated by reference.

Reporter genes are also used to evaluate whether cells are capable of successfully translating selenocysteine-containing proteins. This is accomplished using mutant clones (for example, cysteine-126) and wild-type selenocysteine clones. The level of deiodinase produced by the cysteine mutant is compared to the level of deiodinase produced by cells in which the gene containing the wild-type selenocysteine enzyme has been introduced. A higher ratio of selenocysteine to cysteine activity indicates a more efficient, better, selenocysteine-insertion mechanism.

In summary, a novel mechanism by which selenocysteine is encoded by a codon that serves as a termination signal is provided. Furthermore, the gene encoding the second of the now two known mammalian selenocysteine-containing proteins (5' deiodinase) has been cloned and sequenced. The preferred embodiments of this invention are fully discussed herein.

Description of the Preferred Embodiments

I. Introduction

As used herein, the term "5' deiodinase" includes the Type I iodothyronine 5' deiodinase molecule. The term "5' deiodinase" additionally includes the functional derivatives of such molecules. The term "5' deiodinase" additionally includes both glycosylated and unglycosylated forms of any of the above-described molecules.

As used herein, a "functional derivative" of 5' deiodinase is a compound which possesses a biological activity that is substantially similar to the biological activity of 5' deiodinase. The term "functional derivatives" is intended to include the "fragments," "variants," "analogs," or "chemical derivatives" of 5' deiodinase. The term "fragment" is meant to refer to any polypeptide subset of 5' deiodinase. The term "variant" is meant to refer to a molecule substantially similar in structure and function to either the entire 5' deiodinase molecule, or to a fragment thereof.

A molecule is said to be "substantially similar" to 5' deiodinase if both molecules have substantially similar structures or if both molecules possess a similar biological activity. Thus, provided that two molecules possess a similar activity, they are considered variants as that term is used herein even if the structure of one of the molecules is not found in the other, or if the sequences of amino acid residues are not identical.

The term "analog" is meant to refer to a protein that differs structurally from the wild type enzyme 5' deiodinase, but possesses biological activity that is substantially similar to that of 5' deiodinase.

As used herein, the term "DNA segment" refers to a sequence of DNA having the characteristics described for the segment. In particular, as used herein the term "DNA segment" denotes an untranslated DNA sequence located 3' to the rat cDNA sequence encoding Type I iodothyronine 5' deiodinase.

As used herein, the terminology "stem-loop structure" denotes a stem loop structure located in the 3' untranslated region of mRNA of a selenocysteine containing protein which allows a UGA codon to be recognized as a selenocysteine codon rather than a UGA stop codon. Suitable structures include, for example, specific sequences located in the 3' untranslated region of the wild-type selenocysteine containing construct, for example, the sequence located between nucleotides 1440 and 1615 in the wild-type 5' deiodinase construct; and functional equivalents thereof. A functional equivalent is defined as a stem-loop structure which allows a UGA codon to be recognized as a selenocysteine codon and not a stop codon.

As used herein the terminology "selenocysteine-insertion sequence" (SECIS), denotes a motif in the 3' untranslated region of mRNAs, including for example 5' deiodinase and GPX mRNAs, having a stem-loop structure in the 3' untranslated region of the mRNA, that is essential for successful translation of 5' deiodinase, GPX, and other eukaryotic selenocysteine-containing proteins.

The terminology "reporter gene" is meant to refer to both mutant sequences of iodothyronine 5' deiodonese, including for example cysteine-126, and wild-type sequences of 5' deiodinase, which can be used for monitoring transfection efficiencies or in the study of heterologous promoter function in transient expression assays.

A plasmid is said to be an "internal control" if the plasmid is such that cDNA coding for a reporter enzyme is cloned into a plasmid having incorporated therein a constitutive promoter, including for example TK. Internal controls are useful when studying expression by transfection, to account for variations in DNA uptake by cells.

II. Cloning of the Gene Coding for Type I Iodothyronine 5' Deiodinase

The present invention relates in part to the cloning of the gene which encodes Type I iodothyronine 5' deiodinase).

A first step for obtaining a gene sequence which encodes the rat 5' deiodinase comprises obtaining DNA from cells which contain such gene sequences. This DNA is used to prepare a genomic library. Alternatively, cDNA is obtained using cells expressing 5' deiodinase and a cDNA library is prepared. Techniques for preparing such libraries are disclosed by Maniatis, et al. (In: *Molecular Cloning, A Laboratory Manual*, Cold Spring Harbor Laboratories, Cold Spring Harbor, N.Y. (1982)). A cDNA library can be conveniently prepared using rat liver poly(A)+ RNA.

To identify and isolate the desired gene sequence, the above-described library is then screened for gene sequences which hybridize to a probe sequence of either the entire rat liver 5' deiodinase encoding sequence, a sequence complementary to such 5' deiodinase-encoding sequence, or a fragment of either of such sequence. Thus, for example, to isolate a DNA molecule which is capable of encoding a human 5' deiodinase, human 5' deiodinase expressing cells are used to produce a DNA (or cDNA) library. The members of this library are screened for their ability to hybridize with the above-described rat 5' deiodinase probe sequence using techniques, such as those disclosed by Maniatis, et al. (In: *Molecular Cloning A Laboratory Manual*, Cold Spring Harbor Laboratories, Cold Spring Harbor, N.Y. (1982)), or by Haymes, et al. (In: *Nucleic Acid Hybridization, A Practical Approach*, IRL Press, Washington, D.C. (1985)).

A preferred method for preparing the desired sequence is to obtain a 1.9 to 2.4 kb fraction of rat liver poly(A)+ RNA using the methods described in Berry, et al., *Molec Endo.* 4:743–748 (1990), and St. Germain, et al., *J. Biol. Chem.* 264:3054–3056 (1989). Briefly, the poly(A)+ RNA was injected into *Xenopus oocytes*. Plasmid DNA from the resulting cDNA was transcribed in vito, the resulting RNA injected into oocytes, and oocyte homogenates assayed for deiodination of 3,3',5'-triiodothyronine. This strategy resulted in isolation of a clone designated G21.

The DNA probe for identifying and isolating DNA encoding 5' deiodinase may be labeled with a detectable group. Such detectable group can be any material having a detectable physical or chemical property. Such materials have been well-developed in the field of immunoassays and in general most any label useful in such methods can be applied to the present invention. Particularly useful are enzymatically active groups, such as enzymes (see *Clin. Chem.* 22:1243 (1976)); enzyme substrates (see British Pat. Spec. 1,548,741); coenzymes (see U.S. Pat. Nos. 4,230,797 and 4,238,565); enzyme inhibitors (see U.S. Pat. No. 4,134,792); fluorescers (see *Clin. Chem.* 25:353 (1979)); chromophores; luminescers (such as chemiluminescers and bioluminescers (see *Clin. Chem.* 25:512 (1979))); specifically bindable ligands; proximal interacting pairs; and radioisotopes.

Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, beta-galactosidase, alkaline phosphatase and peroxidase.

As is generally known to those of ordinary skill, hybridization of the probe to the DNA sequences of the library may be accomplished under a variety of conditions of stringency so as to permit either a stable hybrid to form only between two gene sequences which have very similar sequences (high stringency) or to permit such a hybrid to form between two gene sequences having more divergent sequences (low stringency). Conditions of high stringency employ high temperatures (such as 50°–65° C.) and high concentrations of agents such as formamide (for example 50% formamide). Conditions of low stringency employ lower temperatures (approximately 42° C.) and lower concentrations of agents such as formamide (for example 20–40% formamide) ((Lawler, et al., *Bone Marrow Transpl.* 3:473 (1988); Bhattacharya, et al., *Ind. J. Med. Res.* 87:144 (1988); Arif, et al., *Virus Res.* 2:85 (1985); Smith, et al., *Virol.* 123:393 (1982); Priestly, et al., *Histochem.* 89:467 (1988); Rohrmann, et al., *J. Gen. Virol.* 62:137 (1982). When employing hybridization conditions of 42° C. and 20% formamide, two gene sequences having approximately 10% homology can form a stable hybrid (Rohrmann, et al., *J. Gen. Virol.* 62:137 (1982)).

Once members of the library have been identified which are capable of hybridizing to the probe, it is necessary to determine whether they encode 5' deiodinase (or a fragment thereof). Such characterization may be performed in any of several ways. Preferably, the gene sequence can be introduced into a suitable host cell, expressed, and the expressed protein tested for its ability to deiodinate 3,3',5'-triiodothyronine (rT$_3$). A gene sequence which expresses a protein that is capable of catalyzing this reaction encodes 5' deiodinase. Alternatively, the expressed molecule can be tested for its ability to bind to antibody (prepared as described below) that is reactive with 5' deiodinase.

In the event that the expressed molecule is unable to catalyze deiodination of rT$_3$, it may be concluded that the isolated sequence encodes only a fragment of the desired gene sequence. Accordingly, the isolated gene sequence is used to identify and isolate any missing fragments of the desired gene sequence (Bender, et al., *J. Supramolec. Struc.* 10(suppl):32 (1979); Chinault, et al., *Gene* 5:111 (1979); Clarke, et al., *Nature* 287:504 (1980)). Once any such sequences have been identified and isolated, it is possible to construct a single gene sequence which is capable of encoding the entire desired enzyme using well known methods of recombinant DNA technology.

In order to achieve expression of 5' deiodinase having the activity of the native enzyme, the expressed enzyme should possess at least one selenocysteine residue(s), preferably at site 126. Selenocysteine is encoded by the codon UGA, which generally functions as a termination codon (the "opal" codon).

According to the invention, incorporation of selenocysteine at the appropriate UGA-encoded site requires that a 3' untranslated segment of DNA be operably linked to the 5' deiodinase-encoding region. In the cDNA for 5' deiodinase, this DNA segment is found between nucleotides 1360 and 1615, more essentially between nucleotides 1440 and 1615, of the 3' untranslated region, and is approximately 200-255 nucleotides in length, more essentially 200 nucleotides in length. The approximately 200-255 nucleotide segment can also be inserted immediately 3' to the 5' deiodinase coding region to achieve expression of the active enzyme. In the absence of this nucleotide segment, UGA is recognized as a termination signal, resulting in expression of an incomplete and inactive form of 5' deiodinase.

The invention is also related to 5' deiodinase enzymes which retain activity but differ from the native enzyme by at least one amino acid. Amino acid sequence variants of 5' deiodinase can be prepared by mutations in the DNA. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these variants ordinarily are prepared by site-directed mutagenesis of nucleotides in the DNA encoding the 5' deiodinase molecule, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed 5' deiodinase variants screened for the optimal combination of desired activity. Techniques for making substitution mutations at predetermined sites in DNA having a known sequence are well known, for example, site-specific mutagenesis.

Preparation of a 5' deiodinase variant in accordance herewith is preferably achieved by site-specific mutagenesis of DNA that encodes an earlier prepared variant or a nonvariant version of the protein. Site-specific mutagenesis allows the production of 5' deiodinase molecule variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987) may be employed to obtain single-stranded DNA.

In general, site-directed mutagenesis can be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells such as JEG-3 cells, and clones are selected that include recombinant vectors bearing the mutated sequence arrangement.

Other mutagenesis methods are also available. See, for example, Smith, M., *Ann. Rev. Genet.* 19:423 (1985); Section IV, Chapters 17-21 of *Methods in Enzymology* 154:329-414 (1987); Hutchison, et al., *J. Biol. Chem.* 253:6551 (1978).

A preferred mutagenesis method is that developed by Promega Corporation, 2800 Woods Hollow Road, Madison, Wis. 53711, employing the pSELECT TM-1vector system. One of skill will choose an appropriate system for use.

The above-disclosed mutagenesis techniques can be used to obtain DNA encoding a modified protein having at least one selenocysteine residue, wherein the wild-type protein does not contain selenocysteine. This is accomplished by substituting a TGA codon for one or more codons of the structural gene for the protein, at a position in the gene corresponding to the desired amino acid substitution site in the protein.

After the desired clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxylterminal fusions of from one residue to polypeptides of essentially unrestricted length, as well as intrasequence insertions of single or multiple amino acid residues. Intrasequence insertions (i.e., insertions within the complete 5' deiodinase molecule sequence) may range generally from about 1 to 10 residues, more preferably 1 to 5 residues. An example of a terminal insertion includes a fusion of a signal sequence, whether heterologous or homologous to the host cell, to the N-terminus of the 5' deiodinase molecule to facilitate the secretion of mature 5' deiodinase molecule from recombinant hosts.

The third group of variants are those in which at least one amino acid residue in the 5' deiodinase molecule, and preferably, only one, has been removed and a different residue inserted in its place.

Most deletions and insertions, and substitutions in particular, are not expected to produce radical changes in the characteristics of the 5' deiodinase molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native 5' deiodinase molecule-encoding nucleic acid, expression of the variant nucleic acid in recombinant cell culture, and, optionally, purification from the cell culture, for example, by immunoaffinity adsorption on a polyclonal anti-5' deiodinase molecule column (to adsorb the variant by binding it to at least one remaining immune epitope).

The activity of the cell lysate or purified 5' deiodinase molecule variant is then screened in a suitable screening assay for the desired characteristic. For example, a change in the immunological character of the 5' deiodinase molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

III. Expression of 5' Deiodinase

DNA or cDNA molecules which encode 5' deiodinase can be operably linked to an expression vector and introduced into a host cell to enable the expression of the 5' deiodinase molecule by that cell. Two DNA sequences (such as a promoter region sequence and a desired 5' deiodinase molecule encoding sequence) are said to be operably linked if the nature of the linkage between the two DNA sequences does not (1) result in the introduction of a frame-shift mutation, (2) interfere with the ability of the promoter region sequence to direct the transcription of the desired 5' deiodinase molecule encoding gene sequence, or (3) interfere with the ability of the desired 5' deiodinase molecule gene sequence to be transcribed by the promoter region sequence. For optimum expression of active 5' deiodinase, the DNA or cDNA molecule is preferably operably linked to a 3' untranslated region necessary for the incorporation of selenocysteine at the appropriate UGA codon site.

A DNA sequence encoding a 5' deiodinase molecule may be recombined with vector DNA in accordance with conventional techniques, including blunt-ended or stagger-ended termini for ligation, restriction digestion to provide appropriate termini, filling in of cohesive ends as appropriate, alkaline phosphatase treatment to avoid undesirable joining, and ligation with appropriate ligases.

The present invention encompasses the expression of 5' deiodinase in either prokaryotic or eukaryotic cells. Preferred eukaryotic hosts include yeast (especially Saccharomyces), or mammalian cells (such as, for example, human or primate cells).

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells such as JEG-3 human choriocarcinoma cells, and their derivatives. Liver, kidney or pituitary cell lines may also be suitable host cells. For a mammalian host, several possible vector systems are available for the expression of the desired protein molecule. A wide variety of transcriptional and translational regulatory sequences may be employed, depending upon the nature of the host. The transcriptional and translation regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabilite.

The expression of 5' deiodinase in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer, et al. *J. Mol. Appl. Gen.* 1:273–288 (1982)); the TK promoter of Herpes virus (McKnight, S., *Cell* 31:355-365 (1982)); the SV40 early promoter (Benoist, et al., *Nature* (London) 290:304-310 (1981); the yeast gal4 gene promoter (Johnston, et al., *Proc. Natl. Acad. Sci. (USA)* 79:6971–6975 (1982); Silver, et al. *Proc. Natl. Acad. Sci. (USA)* 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the 5' deiodinase molecule does not contain any intervening codons which are capable of encoding a methionine (i.e., AUG). The presence of such codons results either in the formation of a fusion protein (if the AUG codon is in the same reading frame as the desired protein molecule encoding DNA sequence) or a frame-shift mutation (if the AUG codon is not in the same reading frame as the desired protein molecule encoding sequence). It is also preferable to ensure that the vector system contains the 3'-untranslated region necessary for incorporation of selenocysteine into the polypeptide at a site corresponding to the appropriate UGA codon site in the 5' deiodinase-coding region.

The expression of 5' deiodinase can also be accomplished in procaryotic cells. Preferred prokaryotic hosts include bacteria such as *E. coli*, Bacillus, Streptomyces, Pseudomonas, Salmonella, Serratia, etc. The most preferred prokaryotic host in *E. coli*. Bacterial hosts of particular interest include *E. coli* K12 strain 294 (ATCC 31446). *E. coli* X1776 (ATCC 31537), *E. coli* W3110

(F−, lambda−, prototrophic (ATCC 27325)), and other enterobacteria (such as *Salmonella typhimurium* or *Serratia marcescens*), and various Pseudomonas species. The prokaryotic host must be compatible with the replicon and control sequences in the expression plasmid.

To express 5' deiodinase in a prokaryotic cell (such as, for example, *E. coli*, *B. subtilis*, Pseudomonas, Streptomyces, etc.), it is necessary to operably link the 5' deiodinase encoding sequence to a functional prokaryotic promoter. Such promoters may be either constitutive or, more preferably, regulatable (i.e., inducible or derepressible). Examples of constitutive promoters include the int promoter of bacteriophase λ, and the bla promoter of the β-lactamase gene of pBR322.

Examples of inducible prokaryotic promoters include the major right and left promoters of bacteriophase λ ($P_L$ and $P_R$), the trp, recA, lacZ, lacI, gal, and tac promoters of *E. coli*, the α-amylase (Ulmanen, et al., *J. Bacteriol.* 162:176-182 (1985)), the σ-28-specific promoters of *B. subtilis* (Gilman, et al., *Gene* 32:11-20 (1984)), the promoters of the bacteriophages of Bacillus (Gryezan, T. J., In: *The Molecular Biology of the Bacilli*, Academic Press, Inc., N.Y. (1982)), and Streptomyces promoters (Ward, et al., *Mol. Gen. Genet.* 203:468-478 (1986)). Prokaryotic promoters are reviewed by Glick, B. R., (*J. Ind. Microbiol.* 1:277-282 (1987)); Cenatiempo, Y. (*Biochimie* 68:505-516 (1986)); and Gottesman, S. (*Ann. Rev. Genet.* 18:415-442 (1984)).

Proper expression in a prokaryotic cell also requires the presence of a ribosome binding site upstream from the gene-encoding sequence. Such ribosome binding sites are disclosed, for example, by Gold, et al. (*Ann. Rev. Microbiol.* 35:365-404 (1981)).

The 5' deiodinase encoding sequence, including the 3'-untranslated region and an operably linked promoter, may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired protein molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu2, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can be utilized. Examples of such expression vectors include the yeast 2-micron circle, the expression plasmids YEP13, YCP and YRP, etc., or their derivatives. Such plasmids are well known in the art (Botstein, et al., *Miami Wntr. Symp.* 19:265-274 (1982); Broach, J. R., In: *The Molecular Biology of the Yeast Saccharomyces: Life Cycle and Inheritance*, Cold Spring Harbor Laboratory, Cold Spring Harbor N.Y. p. 445-470 (1981): Broach, J. R., *Cell* 28:203-204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others. For achieving the expression of mammalian 5' deiodinase, the preferred expression vector is the CDM-8 mammalian expression vector (Aruffo et al., *Proc. Natl. Acad. Sci. USA* 84:8573-8577 (1987)).

Preferred prokaryotic vectors include plasmids such as those capable of replication in *E. coli* such as, for example, pBR322, ColE1, pSC101, pACYC 184, πVX. Such plasmids are, for example, disclosed by Maniatis, et al. (In: *Molecular Cloning, A Laboratory Manual*, Cold Spring Harbor Press, Cold Spring Harbor, N.Y. (1982)). Bacillus plasmids include PC194, pC221, pT127, etc. Such plasmids are disclosed by Gryczan, T. (In: *The Molecular Biology of the Bacilli*, Academic Press, N.Y. (1982), pp. 307-329). Suitable Streptomyces plasmids include pIJ101 (Kendall, et al., *J. Bacteriol.* 169:4177-4183 (1987)), and Streptomyces bacteriophages such as φC31 (Chater, et al., In: *Sixth International Symposium on Actinomycetales Biology*, Akademiai Kaido, Budapest, Hungary (1986), pp. 45-54). Pseudomonas plasmids are reviewed by John, et al. (*Rev. Infect. Dis.* 8:693-704 (1986)), and Izaki, K. (*Jpn. J. Bacteriol.* 33:729-742 (1978)).

Once the vector or DNA sequence containing the constructs has been prepared for expression, the DNA constructs may be introduced into an appropriate host. Various techniques may be employed, such as protoplast fusion, calcium phosphate precipitation, electroporation or other conventional techniques. After the fusion, the cells are grown in media and screened for appropriate activities. Expression of the sequence results in the production of the protein molecule.

The 5' deiodinase molecules of the invention may be isolated and purified from the above-described recombinant molecules in accordance with conventional methods, such as extraction, precipitation, chromatography, affinity chromatography, electrophoresis, or the like. Such conventional methods can yield 5' deiodinase in substantially pure form.

In order to obtain the amino acid sequence of the 5' deiodinase, the molecules in the substantially purified fractions are recovered by any suitable method. Most preferably, for example, such recovery is accomplished by affinity chromatography, followed by concentration of sample, and resolution by gel electrophoresis. The recovered molecules may then be sequenced, preferably using an automated sequenator, and the amino acid sequence of the molecule thereby determined.

Although any suitable means can be used to determine the sequence of the 5' deiodinase molecule, it is preferable to determine the sequence using the microsequencing methods of Rodriguez (*J. Chromatog.* 350:217 (1985)). Alternatively, the 5' deiodinase molecule may be purified by electrophoresis and after electroelution, cleaved by cyanogen bromide or lysyl-C endopeptidase. The fragments may then be resolved, preferably by HPLC or by tricine gels (H. Shägger et al., *Annal. Biochem.* 166:368 (1987)) followed by electroblotting and gas-phase microsequencing. The sequence of the complete molecule can then be determined and compared with that deduced from the cDNA sequence of 5' deiodinase.

The present invention lends itself readily to the preparation of "kits" containing the elements necessary to carry out the methods of the invention. Such a kit may comprise a carrier being compartmentalized to receive in close confinement therein one or more container means, such as tubes or vials. One of the container means may contain an unlabeled or detectably labeled polynucleotide sequence, such as for example the radioactively labeled DNA or RNA encoding Type I iodothyronine 5' deiodinase. The labeled polynucleotide sequence may be present in lyophilized form, or in an appropriate buffer as necessary.

One or more container means may contain one or more endonuclease enzymes to be utilized in digesting the nucleic acids from the cells or tissues under analysis. These enzymes may be present by themselves or in admixtures, in lyophilized form or in appropriate buffers. The kit may also contain in one container probe RNA for probe synthesis, in another container radiolabeled deoxyribonucleoside triphosphate, and in another container primer. In this manner the user can prepare probe cDNA.

Finally, the kit may contain all of the additional elements necessary to carry out the methods of the invention, such as buffers, media, enzymes, pipettes, plates, nucleic acids, nucleosie triphosphates, filter paper, gel materials, transfer materials, autoradiography supplies, and the like.

IV. Uses for 5' Deiodinase and the DNA Encoding Therefor

A. Anti-5' Deiodinase Antibody

The 5' deiodinase molecules of the present invention may be used to induce the formation of anti-5' deiodinase antibodies. Such antibodies may either be polyclonal or monoclonal antibodies, or antigen binding fragments of such antibodies (such as, for example, F(ab) or F(ab)$_2$ fragments).

Suitable polyclonal antibodies can be obtained by immunizing an animal with an immunogenic amount of the 5' deiodinase molecule (preferably with an adjuvant, such as Freund's adjuvant).

Alternatively, monoclonal antibodies may be prepared, such as by immunizing splenocytes with 5' deiodinase and then fusing an immunized cell with a myeloma cell (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563–681 (1981)) in order to obtain a hybridoma cell that secretes an anti-5' deiodinase antibody.

Of special interest to the present invention are antibodies which are produced in humans, or are "humanized" (i.e. non-immunogenic in a human) by recombinant or other technology such that they will not be antigenic in humans, or will be maintained in the circulating serum of a recipient for a longer period of time.

Humanized antibodies may be produced, for example by replacing an immunogenic portion of an antibody with a corresponding, but non-immunogenic portion (i.e. chimeric antibodies) (Robinson, et al., International Patent Publication PCT/US86/02269; Akira, et al., European Patent Application 184,187; Taniguchi, M. European Patent Application 171,496; Morrison, et al., European Patent Application 173,494; Neuberger, et al., PCT Application WO86/01533; Cabilly, et al., European Patent Application 2125,023; Better, et al., *Science* 240:1041–1043 (1988); Liu, et al., *Proc. Natl. Acad. Sci.* USA 84:3439–3443 (1987); Liu, et al., *J. Immunol.* 139:3521–3526 (1987); Sun, et al., *Proc. Natl. Acad. Sci. USA* 84:214–218 (1987); Nishimura, et al., *Canc. Res.* 47:999–1005 (1987); Wood, et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science,* 229:1202–1207 (1985)) and by Oi, et al., *BioTechniques* 4:214 (1986)).

Suitable "humanized" antibodies can be alternatively produced as described by Jones, et al., *Nature* 321:552–525 (1986); Verhoeyan et al., *Science* 234:1534 (1988), and Beidler, et al., *J. Immunol.* 141–4053–4060 (1988), or by the methods disclosed in U.S. Pat. Nos. 4,816,397 and 4,816,567, which references are incorporated herein by reference.

The anti-5' deiodinase antibodies of the present invention may be used for diagnostic purposes such as to measure the expression and function of a patient's 5' deiodinase. The anti-5' deiodinase antibodies can also be used in imaging in order to characterize tissue, or to define the presence and site of metastasized 5' deiodinase-expressing cells.

For diagnostic purposes, the 5' deiodinase and anti-5' deiodinase antibodies can be used in accordance with immunoassay technology. Examples of immunoassays are described by Wide at pp. 199–206 of *Radioimmune Assay Method,* edited by Kirkham and Hunter, E. & S. Livingstone, Edinburgh, 1970.

Thus, in one embodiment, 5' deiodinase molecules can be detectably labeled and incubated with a sample, and the amount of 5' deiodinase molecule bound to the sample can be ascertained. In a second embodiment, antibody to the 5' deiodinase can be used in order to create a "pseudo-sandwich immunoassay." In one such assay (a "forward" assay), a sample suspected of containing 5' deiodinase can be incubated in the presence of an immobilized anti-5' deiodinase antibody. Solubilized, detectably labeled, 5' deiodinase molecules can be added to the reaction mixture, and the amount of 5' deiodinase determined by measuring the amount of bound label.

As will be evident to those of ordinary skill, various alternative assays can also be devised. The assay may be a simple "yes/no" assay to determine whether 5' deiodinase is present or may be made quantitative by comparing the measure of labeled molecule with that obtained for a standard sample containing known quantities of 5' deiodinase.

In another type of assay, which may also be useful with the 5' deiodinase of the present invention, "simultaneous" and "reverse" assays are used. A simultaneous assay involves a single incubation step as the antibody bound to the support and labeled antibody are both added to the sample being tested at the same time. After the incubation is completed, the solid support is washed to remove the residue of fluid sample and uncomplexed labeled antibody. The presence of labeled molecules associated with the solid support is then determined as it would be in a conventional sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the simultaneous and forward assays.

The principal reagents (antibody, labeled or unlabeled 5' deiodinase molecules) can be packaged in kit form for a particular assay together with any additional components needed or desired, such as a set of standard analyte solution which mimics or covers the anticipated concentration range for the 5' deiodinase. In addition, a buffer for dilutions of reconstituted reagents or for pH adjustment may be included. For "simultaneous" and "reverse" assays, the kit may include labeled antibody, and unlabeled antibody bound to a solid support. The kit may also contain labeled Type I 5' deiodinase molecules. The various components can be packaged in the kit in solution or lyophilized form, depending upon the stability, shipping and other requirements.

Quantitation of nucleic acid molecules which encode the 5' deiodinase molecule (or a fragment thereof) can be used to determine the extent and rate of the expression of the 5' deiodinase in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

B. Identification and Use of T$_4$→T$_3$ Conversion Inhibitors

The elucidation of the amino acid sequence of Type I 5' deiodinase is useful in the development and testing of compounds that inhibit the conversion of T$_4$ to T$_3$. Such compounds have therapeutic value in the treatment of certain forms of hyperthyroidism.

Type I 5' deiodinase contains the rare amino acid selenocysteine. Compounds that bind to this amino acid and thereby cause inhibition of the enzyme would be particularly useful therapeutic agents because of their specificity towards this enzyme.

Potential inhibitory compounds can be tested for their effect on Type I 5' deiodinase by routine assay procedures. For example, a protein preparation can be obtained from a cell that normally expresses Type I 5' deiodinase or from a host cell, such as a JEG-3 cell, transfected with cDNA encoding the enzyme.

A sample of the protein preparation is incubated with $^{125}$I rT$_3$ in the presence of absence of the putative inhibitor, and $^{125}$I quantitated as described (Berry et al.; Molec. Endo. 4:743-748 (1990)). A decrease in $^{125}$I release in the presence of the compound indicates potential usefulness as an inhibitor in vivo, and appropriate animal tests can be performed to evaluate its usefulness as a therapeutic agent.

C. Expression of 5'60 Deiodinase and Other Selenocysteine-Containing Proteins

Prior to the present invention, the mechanism by which selenocysteine was co-translationally incorporated into a polypeptide, at a site encoded by the termination codon TGA, was not known. Furthermore, only one mammalian selenocysteine-containing enzyme had been previously identified (glutathione peroxidase).

It has now been determined that the enzyme Type I iodothyronine 5' deiodinase is a second mammalian selenocysteine-containing enzyme. Furthermore, substitution of selenocysteine with cysteine at site 126 reduces enzyme activity by at least 90%. Thus, selenocysteine is essential for normal activity of this enzyme.

It has been further determined that, unexpectedly, a 200-255-nucleotide segment, a 200 nucleotide segment being essential, of the 3'-untranslated region of 5' deiodinase cDNA is required for co-translational incorporation of selenocysteine at site 126. In the absence of this DNA segment, the codon for selenocysteine, TGA, serves instead as a termination codon, leading to expression of an incomplete and inactive enzyme.

By identifying the untranslated region and its role in selenocysteine incorporation, methods are now provided for determining other selenocysteine-containing enzymes and proteins which are expressed through the action of analogous or homologous untranslated regions of their respective genes.

The first step is the identification of a protein as containing at least one selenocysteine moiety. It is then preferable to identify a cell type which naturally synthesizes this protein, in order to obtain a total poly(A)+ RNA population. Initial recovery of the RNA encoding the desired protein can be enhanced if the cell or tissue is subject to manipulations to increase production of the protein. For example, Type I 5' deiodinase activity is elevated in the hyperthyroid state, and poly(A)+ RNA can be isolated from tissues of rats made hyperthyroid by treatment with injection of T$_4$. The RNA can be size-fractionated and introduced into a suitable cell for transcription. For example, rat liver poly(A)+ can conveniently be translated in *Xenopus oocytes*.

The cell homogenates, such as oocyte homogenates, are tested for the presence of the desired protein. In the case of an enzyme such as 5' deiodinase, detection can be by measuring enzymatic activity, such as deiodination of 3,3',5'-triiodothyronine in the case of 5' deiodinase. Alternatively, the protein can be detected using a binding molecule capable of specifically binding the protein. A preferred method is the use of an antibody directed against the protein. Alternatively, if the protein has a receptor function, it may be detected by its ability to bind a suitably labeled molecule which is capable of binding to the receptor.

In this manner, it is possible to construct a cDNA library for further screening in cells capable of translating the mRNA, such as *Xenopus oocytes*. After one or more clones representing the cDNA encoding the desired protein have been identified, these clones can be used to identify and locate regions of the cDNA that are important for co-translational incorporation of selenocysteine into the protein.

In a preferred method, the DNA sequence of a cDNA clone capable of directing expression of the desired protein is determined. Putative initiation and termination codons can be identified, as can restriction endonuclease sites.

The next step is the identification of sequences necessary for expression of the protein. It is preferable to construct cDNA molecules having terminal and internal deletions, as well as a frameshift mutation or insertion. The effect of these various alterations on the ability of the cDNA to express the protein is determined using a suitable cell type. The presence of expressed protein indicates that the deleted or mutated sequence was not essential for expression.

According to the present invention, this sequence of steps was successfully used to identify a 3' untranslated sequence in the cDNA, the presence of which was necessary for successful expression of the protein 5' deiodinase. The importance of a particular sequence of the cDNA for the successful translation of other selenocysteine-containing proteins can therefore be determined in a similar manner, using the steps disclosed above.

The present invention now discloses for the first time the importance of an untranslated region for selenocysteine incorporation. Prior to this invention, it was hypothesized that the flanking nucleotides of the TGA codon, or the intracellular environment, effected the co-translational incorporation of selenocysteine at a TGA-encoded site (Engelberg-Kulka, et al., *Trends in Biochem. Sci.* 13:419-421 (1988)).

It was also hypothesized that factors for the "suppression" of the TGA termination function might include (a) the cell type or species; (b) bases adjacent to the UGA; and (c) steric interactions between the suppressor tRNA and a tRNA binding the adjacent codon (Mullenbach, et al., *Protein Engineering* 2:239-246 (1988)).

The present invention further provides methods and genetic constructs for achieving expression of a selenocysteine-containing protein such as 5' deiodinase. Expression of most mammalian proteins can be accomplished by the transfection of a suitable host cell with DNA consisting of the structural gene for the protein, operably linked to a suitable promoter region and, optionally, a region encoding a secretion signal. Such methods are described above in detail.

Surprisingly, such a construct would not achieve the expression of active 5' deiodinase. It is now disclosed that the genetic construct should additionally contain a 200-255 nucleotide 3' untranslated region, with a 200 nucleotide sequence being essential, having the sequence of nucleotides 1360-1615 of FIG. 1, with nucleotides 1440-1615 being essential, or a functional equivalent thereof. The approximately 200-255 nucleotide unstranslated segment can be located 1-582 nucleotides from the 3' end of the structural gene for 5' deiodinase. Successful expression can equally be accomplished by locating the approximately 200-255 nucleotide untranslated segment immediately 3' to the structural gene.

D. Introduction of Selenocysteine Into a Non-Selenocysteine-Containing Protein

An additional aspect of the present invention relates to the introduction of one or more selenocysteine residues into a polypeptide or protein which, in its native state, does not contain selenocysteine. Such modification of a protein may be desired in order to alter or enhance the function of the polypeptide or protein. In addition, the selenium moiety of the selenocysteine residue would further provide a highly conserved, isomorphic reference atom for X-ray crystallographic analysis.

The TGA codon intended to encode selenocysteine can be introduced into the DNA encoding the polypeptide or protein by means known in the art, discussed fully above in Section II. The DNA having the TGA codon is then used to construct an expression vector having a suitable operably linked promoter, and a 3' untranslated segment, in the presence of which selenocysteine is co-translationally incorporated into the protein or polypeptide at a site corresponding to the TGA codon. The preferred locations of the untranslated segment are more fully discussed above.

E. Characteristics of Normal and Cancerous Thyroid Tissue

Benign and malignant tumors can develop in the thyroid, and malignant thyroid tumors can spread, for example to lung or bone tissue. The presence of Type I 5' deiodinase mRNA in a tissue can aid in characterizing the presence of thyroid-derived cells. The absence of Type I 5' deiodinase mRNA in a sample of thyroid tissue, on the other hand, would suggest that the tissue is non-functioning and indicate the possible presence of carcinoma.

The presence of type I 5' deiodinase mRNA can be detected by contacting the tissue with detectably labeled DNA containing a sequence complementary to the mRNA. Alternatively, an RNA preparation from the tissue can be introduced into a cell, such as a *Xenopus laevis* oocyte, and expression of Type I 5' deiodinase assayed. In both cases, the amount of mRNA can be compared with that of normal thyroid tissue, or with normal tissue similar to that suspected of containing malignant thyroid-derived cells, in order to evaluate the status of the tissue in question.

Having now generally described the invention, the same will be more readily understood through reference to the following examples which are provided by way of illustration, and are not intended to be limiting of the present invention, unless specified.

EXAMPLE I

Production of cDNA Encoding Rat Type I 5' Deiodinase

A unidirectional, size-fractionated rat liver cDNA library for expression screening in *Xenopus oocytes* was constructed using methods as described in Berry, et al., *Mol. Endocrin.* 4:743-748 (1990).

cDNA synthesis was catalyzed by AMV reverse transcriptase (Life Sciences) (Gubler et al., *Gene,* 25:263-269 (1983)). Double stranded cDNA was size-fractionated on low melting temperature agarose (Sea Plaque, FMMC) and the region corresponding to 1.8 to 2.5 kb isolated. The resulting cDNA was ligated to adaptors (In Vitrogen), inserted into lambda Zap II (Stratagene), and packaged in vitro.

The library was subdivided, amplified, and converted to Bluescript plasmid by in vivo excision as described in the procedures of Stratagene. Plasmid DNA was linearized and transcribed in vivo using T7 RNA polymerase. *Xenopus laevis* oocytes were manually dissected, injected with in vitro transcribed RNA (0.5 to 20 ng per oocyte in 40 nl diethylpyrocarbonate-H$_2$O (DEPC-H$_2$O)), and incubated for 3 days at 18° C. in 50% Leibovitz's L-15 media, 15 mM HEPES, 100 μg/ml gentamycin and 50 units/ml nystatin.

Type I 5' deiodinase assays of oocyte homogenates were performed as described previously (Berry et al., *Molec. Endo.* 4:743-748 (1990)). Because Type I deiodinase exhibits a 1000-fold higher $V_{max}/K_m$ ratio for rT$_3$ than for T$_4$ (Leonard, et al., In: Hennemann, G. (ed.), *Thyroid Hormone Metabolism*, Marcel Dekker, New York, pp. 189-229 (1986), rT$_3$ was used as a substrate for type I deiodinase assays.

RNA-injected or uninjected oocytes were homogenized in 100 mM potassium phosphate (pH 6.9)-1 mM EDTA in microcentrifuge tubes, using a Teflon pestle. Homogenates were then divided into two or three replicate assays. Reaction volumes were adjusted to 100 μl/oocyte. Type I deiodinase reactions were initiated by the addition of 0.5 nM ($^{125}$I)rT$_3$ and 10 mM DTT.

Reactions were incubated for 1 h at 37° C. and terminated by the addition of 50 μl horse serum and trichloroacetic acid to a 10% final concentration. Trichloroacetic acid supernatants were passed over Dowex AG50 W-X2 columns. The columns were washed with 2 ml 10% acetic acid, and the eluates were counted.

This procedure resulted in the isolation of a positive clone, designated G21, which encodes Type I 5' deiodinase. The DNA sequence and predicted amino acid sequence are shown in FIG. 1.

To confirm that this clone encoded Type I 5' deiodinase, it was expressed in JEG-3 human choriocarcinoma cells following DNA transfection. The 2.1 kb insert was excised from Bluescript and inserted into the mammalian expression vector CDM-8 (Aruffo, et al., *Proc. Natl. Acad. Sci.* 84:8573-8577 (1987). The resulting construct was transfected into JEG-3 cells by the Ca$_3$(PO$_4$)$_2$ method (Brent, et al., *Molec. Endo.* 3:1996-2004 (1988). Two days following transfection, cell homogenates or microsomal fractions were assayed for Type I 5' deiodinase activity using rT$_3$ as substrate (Berry, et al., *Molec. Endo.* 4:743-748 (1990)).

DNA sequencing of both upper and lower strands was by the dideoxy method (Sanger et al., *Proc. Natl. Acad. Sci. U.S.A.* 74:5463-5467 (1977)), using a T7 sequencing kit from Pharmacia.

EXAMPLE II

Tissue Distribution of Type I 5' Deiodinase

To determine the tissue distribution of Type I 5' deiodinase mRNA, RNA was isolated from rat tissues by standard guanidiniumthiocyanate methods as described previously (Berry et al., *Molec. Endo.* 4:743-748 (1990)). Briefly, rates were made hyperthyroid by five sc injections of T$_4$ (12 μg/100 g BW) over 3-5 days. Hypothyroidism was produced by giving rats 0.02% methimazole in drinking water for 3 weeks. Livers from six rats were used for each RNA preparation.

Liver was homogenized in 4.0M guanidium thiocyanate, 20 mM sodium acetate, 10 mM vanadyl ribonucleoside complex, and 20 mM dithiothreitol (DTT) in a Brinkmann Polytron homogenizer (Westbury, N.Y.), followed by three passages through a 20-gauge needle to shear chromosomal DNA. The homogenate was layered onto 12-ml cushions of 5.7M CsCl-0.1M EDTA, pH 8.0, and centrifuged at 27,000 rpm for 18 h in a Beckman SW 28 rotor (Fullerton, Calif.) at 15° C.

RNA pellets were resuspended in 2 mM EDTA (pH 8.0)-0.1% sodium dodecyl sulfate (SDS) and extracted with an equal volume of phenol-chloroform-isoamyl alcohol (25:24:1), followed by ethanol precipitation. Precipitated RNA was resuspended i 2 mM EDTA (pH 8.0)-0.1% SDS. Polyadenylated [poly(A)+] RNA was obtained by two cycles of chromatography on oligo-(dT) cellulose (Collaborative Research, Waltham, Mass.).

Poly(A)+ RNA was ethanol precipitated and resuspended in diethyl pyrocarbonate treated (DEPC)-H$_2$O before injection into oocytes or agarose gel size fractionation. Either total or poly(A)+ RNA was electrophoresed on 1.1% agarose formaldehyde gels. Blots were probed with clone G21 cRNA or β-actin cRNA, and washed at high stringency.

The results are shown in FIG. 2. Lanes 1-6 of FIG. 2 contain 20 μg of total RNA from kidney, liver, spleen, heart, lung, and small intestine, respectively. Hybridization to a β-actin probe showed that there was significantly less liver mRNA than is present in the other samples, accounting for the lower signal in this lane.

Lane 7 and 8 of FIG. 2 contain 2 μg poly(A)+ RNA, from the thyroids of methimazole treated rats (lane 7) and from kidney (lane 8). Lanes 9 and 10 contains 5 μg poly(A)+ RNA from pituitary and brown adipose tissue, respectively. Autoradiography of lanes 1-6 was for 4 days, lanes 7 and 8 for 1 hr., and lanes 9 and 10 for 1 week.

To measure the effect of thyroid status on Type I iodothyronine 5' deiodinase mRNA levels, rats were made hypothyroid by treatment for 3 weeks with 0.02% methimazole in the drinking water. Hyperthyroidism was induced by intraperitoneal injection of 50 μg T$_3$ daily for three days. Results are shown in FIG. 3. Liver and kidney poly(A)+ RNA (5 μg) from hypothyroid (− lanes), euthyroid (Eu lanes), and hyperthyroid (+ lanes) rats was probed with G21 cRNA as described above. Autoradiography was performed for 1 hr.

EXAMPLE III

Effect of Deletions on 5' Deiodinase Expression

Deletions were constructed by restriction digestion at the indicated sites in clone G21 and convenient sites in the vectors, followed by agarose gel purification of the desired fragments, religation, and mapping of the resulting constructs. The Acc I frameshift was constructed by digestion with Acc I, followed by conversion to blunt ends with DNA polymerase large fragment, and religation. All mutations were confirmed by DNA sequencing.

RNAs were transcribed in vitro and 0.1 to 20 ng injected per oocyte. DNA transfections (Brent et al., *Molec. Endo* 3:1996-2004) and deiodinase assays (Berry et al., *Molec. Endo.* 4:743-748 (1990)) were as described previously. Assay of human growth hormone (hGH) in the media from a cotransfected hGH expressing plasmid confirmed equal transfection efficiencies (Brent et al., *Molec. Endo* 3:1996-2004).

Oocyte activity of 100% is defined as deiodination of 30 to 40% of 2 nM $^{125}$IrT$_3$/hr with a homogenate of 4 ooctyes injected with 0.1 ng G21 RNA per ooctye. G21 RNA was at least 100-fold more active per nanogram than liver poly(A)+ RNA.

JEG-3 cells were homogenized and 100 to 300 μg protein from homogenates or 20,000×g pellets were incubated in a volume of 400 μl containing 25 mM DTT and 5 nM $^{125}$IrT$_3$ for 1 hr. $^{125}$I was quantitated as described (Berry et al., *Molec. Endo.* 4:743-748 (1990)). Equal quantities of $^{125}$I and 3,3' diiodothyronine are produced during this reaction. The results are shown in FIG. 7; all assays were in duplicate. ND, not done.

In separate experiments, the TGA codon at nucleotide 382 was replaced by the indicated codons (see FIG. 8) using the P-select® in vitro mutagenesis system of Promega. Briefly, the insert from clone G21 was ligated into P-select and single stranded phagemid DNA was obtained. Oligonucleotides corresponding to the desired changes were annealed to the single-stranded DNA and double-stranded DNA was synthesized. The entire coding regions of plasmids thus obtained were sequenced to confirm that these were the only mutations. Injection and assays were described above.

EXAMPLE IV

In vitro Translation and SDS Polyacrylamide Gel Electrophoresis of Type I 5' Deiodinase Constructs In vitro transcriptions of G21, substitution mutants, and the Hind III internal deletion were described above. In vitro transcribed RNA was translated in rabbit reticulocyte lysates (Promega) using $^{35}$S methionine as described in the procedures of Promega. In vitro translation products were analyzed on a 15% polyacrylamide gel and visualized by fluorography following impregnation of the gel with EN$^3$HANCE (DuPont). The results are shown in FIG. 9.

EXAMPLE V

Sensitivity of Type 5' Deiodinase to Gold

Wild type (TGA) or cysteine mutant (TGT) G21 cDNA in CDM-8 was transfected into JEG-3 as described in Example III. Cell sonicate protein, 435 μg (wild type) or 680 μg (cysteine mutant), was incubated in a volume of 500 μl containing 10 mM DDT and 300 nM $^{125}$I rT$_3$ for 30 min in the presence of 0, 10 and 100 nM gold thioglucose (GTG). $^{125}$I was quantitated as described (Berry et al., *Molec. Endo.* 4:743-748 (1990)). 1β-D-Thioglucose (5 μm) had no effect on enzyme activity. The results are presented in Table. 1.

TABLE 1

The sensitivity of Type I iodothyronine 5' deiodinase to gold thioglucose (GTG) is markedly reduced by substitution of cysteine for selenocysteine-126

| Transfected cDNA | GTG (nM) | Deiodinase Activity of JEG cell sonjcates pmol rT$_3$ min$^{-1}$ mg protein$^{-1}$ | Inhibition (%) |
| --- | --- | --- | --- |
| A. TGA (selenocysteine-126) | 1 | 7.0 | 0 |
|  | 10 | 4.0 | 43 |
|  | 100 | 0.95 | 95 |
| B. TGT (cysteine-126) | 0 | 1.3 | 0 |
|  | 10 | 1.3 | 0 |
|  | 100 | 1.1 | 13 |

EXAMPLE VI

Effect of 3' Untranslated Region on Co-translational Incorporation of Selenocysteine Rat Type I iodothyronine 5' deiodinase is encoded by a DNA sequence of approximately 778 nucleotides in length, as shown in FIG. 1. However, for successful translation of 5' deiodinase in Xenopus oocytes and JEG cells, sequences between nucleotides 1360 and 1615 in the untranslated region of the cDNA must be present.

In the cDNA, there is a region of approximately 582 nucleotides between the 3' end of the 5' deodinase coding region and the necessary 255-nucleotide untranslated region. However, the 255 nucleotide segment can also be inserted immediately 3' of the coding region to achieve translation of a completely active enzyme. No expression of the enzyme is found if these 255 nucleotides are removed or if the sequence is inverted.

According to the present example, expression of enzymatically active 5' deiodinase is achieved by transfection of a host cell with a DNA sequence comprising the structural gene for 5' deiodinase, and a DNA segment consisting of nucleotides 1360-1615 of the untranslated region of 5' deiodinase cDNA. The DNA segment can be located immediately 3' to the coding region. Alternatively, up to approximately 582 nucleotides can be present between the 3' end of the coding region and the 255 nucleotide segment.

EXAMPLE VII

Recognition of UGA as a Selenocysteine Codon in Type I Deiodinase Requires Sequences in the 3' Untranslated Region A. Deletion and Inversion Mutations of Rat 5' deiodinase cDNA 3' untranslated Region and Rat 5' deiodinase Constructs Containing 3' untranslated Sequences from Rat or Human 5' deiodinase or Rat GPX cDNAs Isolation of the rat 5' deiodinase cDNA has been reported previously. Deletion mutants were constructed in either Bluescript (Stratagene) or CDM-8 (Aruffo et al., *Proc. Natl. Acad. Sci.* USA 84:8573-8577 (1987)) by digestion with restriction enzymes and conversion to blunt ends with DNA polymerase large fragment when ends were incompatible, followed by religation. Mutants constructed in Bluescript were subsequently cloned into CDM-8 at appropriate sites. Site-directed mutagenesis was performed as described previously (Zinoni et al., *Proc. Natl. Acad. Sci. USA* 87:4660-4664 (1990)), using the P-select in vitro mutagenesis system (Promega). Using the rat 5' deiodinase cDNA as a probe, a partial human 5' deiodinase cDNA from a human liver cDNA library has been isolated by standard hybridization screening techniques. Rat GPX cDNA was obtained. (Ho et al., *Nucl. Acids Res.* 16:5207 (1988)). Chimeric constructs were generated by PCR-amplification using 5' oligonucleotides encoding an XmaI site and 3' oligonucleotides encoding a NotI site adjacent to sequences specific for the region to be amplified. PCR products were cloned into sequences specific for the region to be amplified. PCR products were cloned into XmaI+NotI cut CDM-8 containing the 5' deiodinase cDNA. This vector fragment contains the 5' deiodinase coding region and 126 base pairs of 3' untranslated region, and is non-functional for deiodinase activity in transient transfection and oocyte injection assays. JEG-3 or COS-7 cells were transfected with calcium phosphate-DNA precipitates as described previously (Brent et al., *Molecular Endocrinol.* 3:1996-2004 (1989)). Transfection efficiencies were monitored by assay of human growth hormone in the media, produced by a cotransfected constitutive thymidine kinase promoter-directed human growth hormone-expressing plasmid (Brent et al., *Molecular Endocrinol.* 3:1996-2004 (1989)). Cell sonicates were assayed for 5' deiodination of $^{125}$I reverse T$_3$ in reactions containing 10-250 μg protein, 300 mM $^{125}$I reverse T$_3$, and 10 mM DTT in 0.1M potassium phosphate, pH 6.9, 1 mM EDTA. Incubations were for 1 hr in 500 μl volume.

Type I iodothyronine deiodinase catalyzes the first step in thyroid hormone action, the monodeiodination of the prohormone, thyroxine (T4), to form the active thyroid hormone, 3,5,3'-triiodothyronine (T$_3$). It is now shown that selenocysteine is required for normal 5' deiodinase activity in the rat enzyme (Berry et al. *Nature* 349:438-440 (1991))). A cysteine mutant is also functional, albeit with 10-fold higher apparent K$_m$ for the preferred substrate, 3,3',5'triiodothyronine (reverse T$_3$7,10). The open-reading frame of the 2.1 kb rat 5' deiodinase mRNA begins at nucleotide 7 and ends at 780, and the UGA (selenocysteine) codon is located at nucleotides 382-384 (Berry et al., *Nature* 349:438-440 (1991) (FIG. 13A). Deletion of sequences 3' to nucleotide 907 in the wild-type 5' deiodinase cDNA resulted in complete loss of deiodinase activity in either JEG-3 or COS-7 cell transient transfections (FIG. 13A). However, deletion of the same sequences had no effect on the activity expressed by the cysteine mutant. Sequences in the 3' untranslated region are therefore required for selenocysteine, but not cysteine, incorporation. These results argue against a regulatory role for the deleted sequences in transcription, RNA processing, or stability. Further studies were performed to identify the specific sequences in the wild-type cDNA necessary for selenocysteine incorporation. Deletion analyses identified sequences between nucleotides 1440 and 1615 as being required for expression of 5' deiodinase activity (FIG. 13A). To confirm that these sequences were required only at the level of translation, RNA was prepared by in vitro transcription of plasmids containing either the full length 5' deodinase CDNa, the cDNA truncated at nucleotide 1580, or the cDNA lacking nucleotides 1278 to 1495. The relative 5' deiodinase activity produced by injection of these RNAs into Xenopus oocytes paralleled that produced by transfection, evidence that impaired translation causes the reduced expression by the 3' untranslated mutants.

3' untranslated sequences of the cDNA for the rat 5' deiodinase were compared with the sequence of a cDNA for the human 5' deiodinase. Although the 3' untranslated sequences are overall about 55% conserved, a region of ~79% identity (Nucleotides 1642 to 1819) corresponded to the essential 3' untranslated sequences (1440-1615) identified in the rat 5' deiodinase cDNA. A construct in which conserved human 3' untranslated sequences (1572-1893) were inserted downstream of the rat coding region (human WT) produced deiodinase activity equal to that produced by the construct containing the essential rat 3' untranslated sequences (FIG. 13B). A second construct (human MN1) containing an abbreviated 3' untranslated segment (1700-1882) produced 53±3% of the wild-type level of activity. Examination of the 3' untranslated region of the rat GPX mRNA revealed less than 38% primary sequence similarity to the conserved 5' deiodinase sequence. However, addition of nucleotides 922 to 1155 from the 3' untranslated of the rat GPX cDNA to the coding region of the rat 5' deiodinase cDNA restored 42 ±3% of the 5' deiodinase activity (FIG. 7b). The distance between the UGA codon and the midpoint of the functional 3' untranslated sequences varies from 548 nucleotides in the rat GPX mRNA (Ho et al., *J. Nucl. Acids Res.* 16:5207 (1988)) to 1145 in the rat (Berry et al., *Nature* 349:438-440 (1991)) and 1409 in the human 5' deiodinase in mRNAs, respectively. Two constructs with reduced spacing between the coding region and the 3' untranslated sequences produced levels of deiodinase activity 30-40% higher than did the wild-type cDNA (FIG. 13A), suggesting that the spacing between the 3' sequences and the UGA codon influences the efficiency of selenocysteine-insertion.

B. Predicted Secondary Structures in the 3' untranslated Regions of Selenocysteine-encoding RNAs The lack of primary sequence similarity between the 5' deiodinase and GPX 3' untranslated sequences suggested that secondary structure may be involved in regulating translation of the UGA codons in these mRNAs. Analyses of these sequences predicted the stem-loop structures shown in FIG. 14, all of which have high negative free energy. All three contain a large stem-loop with three adjacent A's in the loop and an unpaired UGAU in the stem. The 5' deiodinase sequences also predict a smaller putative stem-loop located 5' to the larger one. The smaller stem-loop is disrupted in the rat 5' deiodinase Δ1278-1495 construct and deleted in the human M1 construct, both of which have impaired activity. Thus, the smaller loops may contribute to the process of selenocysteine-insertion, but are not absolutely essential.

C. Deletion Mutations in the Stem Loop Regions of Rat 5'DI and GPX mRNAs

To test the function of the large putative stem-loop structures, the deletions shown in FIG. 15 were generated. Removal of either the 35 bp stem-loop (Rat M1) or the 9 bp loop (Rat M2) resulted in loss of the capacity to confer deiodinase expression. Similarly, deletion of the 8 bp GPX loop (GPX M1) inactivated this construct.

D. UGA Recognition Function of 3'0 Untranslated Regions

Reticulocyte lysates translate rat 5' deiodinase mRNA inefficiently, producing small amounts of full length ~27 kDa protein, with most of the translated product being the ~14 kDa protein predicted by termination at the UGA codon (Berry et al., *Nature* 349:438-440 (1991)). If the 3' untranslated sequences are involved in selenocysteine codon recognition, the ratio of 27 to 14 kDa protein should be reduced in in vitro translations of 3' untranslated mutant transcripts. In vitro transcripts of wild-type and mutant 5' deiodinase constructs were prepared. The RNA was translated in vitro and the translation products were immunoprecipitated with 5' deiodinase specific antisera generated against a rat 5' deiodinase amino-terminal peptide. The 27 and 14 kDa $^{35}$S methionine labelled products were quantitated after SDS-polyacrylamide gel electrophoresis. The ratio of 27 to 14 kDa protein was 0117±0.03 for the Rat WT, 0.08±0.04 for the Human M1, and 0.013±0.004 for the Rat M2 construct. These results establish the UGA recognition function of the 3' untranslated regions.

E. Sequence Similarities in the Stem-Loop Regions of Rat and Human 5' deiodinase and Mammalian GPX cDNAs As mentioned, the 3' untranslated sequences of the various selenocysteine-encoding mRNAs exhibit little primary sequence similarity. Alignment of the proposed stem-loop regions of the rat and human 5' deiodinase mRNAs with the 3' untranslated regions of the mammalian GPX mRNAs identifies the conserved nucleotides shown in FIG. 10. Inversion of the sequences between 1245 and 1615 in the rat 5' deiodinase cDNA resulted in loss of 5' deiodinase activity (FIG. 13A). The predicted stem-loop in this construct is similar to the wild-type, but since the sequence is complementary, none of the conserved bases are present. The 3' untranslated region of human plasma GPX (Takahashi et al., *Biochem.* 108:145-148 (1990)) contains no significant similarity to the sequences in FIG. 16, however, this sequence is not full length, as it lacks a polyadenylation signal sequence and poly A tail. The recently reported cDNA for rat selenoprotein P (Hill et al., *J. Biol. Chem.* 266:10050-1053 (1991)) contains a 3' untranslated region of >1600 nucleotides and secondary structure analyses predict 15 stem-loops with free energies of −20 kcal or less. Six of these contain UAAA or AAA sequences in the loop. Because of the numerous potential stem-loops in this long 3' untranslated, the identification of specific regions involved in selenocysteine-insertion may require deletion mapping or other functional analyses.

F. Summary

Previous studies of the *E. coli* FDH mRNA established that only the sequences immediately adjacent to the UGA codon are required for its recognition as a selenocysteine codon (Zinoni et al., *Proc. Natl. Acad. Sci. USA* 87:4660-4664 (1990)). The present inventors have surprisingly discovered that an approximately 200 nucleotide segment, more generally a 200-255 nucleotide segment, located more than 1 kilobase downstream of the UGA in the 5' deiodinase mRNAs is essential for insertion of selenocysteine into this protein. While most of the results were obtained using transient expression techniques, it has been demonstrated that these sequences are required for in vivo and in vitro translation of the intact, fully functional protein. Thus, this segment of these nRNAs is termed a "selenocysteine-insertion sequence" (SECIS) motif. The requirement for a SECIS motif in the 5' deiodinase mRNAs for successful translation of this protein, and the presence of sequences with similar function in the GPX mRNAs, identifies a previously unrecognized regulatory step in the expression of genes encoding eukaryotic selenocysteine-containing proteins. Such motifs may be required in eukaryotic expression vectors for insertion of the more reactive selenium in place of sulfur in sulfhydryl active site proteins for purposes of biochemical or structural analyses.

TABLE II

Demonstration of the cysteine-mutant as a reporter gene in transfections of COS-7 cells

| Reporter Plasmid Transfected (μg) | | Activity | | |
|---|---|---|---|---|
| G-5DI[1] | TKGH[2] | DI CPM I-/min/10 μl cell extract | hGH CPM $^{125}$I min/100 μl media | DI hGH |
| 1,2 | 5 | 3 | 22,000 | 1843 | 12.0 |
| 3,4 | 1 | 3 | 12,600 | 5210 | 2.4 |
| 5,6 | 0.5 | 3 | 7,900 | 5690 | 1.4 |

[1]G-5DI is the cysteine-126 mutant with sequences 3' to the XMA site at 907 removed. Cells were transfected in pairs using CaPO$_4$. Media and cell lysates (200 μl) were harvested 2 days later. Assays used 10 μl of cell lysate and 100 μl of media for assay of deiodinase (DI) and human growth respectively.
[2]TKGH is described in Mol. and Cell. Biol. 69:3172-3179 (1986).

EXAMPLE VIII

Expression of cysteine mutant (G-5) is proportional to DNA input into a transfection system The expression of cysteine mutant (G-5) is proportional to DNA input into the transfection system (see Table II). In column 1 are shown the quantities of DNA co-transfected into COS cells (G5DI) together with 3 μg of TKGH. The activity in the cell extracts (deiodinase-"DI") and hGH in the medium (hGH) are shown on the right side of the table. The calculated ratio of deiodinase to hGH is shown in the far right column. TKGH is a reporter gene for control of internal transfection efficiency. If the uptake and expression of G5 is proportional to DNA input into the transfection system then this will be reflected in the ratio of DI to hGH. As seen in the far right column the ratio of DI to hGH parallels the ratio of input G5DI to TKGH DNA over a 10-fold range (5/3 to 0.5/3). Notable is the fact that this relationship is maintained even though the uptake and expression of the TKGH plasmid in plates 1 and 2 (1843 cpm) is less than half of that in plates 3 through 6 (5210 and 5690). Since the expression of G5 does not require the selenocysteine insertion sequence motif it should have a broader repertoire of utility for different cell lines than would the wild-type enzyme. The activity of G5DI in this experiment is regulated by the CMV promoter in the construct CDM8. A further useful modification is to attach a signal peptide to the amino terminus of the G-5 or wild-type enzyme to permit deiodinase secretion into the media similar to the transiently expressed human growth hormone (hGH) employed in the experiment shown in Table II. For example, the 26 amino acid signal peptide of hGH is attached to the G-5 sequence via synthesis of an oligonucleotide which is ligated to the cDNA by appropriate recombinant techniques before or after deletion of the two putative membrane-spanning domains of the enzyme located between amino acids 1-21 and 56-76. The deiodinase is assayed simply by sampling the media. This is advantageous in studies in which the time course of expression is of interest.

All references discussed in above Examples VII and VIII are hereby incorporated by reference.

EXAMPLE IX

Production of cDNA Encoding Human Type I 5'-Deiodinase

Once a cDNA encoding rat Type I 5'-deiodinase was isolated, the corresponding human cDNA was readily isolated using the rat gene as a probe. After expression and study of the human deiodinase, it is apparent that its sequence homology with rat deiodinase is paralleled by similarity of properties. Most noteworthy among these are that the human deiodinase is also a selenocysteine-protein and that it requires a 3'-untranslated sequence for expression incorporating selenocysteine.

A. Methods

Materials

Two cDNA and one human genomic library were screened. The first was a human liver cDNA library in a CDM-8 vector prepared according to the methods of Arrufo and Seed (*Proc. Natl. Acad. Sci. USA* 84:8573-8577 (1987)) and kindly provided by Dr. Brian Seed. Because we could not identify the complete coding sequence from this library, a second human kidney cDNA library in λgt10 was obtained through the courtesy of Dr. Graeme Bell. Third, a human genomic library in λFixII vector was purchased from Stratagene (La Jolla, Calif.).

Library Screening

The human liver library in the CDM-8 vector was plated on 400 cm$^2$ agar plates, colonies were immobilized on nylon filters (GeneScreen Plus, DuPont, New England Nuclear, Boston Mass.), denatured in NaOH, neutralized in tris buffer, and the DNA cross-linked to the filter using a UV-Stratalinker 1800 (Stratagene). Filters were prehybridized for 3 hours at 65° C. in 1M NaCl, 1% SDS, 10% dextran sulfate, and denatured salmon sperm DNA (100 ug ml$^{-1}$). They were hybridized overnight at 65° C. in the same buffer with a denatured rat cDNA probe (nucleotides 1 to 745, FIG. 1) labelled with dCT$^{32}$P using random primers (Prime Time "C", International Biotechnologies, Inc., New Haven, Conn.). Filters were washed in 2×SSC (0.3M NaCl, 0.03M sodium citrate), 0.1% SDS twice for 15 minutes at 25° C. and once for 20 minutes at 65° C., followed by a high stringency wash in 0.1×SSC, 0.1% SDS for 30 minutes at 65° C.

The human kidney cDNA library in the λgt10 vector was expressed in *E. coli* and phage DNA was transferred to nylon filters, denatured, neutralized, and cross-linked as above. Filters were prehybridized and hybridized at 65° C. and washed as above. This library was probed with a 417 base pair cDNA fragment (nucleotides 134 to 551, NcoI to PstI) from the 5' end of the isolated human liver cDNA clone. Both upper and lower strands were sequenced by the dideoxynucleotide chain termination method using T7 polymerase according to the instructions of the kit manufacturer (Pharmacia, Piscataway, N.J.).

Northern Blotting

Human thyroid tissue was obtained from a patient undergoing subtotal thyroidectomy for Graves' disease and frozen in liquid $N_2$ within 5 minutes of removal. Human liver and kidney tissue were obtained form the National Disease Research Interchange (Philadelphia, Pa.). Total cellular RNA was prepared by homogenization of tissue in 5.5M guanidine thiocyanate and centrifugation through cesium trifluoracetate (Pharmacia). Polyadenylated RNA was isolated by two cycles of chromatography using oligo dT cellulose Type 7 (Pharmacia) according to the instructions of Pharmacia. Poly(A)+mRNA was subjected to gel electrophoresis in a 1% agarose gel containing 20 mM 3-(N-morpholino) propane sulfonic acid (MOPS) pH 7.0, 5 mM sodium acetate, 1 mM EDTA, and 1.3% (wt/vol) formaldehyde. Gels were rinsed in 10×SSC and blotted overnight in 20×SSC to a GeneScreen Plus nylon membrane (DuPont). RNA was cross-linked to the nylon with a UV Stratalinker. Following prehybridization with salmon sperm DNA and *E. coli* tRNA, the filter was hybridized with a 1.5 kb cRNA from the human liver clone (nucleotides 32 to 1516, XbaI), that was transcribed in vitro from a pBluescript KS vector (Stratagene) using T7 polymerase and UT$^{32}$P. Filters were washed in 1×SSC, 0.1% SDS at 25° C. followed by washes of increasing stringency with a final wash being 0.1×SSC, 0.1% SDS at 65° C. according to standard techniques.

DNA Transfections and Deiodinase Assays

Transfection of COS-7 cells was by calcium phosphate DNA coprecipitation and internal transfection efficiency was monitored using TKGH as previously described (Berry, et al., *Nature* 349:438-440 (1991)). Two days after transfection, cells were harvested and sonicated in 0.1M potassium phosphate, 1 mM EDTA pH 6.9 (PE buffer) containing 25 mM dithiothreitol (DTT). Cell sonicate protein concentration was approximately 12 mg ml$^{-1}$ by Biorad determination using gamma globulin as a standard.

Deiodinase reactions contained 10 to 55 μg of cell sonicate protein in 300 μl PE buffer and varying concentrations of DTT, 3,5,3'-triiodothyronine (rT$_3$), and other reagents as indicated. Deiodinase activity was monitored by the release of $^{125}$I$^-$ from $^{125}$I-rT$_3$ (DuPont, New England Nuclear) under conditions specific for each experiment. Incubations were for 30 minutes at 37° C. and $^{125}$I was quantitated as previously described (Berry, et al., *Mol. Endocrinol.* 4:743-748 (1990)).

T$_4$ to T$_3$ conversion was measured by incubation of approximately 600 μg of COS-7 cell sonicates with 25 mM DTT, 100 nM $^{125}$I-T$_4$, and 200 nM or 10 μM rT$_3$ for 16 hours at 37° C. in a total volume of 200 μl PE with or without 0.5 mM PTU. T$_4$, T$_3$ and I$^-$ were separated by paper chromatography and identified by staining of chromatographed unlabelled standards. The $^{125}$I content of the products was quantitated by counting the paper strips in a gamma scintillation counter. All assays were performed in duplicate. Kinetic analyses were performed as previously described (Berry, et al., *J. Biol. Chem.* 266:14155-14158 (1991)) by drawing double reciprocal plots of deiodination rate vs. substrate concentration. Secondary replots of the slopes versus the concentration of the varied substrate or inhibitor were drawn to calculate the apparent Ki's for T$_4$ and GTG with respect to rT$_3$ and for PTU with respect to DTT. Secondary replots of the y-intercepts versus the concentration of the varied substrate or inhibitor were drawn to calculate the apparent Kb for DTT and the apparent Ki of PTU with respect to rT$_3$. Since the enzyme is not pure, all kinetic constants are apparent.

Affinity Labelling with Bromoacetyl T$_3$

Bromoacetylated $^{125}$I labelled T$_3$ (BrAcT$_3$) was synthesized from $^{125}$I T$_3$ (DuPont, New England Nuclear, specific activity 1200 uCi mg$^{-1}$) and bromoacetyl chloride according to published methods (Mol, et al., *Biochem. Biophys. Res. Commun.* 124:475-483 (1984)). The final product in 2 ml of acidified 20% ethanol was diluted with 3 volumes of water and purified by chromatography on a column (2.5×0.8 cm) of Sephadex LH-20 (Pharmacia). After washing with 20 ml of water to remove free $^{125}$I, the product was eluted with 100% ethanol (2.5 ml in 0.5 ml aliquots). It was >99% pure by thin layer chromatography on silica gel in ethyl acetate/glacial acetic acid (9:1). Affinity labelling was performed by incubating 50 to 70 μg cell sonicate protein in 50 μl of PE, 10 mM DTT, containing indicated additions at room temperature for 5 minutes, followed by exposure to 0.1 uCi BrAcT$_3$ for 10 minutes also at room temperature. Some reactions contained excess cold BrAcT$_3$ (364 nM). After addition of loading buffer and heating at 100° C. for 5 minutes, samples were analyzed by SDS PAGE on a 12% gel. Densitometric quantitation of the autoradiographs was performed by a Molecular Dynamics computing densitometer (Sunnyvale, Calif.).

Sequence Analysis

Nucleotide and protein sequence analysis was performed using the Sequence Analysis Software Package from the Genetics Computer Group (Devereux, et al., *Nucl. Acids Res.* 12:387-395 (1984)).

B. Isolation of a Human 5' Deiodinase CDNA

The initial screening of the human liver cDNA library identified two identical 2188 base pair clones from a total of approximately 600,000 recombinants. This sequence did not contain a polyadenylation signal or tail. By its close homology to the rat 5' deiodinase sequence, it had a 5' boundary at nucleotide number 32 (FIG. 5). The library was re-screened using a liver cDNA fragment consisting of nucleotides 134 to 551

(NcoI to PstI), but no other recombinants were identified that extended 5' to nucleotide 32.

To complete the coding sequence, a human kidney cDNA library was screened using the same human cDNA NcoI to PstI fragment which identified an approximately 4 kb insert. This clone contained sequences identical to the human liver cDNA between nucleotides 32 and 300 but diverged 3' to this region. The insert also contained 1.8 kb of sequence 5' to nucleotide 32. This recombinant kidney clone apparently contained an exon flanked on two sides by intronic sequences which had not undergone splicing (FIG. 4A). This was confirmed by identifying and sequencing a similar fragment from a human genomic library. There were several consensus branch points and splice junctions at the 3' border of the upstream intron. There was no initiator methionine within the 150 base pairs 5' to the nucleotide designated number 7 based on the homology to the rat 5' deiodinase cDNA (FIG. 5).

A cDNA containing the coding and downstream sequences of the human 5' deiodinase was constructed from the liver (HL5) and kidney (HK5) recombinants as follows. A 2.3 kb EcoRI fragment from the 4.4 kb insert in HK5 was subcloned into Bluescript and a 500 nucleotide PstI fragment of this subclone was then inserted into Bluescript (HK5Pst, FIG. 4A). The 1251 base pair NcoI fragment from HL5 (FIG. 4A) was inserted into HK5Pst at the NcoI site. The Hind3/NsiI fragment containing the initiator methionine from this new construct was then substituted for the shorter Hind3/NsiI fragment of the HL5 clone. The numbering of this sequence is assigned arbitrarily by its homology to the rat 5' deiodinase sequence (FIGS. 1, 4B and 5). This results in a cDNA of 2222 nucleotides, slightly shorter than the mRNA identified by Northern blotting (FIG. 4B). Of note is the fact that a UGA codon is present at the identical position (382) in both the human and rat 5' deiodinase sequences. As will be shown, this does not function as a stop codon but encodes selenocysteine as has been shown for the rat enzyme (Berry, et al., *Nature* 349:438-440 (1991)). A UAA stop codon is found at nucleotides 754 to 756. The deduced amino acid sequence is 249 amino acids long with a calculated molecular weight of 28.9 kDa (FIG. 4B) and is highly homologous (88%) to the rat protein (FIG. 1). There is one potential glycosylation site at amino acid 203.

C. Characterization of Human 5'-Deiodinase

Northern Blotting

Previous studies have identified 5' deiodinase activity in human liver (Hardy, et al., *Am. J. Med. Sci.* 292:193-197 (1986); Visser, et al., *J. Clin. Endocrinol. Metab.* 67:17-24 (1988)), kidney (Boye, N., *Acta Endocrinol.* 112:536-540 (1986)), and thyroid (Ishii, et al., *J. Clin. Endocrinol. Metab.* 52:1211-1217 (1981)). FIG. 6 shows that the human cRNA hybridizes to a 2.4 kb mRNA in all 3 tissues. This mRNA is approximately 200 nucleotides longer than the rat liver 5' deiodinase mRNA, which is shown for comparison on the same blot.

Kinetics

To establish that the cDNA encode a functional 5' deiodinase, the enzyme was transiently expressed in COS-7 cells which contain no endogeneous deiodinase. The transiently expressed enzyme was readily identified by its capacity to deiodinate $rT_3$ in a saturable fashion with an apparent Ka of $0.52 \pm 0.04$ $\mu$M (Table III) and Vmax of $63.2 \pm 16.4$ pmol min$^{-1}$ mg$^{-1}$, both at 10 mM DTT. $T_4$ is a competitive inhibitor of $rT_3$ deiodination with an apparent Ki of 6.2 $\mu$M. This is about 16 higher than the Ka for $rT_3$, demonstrating that the latter is the preferred substrate. The apparent Kb for DTT is 5.0 mM. PTU is an uncompetitive inhibitor of $rT_3$ deiodination (Ki 0.17 $\mu$M) and is competitive with respect to DTT (Ki 0.014 $\mu$M) as would be expected from the ping-pong kinetics of the Type I reaction. As is the case with the rat 5' deiodinase enzyme, deiodination is competitively inhibited by gold thioglucose (GTG) with an apparent Ki of 4.7 nM (FIG. 10). The enzyme also catalyzes $T_4$ to $T_3$ conversion by a PTU-sensitive mechanism with the production of equimolar quantities of $T_3$ and I-(FIG. 11), albeit at a much slower rate.

Affinity Labelling

Bromoacetyl affinity labelling of the human and rat transiently expressed proteins was performed to establish that the in vitro expressed protein was of the size predicted by the deduced amino acid sequence presuming that the UGA encodes selenocysteine. In cells transfected with the CDM-8 vector alone (FIG. 12, lanes 1 and 2), several discrete labelled bands are present (64, 46, 34, and 16 kDa). Labelling of the 16 kDa band is completely and that of the 64 and 46 kDa bands partially blocked by excess unlabelled $BrAcT_3$. Transfection with the vector containing the human (lanes 3-10) or rat (lanes 11-18) cDNA produced a protein of $\sim$28 kDa which labelled with $BrAcT_3$ (FIG. 12). The $BrAcT_3$ labelling of both the transiently expressed human and rat 5' deiodinase proteins is inhibited by excess cold $BrAcT_3$, 100 nM gold thioglucose (GTC), and $rT_3$ (3 $\mu$M and 10 $\mu$M). $T_4$ (30 $\mu$M) does not inhibit labelling of the human 5' deiodinase, but does reduce that of the rat by 67%. PTU (100 $\mu$M) causes only a slight decrease (35-40%) in the labelling of both proteins, which is expected from its interaction only with the putative enzyme-selenolyl-iodide intermediate complex (Berry, et al., *J. Biol. Chem.* 266:14155-14158 (1991)).

D. Summary

The present results demonstrate that the human 5' deiodinase gene and protein are highly homologous to those of the rat. The coding region nucleotide sequences of the two species are 82% homologous (FIG. 5) and their putative amino acid sequences are 88% identical. The cDNA we have isolated is approximately 200 nucleotides shorter than the mRNA in the liver, kidney, and thyroid. It is lacking sequences at both the 5' and 3' extremes since it does not contain a poly A tail and the 5'-untranslated portion is of unknown length due to the presence of a long unspliced intronic sequence in the kidney cDNA clone. As demonstrated by transfection studies and the close homology with the rat sequence, the human cDNA encodes a functional 5' deiodinase. The deduced human protein sequence if 7 amino acids or 0.7 kDa shorter than that of the rat.

In addition to a high degree of homology in coding sequence, the SECIS motif (Selenocysteine Incorporation Sequence), recently identified in the 3'-untranslated regions of these two mRNAs as well as in the selenoenzyme glutathione peroxidase, bears a high degree of homology with the rat sequence (Berry, et al., *Nature* 353:273-276 (1991)). The secondary structure of the mRNA in this region suggests that there is RNA/protein or RNA/RNA interaction involved in the mechanism by which suppression of the UGA stop codon functions and insertion of selenocysteine occurs. Comparison of the 321 nucleotide sequence (1573 to 1894) with the corresponding rat SECIS motif shows 66% homology.

Kinetic studies of the transiently expressed enzyme demonstrate considerable similarities between the properties of the in vitro expressed human 5' deiodinase and those of the human liver microsomal enzyme (Table III). However, the Vmax of the in vitro expressed 5' deiodinase is only 25 to 50% that of the native enzyme. This may be due to a number of factors including the transient nature of the expression, our use of whole cell sonicates rather than the microsomal fraction as the enzyme source, and differences between COS-7 cells and hepatocytes in the efficiency of selenocysteine insertion. The kinetics of the in vitro expressed human and rat enzymes (Berry, et al., *J. Biol. Chem.* 266:14155-14158 (1991)) are also quite similar, a major difference being that the Ka for $rT_3$ ($0.52\pm0.04$ $\mu M$) is about twice that of the rat 5' deiodinase ($0.25\pm0.04$ $\mu M$). Both enzymes catalyze $T_4$ to $T_3$ conversion in a PTU-inhibitable fashion at a much slower rate than $rT_3$ 5' deiodination (FIG. 11).

Bromoacetyl $T_3$ labelling of a 27 kDa protein has been correlated with the activity of 5' deiodinase in liver and kidney microsomes (Schoenmakers, et al., *Biochem. Biophys. Res. Commun.* 162:857-868 (1989); Safran, et al., *Endocrinology* 126:826-831 (1990); Kohrle, et al., *J. Biol. Chem.* 265:6146-6154 (1990); Kohrle, et al., *J. Biol. Chem.* 265:6155-6163 (1990)) and more recently in microsomes from human liver (Schoenmakers and Pigmans, *Program of the 10th International Thyroid Conference,* Rotterdam (1991), p. 320 (abstract)). Results in FIG. 12 provide conclusive evidence that a protein of this size is the Type I deiodinase as it is only present in cells transfected with plasmids expressing the human or rat 5' deiodinase. Reduction in the $BrAcT_3$ labelling of both human and rat deiodinases by excess cold bromoacetyl $T_3$ indicates that the covalent labelling process is specific as does displacement by gold thioglucose, a competitive inhibitor of $rT_3$ 5' deiodination. The 30 $\mu m$ concentration of $T_4$ does not inhibit labelling of the human 5' deiodinase, but we expect inhibition would occur at a higher concentration.

The results that indicate that the human Type I 5' deiodinase contains selenocysteine as does the rat 5' deiodinase and that this protein is exquisitely sensitive to inhibition by PTU. Early studies by Nicoloff (Nicoloff, J. T., *J. Clin. Invest.* 49:267-273 (1970)) demonstrated inhibition of $^{131}I$ release from $T_4$ by administration of only 100 mg of PUT to euthyroid subjects. In hyperthyroid patients, PTU causes a dose-related inhibition of $T_4$ to $T_3$ conversion that is reflected in a markedly greater increase in the $T_4$ to $T_3$ ratio of hyperthyroid subjects treated with PTU than with methimazole plus iodide (Abuid and Larsen, *J. Clin. Invest.* 54:201 $\propto$ 208 (1974)). However, reports by both Saberi et al. and Geffner et al. and more recent studies of LoPresti et al. suggest that the impairment of peripheral $T_3$ production by PTU in euthyroid subjects is modest (Saberi, et al., *J. Clin. Invest.* 55:218-223 (1975); Geffner, et al., *J. Clin. Invest.* 55:224-229 (1975)) or absent (LoPresti, et al., *J. Clin. Invest.* 84:1650-1656 (1989)).

Several factors could contribute to the difference in the response to PTU between hyperthyroid and euthyroid subjects and between humans and rats. First, hyperthyroidism increases the hepatic and renal 5' deiodinase in the rat by increasing the mRNA (Berry, et al., *Nature* 349:438-440 (1991); Berry, et al., *Mol. Endocrinol.* 4:743-748 (1990)). It seems likely that a similar effect would occur in hyperthyroid man, making the Type I enzyme a more important source of $T_3$ in hyperthyroid than in euthyroid individuals. Secondly, Graves' immunoglobulin has been shown to stimulate 5' deiodinase activity in FRTL5 cells (Toyoda, et al., *J. Clin. Endocrinol. Metab.* 70:1506-1511 (1990)) and 5' deiodinase activity is higher in Graves' than in normal thyroid (Ishii, et al., *J. Clin. Endocrinol. Metab.* 52:1211-1217 (1981)). Thus, a portion of the PTU effect to decrease $T_4$ to $T_3$ conversion in patients with Graves' disease could be due to inhibition of thyroidal 5' deiodinase activity. Thirdly, Nicoloff and colleagues (LoPresti, et al., *J. Clin. Invest.* 84:1650-1656 (1989); Nicoloff and LoPresti, "Alternate Pathways of Thyroid Hormone Metabolism," in: *Thyroid Hormone Metabolism,* Blackwell Scientific Publications, Boston, Mass. (1991), pp. 55-64) have speculated that at euthyroid levels of serum $T_4$, a PTU insensitive, low Km, Type II 5'-iodothyronine deiodinase pathway similar to that in hypothyroid rats (Silva, et al., *J. Clin. Invest.* 73:898-907 (1984)), is operative as a major source of peripheral $T_3$ production. Since hyperthyroid individuals have elevated serum $T_4$ concentrations, type I $T_4$, 5' deiodination would make a greater contribution to peripheral $T_3$ production in these individuals.

In iodine sufficient rats and cattle, selenium deficiency causes a compensatory increase in serum $T_4$ concentrations with either no change or reduction in serum $T_3$ (Beckett, et al., *Biochem. J.* 289:887-892 (1989); Arthur, et al., *Res. Vet. Sci.* 45:122-123 (1988)). Contempre et al. recently reported that in a group of Zairian endemic cretins with coexisting endemic selenium deficiency, replacement of selenium caused a further decrease in serum $T_1$ and an increase in TSH with no change in serum $T_3$ concentration (Contempre, et al., *J. Clin. Endocrinol. Metab.* 73:213 $\propto$ 215 (1991)). These changes could be explained by an acceleration of $T_4$ degradation consequent to an increase in the selenoprotein 5' deiodinase which is not compensated for in these severely iodine deficient subjects. These results are consistent with our demonstration of the selenocysteine codon in the human 5' deiodinase gene.

One of the unexpected consequences of the identification of selenium in the active center of the 5' deiodinase enzyme is the observation that the rat and human 5' deiodinase are quite sensitive to inhibition by gold (Table III, Berry et al., *Nature* 349:438-440 (1991); Berry et al., *J. Biol. Chem.* 266:4155-14158 (1991). Inhibition of 5' deiodinase activity occurs after gold administration to rats (Berry, et al., *Endocrinology* 129:550-552 (1991)) and similar effects could occur in man.

A number of unique and as yet poorly delinated steps are involved in the synthesis of selnocysteine-containing proteins (Sunde, R. A., *Annu. Rev. Nutr.* 10:451-474 (1990); Burk, R. F., *FASEB J.* 5:2274-2279 (1991); Bock, et al., *Molec. Microbiol.* 5:515-520 (1991); Stadtman, T. C., *J. Biol. Chem.* 266:16257-16260 (1991)). In eukaryotes, the latter process requires the SECIS motif identified in the human and rat 5' deiodinase mRNAs (Berry, et al., *Nature* 353:273-276 (1991)). Any of these steps could be susceptible to rapid inhibition by the physiological conditions known to cause a decrease in $T_4$ to $T_3$ conversion (Stadtman, T. C., *J. Biol Chem.* 266:16257-16260 (1991)). The availability of the cDNA for the human 5'-deiodinase should facilitate a better understanding of the T4 activation process and its regulation in man.

TABLE III

Kinetic Parameters for Deiodination Catalyzed by the Transiently Expressed and Liver Microsomal Human Type I 5'-Deiodinases

| | $K_a(rT_3)$ µM | $V_{max}(rT_3)$* (pmol min$^{-1}$ mg$^{-1}$) | $K_b$(DTT) (mM) | $K_i(T4 \cdot rT_3)$* (µM) | $K_i(PTU \cdot rT_3)$* (µM) | $K_i(PTU \cdot DTT)$ (µM) | $K_i(GTG \cdot rT_3)$* (nM) |
|---|---|---|---|---|---|---|---|
| Human cDNA | 0.52 | 63.2 (14.5–146) | 5.0 | 6.2 | 0.17 | 0.014 | 4.7 |
| Human Liver Microsomes # | 0.35 | 128–242 | 5.4 | — | 0.28 | 0.10 | — |

All values for inhibition of 5'-monodeiodination of 3,3',5'-triiodothyronine under conditions in which the enzyme is rate-limiting. All reported values are the mean of at least two experiments.
*All reactions contained 10 mM DTT. Hepatic microsomal deiodinase values reported are for 5 mM DTT.
Data from Visser et al., J. Clin. Endocrinol. Metab. 67:17–24 (1988).

It will be appreciated by those skilled in the art that various modifications can be made to the above-described embodiments of the invention without departing from the essential nature thereof. It is intended to encompass all such modifications within the scope of the appended claims.

We claim:

1. An isolated DNA molecule consisting essentially of a DNA segment encoding an enzyme having the activity of Type I iodothyronine 5'-deiodinase.

2. The isolated DNA molecule of claim 1 wherein said enzyme is encoded by the sequence as shown in FIG. 4B (and Sequence ID5), or a sequence encoding a functional derivative thereof.

3. A method of producing a polypeptide containing at least one selenocysteine residue at a desired site, said method comprising:
   (a) preparing an expression vector comprising
      (i) a first DNA sequence encoding said polypeptide, wherein said first DNA sequence contains a TGA codon at a site corresponding to the desired selenocysteine site in said polypeptide;
      (ii) a promoter region capable of directing transcription of said first DNA sequence wherein said promoter region is operably linked to the 5' end of said first DNA sequence; and
      (iii) a second DNA sequence wherein said second DNA sequence encodes a selenocysteine-insertion sequence and wherein said second sequence is operably linked 3' to said first DNA sequence and wherein said second DNA sequence is capable of directing the incorporation of selenocysteine into said polypeptide;
   (b) transforming a host cell culture with said expression vector to obtain a transformed, recombinant host cell;
   (c) culturing said recombinant host cell under conditions permitting expression of and of said protein; and
   (d) recovering said protein.

4. The method of claim 3 wherein said selenocysteine-insertion sequence is encoded by nucleotides 1573-1894 as shown in FIG. 4B (and Sequence ID5), or a functional derivative thereof.

5. An isolated reporter gene consisting essentially of a DNA sequence encoding a functional Type I 5' deiodinase.

6. The reporter gene of claim 5 wherein the sequence encoding Type I 5'-deiodinase is that shown in FIG. 4B (and Sequence ID 5).

7. The reporter gene of claim 5 wherein the codon for selenocysteine is replaced with that for cysteine.

8. A linear vector comprising the isolated DNA molecule of claim 1.

9. The linear vector of claim 8, further comprising a DNA sequence which directs expression of said enzyme.

10. The linear of vector of claim 8 further comprising a DNA sequence encoding a selenocysteine-containing polypeptide operably linked to said DNA molecule and a second DNA sequence capable of directing expression of said polypeptide.

11. A host cell transformed with the linear vector of claim 8, said host cell being capable of expressing an enzyme having the activity of Type I iodothyronine 5' deiodinase.

12. An isolated selenocysteine-insertion sequence which, when operably linked 3' to a DNA sequence encoding a selenocysteine-containing polypeptide, effects incorporation of selenocysteine into said polypeptide.

13. The isolated selenocysteine-insertion sequence of claim 12 which is encoded by nucleotides 1573–1894 as shown in FIG. 4B (and Sequence ID 5).

14. An expression vector for the synthesis of a selenocysteine-containing polypeptide, wherein said expression vector comprises:
   (a) a first DNA sequence encoding said selenocysteine-containing polypeptide operably linked to a promoter region; and
   (b) a second DNA sequence which encodes a selenocysteine-insertion sequence, wherein said second DNA sequence is operably linked to said first DNA sequence and said second DNA sequence directs the incorporation of selenocysteine into said selenocysteine-containing polypeptide, and wherein said second DNA sequence is not translated.

15. A host cell transformed with the expression vector of claim 14.

* * * * *